(12) United States Patent
Tran

(10) Patent No.: US 12,137,979 B2
(45) Date of Patent: *Nov. 12, 2024

(54) EYE SYSTEM

(71) Applicant: Bao Tran, Saratoga, CA (US)

(72) Inventor: Bao Tran, Saratoga, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/239,116

(22) Filed: Aug. 28, 2023

(65) Prior Publication Data

US 2023/0404398 A1 Dec. 21, 2023

Related U.S. Application Data

(63) Continuation of application No. 17/687,611, filed on Mar. 5, 2022, now Pat. No. 11,779,213, which is a continuation of application No. 16/454,903, filed on Jun. 27, 2019, now Pat. No. 11,298,017.

(51) Int. Cl.

| | |
|---|---|
| *A61B 3/14* | (2006.01) |
| *A61B 3/00* | (2006.01) |
| *A61B 3/10* | (2006.01) |
| *A61B 3/107* | (2006.01) |
| *A61B 3/16* | (2006.01) |
| *G03B 29/00* | (2021.01) |
| *G16H 30/40* | (2018.01) |

(52) U.S. Cl.
CPC .............. *A61B 3/14* (2013.01); *A61B 3/0008* (2013.01); *A61B 3/0016* (2013.01); *A61B 3/107* (2013.01); *A61B 3/16* (2013.01); *G16H 30/40* (2018.01); *G06T 2207/20084* (2013.01); *G06T 2207/30041* (2013.01)

(58) Field of Classification Search
CPC ........... A61B 3/14; A61B 3/103; A61B 3/113; A61B 3/1208; A61B 3/1225; A61B 3/024; A61B 3/032; A61B 3/02; A61B 3/18; A61B 1/2275; A61B 2017/00787; A61B 1/227; A61F 11/00; A61F 11/04
USPC .............. 351/206, 200, 205, 209, 210, 218, 351/221–223, 245–246; 396/18
See application file for complete search history.

(56) References Cited

U.S. PATENT DOCUMENTS

| | | | | |
|---|---|---|---|---|
| 9,445,713 | B2* | 9/2016 | Douglas | G06F 18/24 |
| 10,002,311 | B1* | 6/2018 | Garnavi | G06N 3/044 |
| 10,468,142 | B1* | 11/2019 | Abou Shousha | G16H 30/20 |
| 2016/0007849 | A1* | 1/2016 | Krueger | A61B 5/1128 |
| | | | | 600/301 |
| 2018/0268737 | A1* | 9/2018 | Garnavi | G06N 3/084 |
| 2019/0110753 | A1* | 4/2019 | Zhang | A61B 3/0025 |
| 2019/0303759 | A1* | 10/2019 | Farabet | G06F 9/455 |
| 2020/0202527 | A1* | 6/2020 | Choi | G06T 5/73 |
| 2020/0345288 | A1* | 11/2020 | Hong | A61B 3/0025 |

FOREIGN PATENT DOCUMENTS

CN 209153623 U * 7/2019

* cited by examiner

*Primary Examiner* — Dawayne Pinkney
(74) *Attorney, Agent, or Firm* — PatentPC; Bao Tran

(57) ABSTRACT

A method to analyze an eye with a mobile device includes capturing an eye image using a mobile device camera coupled to a processor; capturing gyroscope or accelerometer readings as image metadata to aid in orientation normalization and image registration by the processor; extracting features of the eye using the image corrected with image metadata; and applying the extracted features to a deep learning neural network to detect eye focus data or eye gaze data.

20 Claims, 11 Drawing Sheets

(a) Inception module, naïve version

EYE SYSTEM

INCORPORATION BY REFERENCE

All publications and patent applications mentioned or cited in this specification are herein incorporated by reference in their entirety to the same extent as if each individual publication or patent application was specifically and individually indicated to be incorporated by reference.

COPYRIGHT NOTICE

A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

BACKGROUND

The present system relates to body imaging and diagnosis.

Lasers are extensively in designators, rangefinders and guidance systems. The military is actively exploring uses of high-powered military lasers, suppressing the opposition by temporarily blinding sniper positions, pointing and directing fire to specific targets, distraction devices, psychological warfare to dazzle and confuse the enemy are just some of the ways military lasers are used. Class IV lasers are producing over 500 mW of output and are slowly becoming part of the military arsenals to provide non-lethal engagements in sensitive areas of operations. Anti-eye laser weapons are being developed which would cause new types of combat casualty which have not yet been extensively experienced, but which will require accurate diagnosis to ensure effective medical solutions. Even laser pointers can cause damage.

SUMMARY

In one aspect, systems and methods are disclosed to inspect an eye includes capturing an eye image using a mobile device camera; extracting features of the eye; applying a deep learning neural network to detect the eye for identification.

In implementations, described herein are methods and apparatuses (device and methods) to help guide a subject in taking an image of a body region (e.g., fundus of eyes, or nose, ear openings, among others), as well as method and apparatuses for identifying the body region from one or more images, and methods of identifying similar images from a large database of images, and methods and apparatuses for assisting in diagnosis using the image(s), and methods of applying deep learning machines to images for medical diagnosis.

In one aspect, a method to inspect an eye includes capturing an eye image using a mobile device camera; extracting features of the eye; applying a deep learning neural network to detect potential eye damage; and reporting the potential eye condition.

In another aspect, a method to inspect a nose includes capturing a nose image using a mobile device camera; extracting features of the nose; applying a deep learning neural network to detect potential nose damage; and using the analysis for eye identification or treatment.

In another aspect, a method to inspect an ear includes capturing an ear image (including membranes such as tympanic membranes) using a mobile device camera; extracting features of the ear; applying a deep learning neural network to detect potential ear damage; and reporting the potential ear damage for treatment.

In another aspect, a method to inspect a stomach includes threading a fiber optic cable to the stomach and capturing stomach images using a mobile device camera; extracting features of the stomach; applying a deep learning neural network to detect potential stomach damage; and reporting the potential damage for treatment.

In another aspect, a method to inspect includes capturing a throat image using a mobile device camera; extracting features of the throat; applying a deep learning neural network to detect potential throat problems; and reporting the potential throat damage for treatment.

Implementations of the above aspects may include one or more of the following operations: providing an adapter to couple the mobile device to the eye; positioning one or more light emitters or light pipes to carry light from the mobile device in an adapter; capturing stereo images of the eye; applying a conditional GAN to learn image pattern; generating features and applying the features to detect similar eye conditions; retrieving treatment or diagnosis information from the detected similar eye conditions; generating historical feature vectors from one or more eye examinations of a patient, training the deep learning neural network with the historical feature vectors along with eye images, and applying the trained deep learning neural network to diagnose the eye; detecting laser damage on the eye using the deep learning network; providing a similarity search for the eye image; displaying from a database eye images similar to the eye image captured by the mobile device camera. The mobile device camera can be an optical zoom lens. The adapter can include additional multispectral sensors to supplement the smart phone cameras. The operation may include one or more of the following: controlling the optical zoom lens to focus on the posterior of the eye; and may include having neural network assist in focusing on structures on the posterior of the eye; providing background lighting for imaging cataract in the eye with retroillumination; determining intraocular pressure (IOP) with the deep learning neural network; calibrating the IOP with a tonometer; imaging a posterior of the eye with solid state lighting units and light conditioning optics; emitting light with narrow spectral bandwidth, broad spectral bandwidth, visible spectrum, or invisible spectrum; placing light sources and sensors in an adapter positioned between the mobile device camera and the eye. The adapter may support two or more cameras in the mobile device to image the eye.

Advantages may include one or more of the following. For laser injuries, the clinical decision support tool to detect retinal injury will enable decisions to be made at the Role 3 level and allow physicians to determine the best treatment plan. The development of accurate and smart ocular diagnostic technology will expand the capability of clinicians to diagnose and treat ocular injuries induced by laser exposure at the point-of-injury as well as point-of-care. The technology will provide improved field-care capabilities, reduce recovery time of injured people, and help minimize complications of wound healing after trauma or surgery. This test if developed on a mobile device would be a valuable tool in the hands of the users for quick analysis if in doubt, and also to eye care providers worldwide to assist in the evaluation of laser induced retinal injuries. End-users receive appropriate care and will return to duty more quickly. Quality of care will be improved for soldiers who suffer laser-induced retinal injury that may not be detected immediately after exposure without a rapid portable diagnostic tool. For commercial users who experience laser pointer issues, the system also enables quick and thorough diagnostics.

DETAILED DESCRIPTION

Figure 1A:
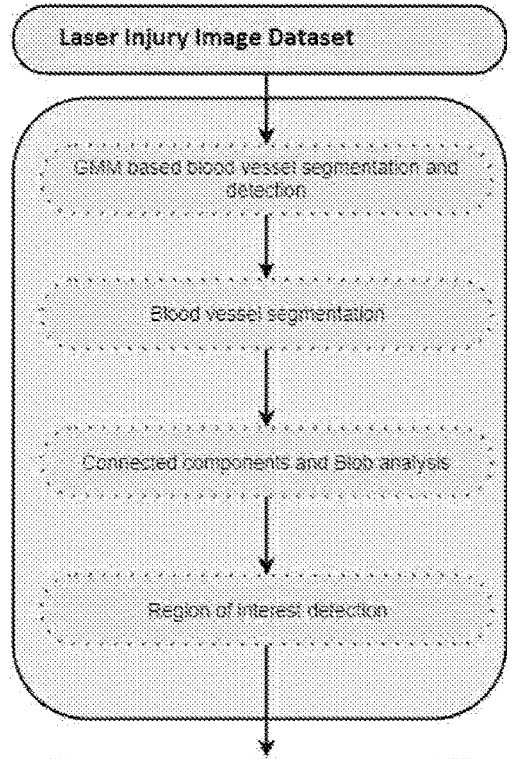
FIGS. 1A-1C show exemplary high level processes to analyze eyes.

FIG. 1A shows an exemplary high level process to analyze eye structures, possibly eyes damaged such as laser damaged eyes, among others. In one embodiment for analyzing eyes, the process includes receiving an image dataset, and performing preprocessing for blood vessel segmentation/detection, connected component analysis, and blob analysis, and ROI detection. The features extracted after the pre-processing are provided to a deep learning network such as a conditional GAN for learning, and the trained network is applied in the field using a smart phone and an inexpensive camera adapter for fundus image capture, as detailed in FIGS. 3A-3B, for example.

Initially the system is trained using data captured by the mobile device or by conventional eye imaging systems. For example, the training data contains a large number of fundus images with a high resolution taken by different levels of fundus cameras and labeled with right and left eyes. The fundus images can be captured by different fundus cameras with different conditions and quality levels. Some of them were treated as normal images, but few of them had some noise in the form of dots, circles, triangles, or squares. In these conditions, some images are able to overturn. Noisy images can also be considered as out of focused, blurry, under-exposed, and over-exposed images. The noisy data is useful to avoid overtraining the neural networks.

Preprocessing is helpful to figure out and differentiate between actual lesions or features of laser injury from the noisy data. Therefore, before feature extraction, it can be necessary to perform a preprocessing operation on the raw pavement digital images. In the proposed computer aided diagnosis system, one purpose of preprocessing is to identify the blood vessels in the form of microaneurysms (MAs). During the preprocessing phase, algorithmic techniques are performed including the grayscale conversion technique to demonstrate better contrast, while the shade correction technique is performed to estimate the image, then subtracts it from the existing image. In the next phase, vessel segmentation is applied based on GMM. The fundus images can be used to extract the information from the colored image to the background extracted vision. Image processing features can accentuate the following: 1) Image quality quantification: image quality verification; imaging artifact detection; iatrogenic lesion detection (laser scars, etc.); 2 Location and segmentation of retinal structures: retinal vessels; vessel diameter; artery and vein classification; vessel occlusion detection; fovea optic disc cup and rim; cupping; and 3) Segmentation of abnormalities: blood vessel related abnormalities hemorrhages; microaneurysms; neovascularizations; nerve fiber infarcts (cottonwool spots); pigment epithelium related abnormalities drusen; hyper and hypopigmentation, choroid related abnormalities nevus and melanoma detection; and uveitis related choroidal lesions. The background image contains the most discriminant form of the image. To achieve the most discriminant information, the adaptive learning rate (ALR) can provide high performance in the region of interest (ROI).

Before applying the feature extraction, blood vessel extraction can be performed with the association of ROI localization. In this phase, blood vessel segmentation can be applied to extract the ROI in the images. For this purpose, there are many techniques that can be applied including ROI based segmentation, edge-based segmentation, fuzzy models, and neural networks. A Gaussian mixture technique is used for vessel segmentation where Gaussian sorting is used to obtain the background subtraction approach. A hybrid approach can use the Gaussian mixture model (GMM) based on an adaptive learning rate (ALR) to obtain better region detection results. The Gaussian mixture g(x) with j components can be used for the ROI for calculation and ALR can be defined to update the µj repeatedly with the use of the probability constraint to identify whether a pixel can be an element of the jth Gaussian distribution or not. Candidates for feature detection include template matching, kernel convolution, detector correlation. Pixel feature classification is a machine learning technique that assigns one or more classes to the pixels in an image. Pixel classification uses multiple pixel features: numeric properties of a pixel and its surroundings. Pixel feature classification is typically performed using a supervised approach, but we will test unsupervised learning networks. N-dimensional multifeature vectors are utilized including pixel contrast with the surrounding region, its proximity to an edge, and similarity. Two distinct stages are required for a supervised learning/classification algorithm to function: 1) a training stage, in which the algorithm "statistically learns" to correctly classify pixels from known classifications, and 2) a testing or classification stage in which the algorithm classifies previously unseen images. For proper assessment of supervised classification method functionality, training data and performance testing data sets must be completely disjoint. The n-dimensional multifeature vectors are calculated for each pixel, frequently utilizing local convolutions with multiple Gaussian derivative, Gabor, or other wavelet kernels. The image is thus transformed into an n-dimensional feature space and pixels are classified according to their position in feature space. The resulting hard (categorical) or soft (probabilistic) classification is then used to either assign labels to each pixel (for example vessel or nonvessel in the case of hard classification), or to construct class-specific likelihood maps (e.g., a vesselness map for soft classification). For example, an image $Ii(x, y)$ can be transformed into the Gaussian derivative space $Ii(x, y, \sigma k)$ by convolution with Gaussian derivative kernels $Ii(x,y,\sigma k)=I0(x,y) \star G\alpha n(\sigma k)$ where $\star$ represents convolution, $\sigma k \in [0, \infty)$ is the relative scale, and G is the Gaussian derivative kernel of order $n \in \{0, 1, 2\}$ with orientation $\alpha \in [0, \ldots, 2\pi]$. The number of potential features in the multifeature vector that can be associated with each pixel is essentially infinite. One or more subsets of this infinite set can be considered optimal for classifying the image according to some reference standard. Hundreds of features for a pixel can be calculated in the training stage to cast as wide a net as possible, with algorithmic feature selection steps used to determine the most distinguishing set of features. Extensions of this approach include different approaches to subsequently classify groups of neighboring pixels by utilizing group properties in some manner, for example cluster feature classification, where the size, shape and average intensity of the cluster may be used.

Because retinal vessel diameter and especially the relative diameters of arteries and veins are known to signal the risk of systemic diseases including stroke, accurate determination of retinal vessel diameters, as well as differentiation of veins and arteries have become more important, several semi-automated and automated approaches can be applied. Other operations include separation of arteries and veins, detection of small vessels with diameters of less than a pixel, and analysis of the complete vessel trees using graphs. The detection of lesions can use the following. A transform is used for detecting candidate lesions, after which a mathematical morphology template is utilized to characterize the candidates. This approach or a modification thereof is in use in many algorithms for detecting laser damage to the fundus. Preprocessing steps, such as shade-correction and matched filter post-processing to this basic framework, can improve performance. Algorithms of this kind function by detecting candidate microaneurysms of various shapes, based on their response to specific image filters. A supervised classifier can be developed to separate the valid microaneurysms from spurious or false responses. The top-hat algorithm is modified to red-free fundus photographs, and also by broadening the candidate detection transform to a multifilter filter-bank approach. The filter responses are used to identify pixel candidates using a classification scheme. Mathematical morphology and additional classification steps are applied to these candidates to decide whether they indeed represent microaneurysms and hemorrhages. A similar approach can be also successful in detecting other types of lesions, including exudates or cotton-wool spots, as well as drusen in AMD. Once the appropriate feature sets are determined, the deep learning architecture can be done.

Following the enhancement and augmentation processes, algorithms are applied to identify retinal abnormalities associated with laser damage. Retinal laser lesions that cause serious visual problems are readily apparent ophthalmoscopically and angiographically and the deep learning system can identify those cases with near perfect score. For ambiguous cases, we analyze laser-tissue interactions and the characteristics of unambiguous retinal laser injuries provide key features to facilitate difficult diagnoses by human professionals.

Figure 1B:
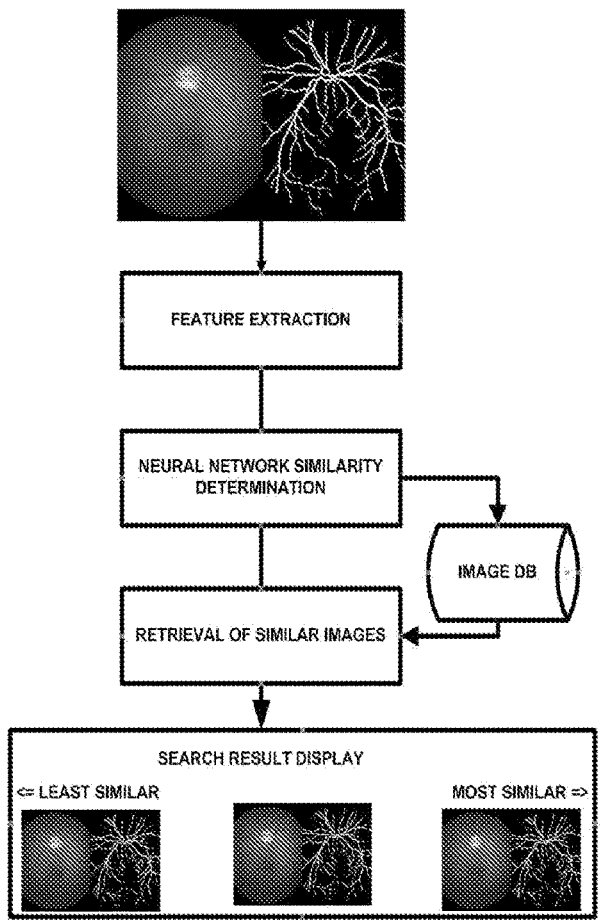

In FIG. 1B, the images and features/metadata are stored in an image database. For case analysis, a new image is provided, and preprocessing/feature extraction are done. A neural network such as a GAN network determines images that are similar, and similar images are retrieved for research, ordered from least similar to most similar by the neural network. Based on the most similar image, the doctor can retrieve historical treatment information from the most relevant cases to give the doctor precedential treatment data.

Figure 1C:
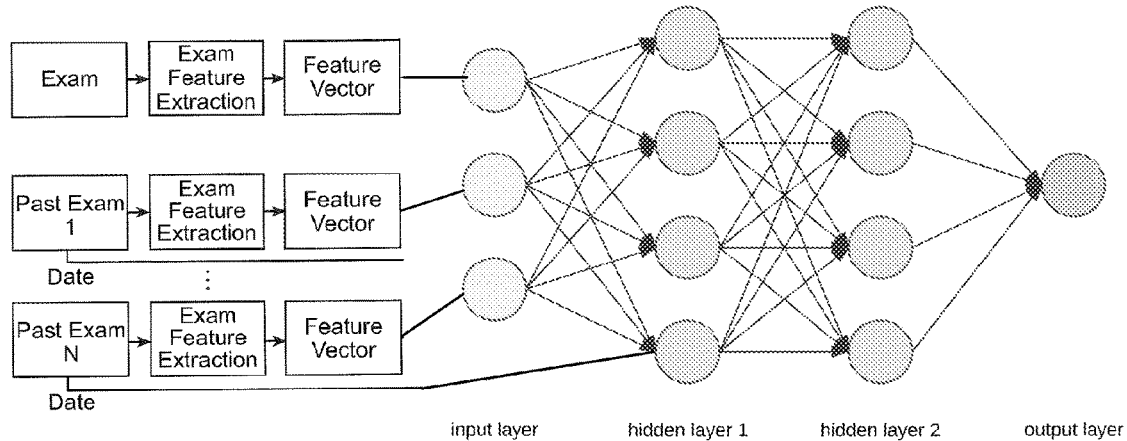

In FIG. 1C, during examination, a doctor uses a smartphone to capture the fundus image of the patient. Feature extraction is done on the images as detailed herein. In parallel, clinical information such as sex, age, temperature, medical history, work history, among others, are provided to a feature extraction. As the data is text, the feature extraction can be done by extracting feature windows around a particular word of interest. The description can be vectorized into a sparse two-dimensional matrix suitable for feeding into a classifier. Feature hashing, where instead of building a hash table of the features encountered in training, as the vectorizers do, instances of FeatureHasher apply a hash function to the features to determine their column index in sample matrices directly. Since the hash function might cause collisions between (unrelated) features, a signed hash function is used and the sign of the hash value determines the sign of the value stored in the output matrix for a feature. This way, collisions are likely to cancel out rather than accumulate error, and the expected mean of any output feature's value is zero.

In addition, prior examination data can be featurized. At the time of a given exam, relevant information for predicting the diagnosis or prognosis may come not only from the current exam, but also from the results of past exams. The system combines information from the current and past exams when making a prediction of diagnosis or prognosis. If all patients received regular exams, for example, annually, it would be possible to simply generate one feature vector for the current exam, another for the exam from 1 year ago, another for the exam from 2 years ago, etc. Those feature vectors could then be combined via simple concatenation (possibly followed by dimensionality reduction) using the same procedure described herein to combine features within a single exam to form a combined feature vector. However, in general, patients may not be expected to all have had regular past exams on the same schedule. For example, patient A may have had annual exams, patient B may have had exams every other year, and patient C may have only had exams during periods of illness, which occurred at irregular intervals. Therefore, there is a need for a consistent method of converting information from past exams into a feature vector in a way that does not depend on the frequency or interval between past exams. One possible method for combining information from past exams is to combine features from past exams via a weighted average that takes into account the time from the current exam, with more recent exams weighted higher. For example, a linear weighting function could be used which linearly runs from 0 at birth to 1 at the present time. For an example patient of age 10 who had exams at ages 3 months, 9 months, and 6 years, each feature would be averaged together across exams (excluding the present exam), with weights of 0.025, 0.075 and 0.6. Weighting functions other than linear could be used (e.g., logarithmic, power law, etc.) and weights could also be normalized to add up to 1. Features from the current exam would also be included separately in the feature vector, concatenated together with the weighted features from past exams. Alternatively, one could include the current exam's features in the weighted feature vector from past exams, instead of including it separately. The generated feature vectors are then provided to a deep learning system.

Figure 2A:
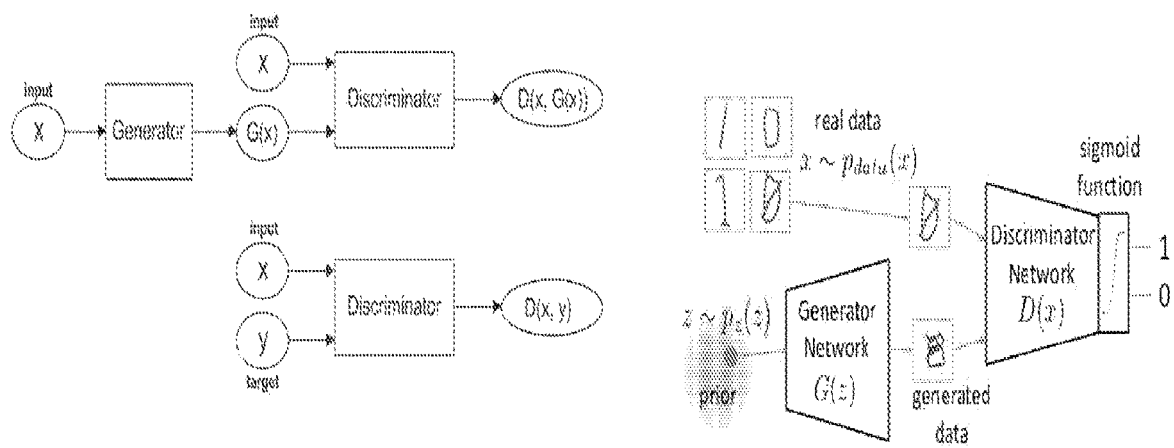
FIG. 2A shows exemplary deep learning systems for eye structure recognition.
Figure 2B:
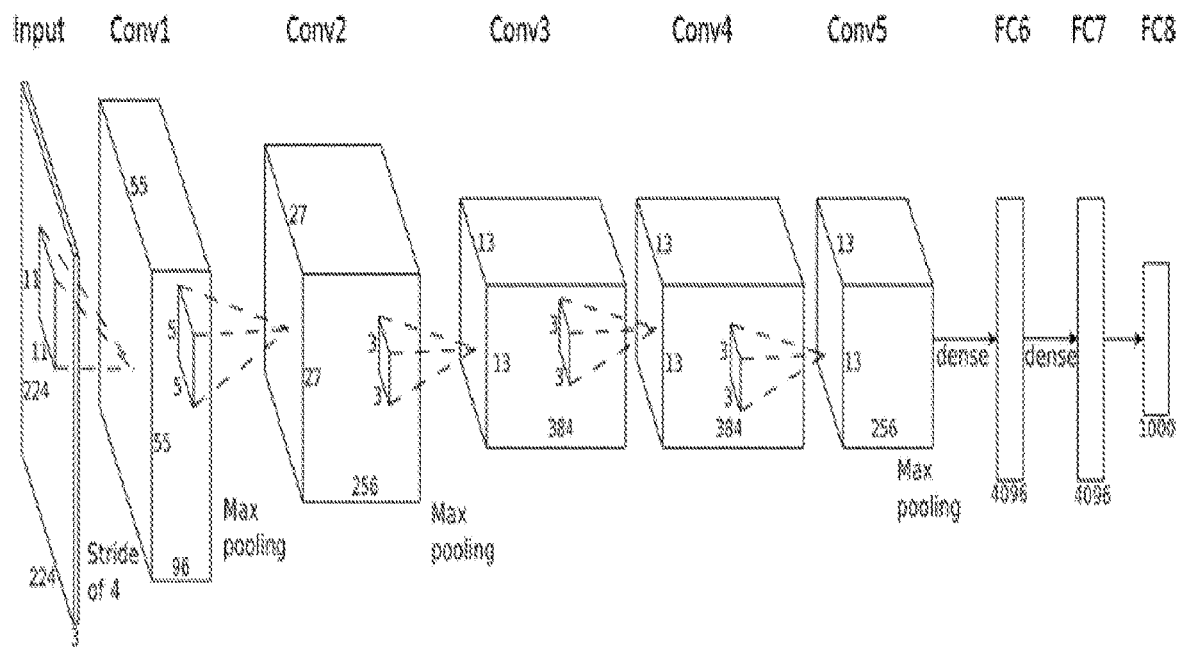
FIGS. 2B-2J show alternative exemplary deep learning systems for eye structure recognition.
Figure 2C:
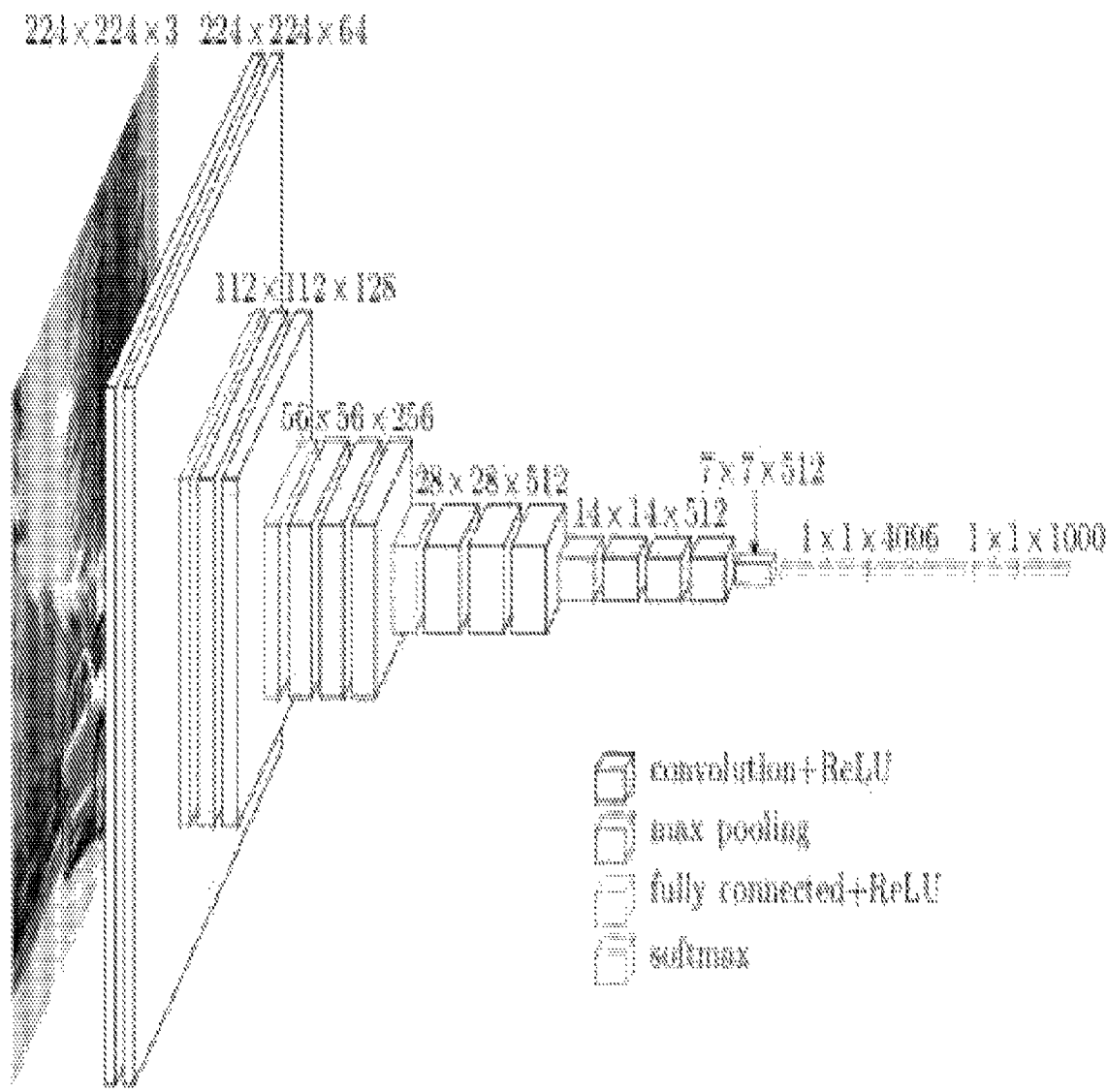
Figure 2D:
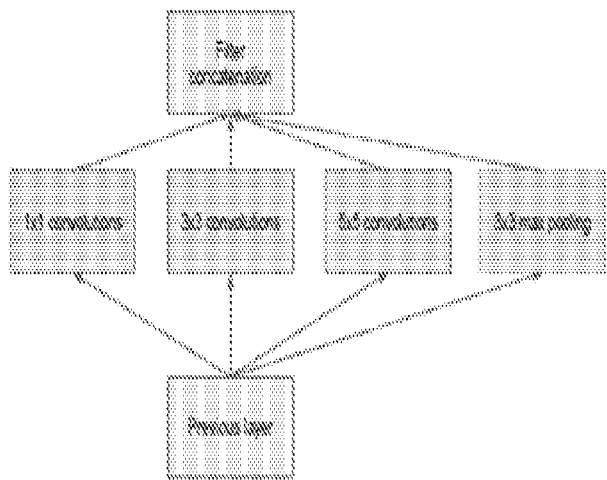
Figure 2D:
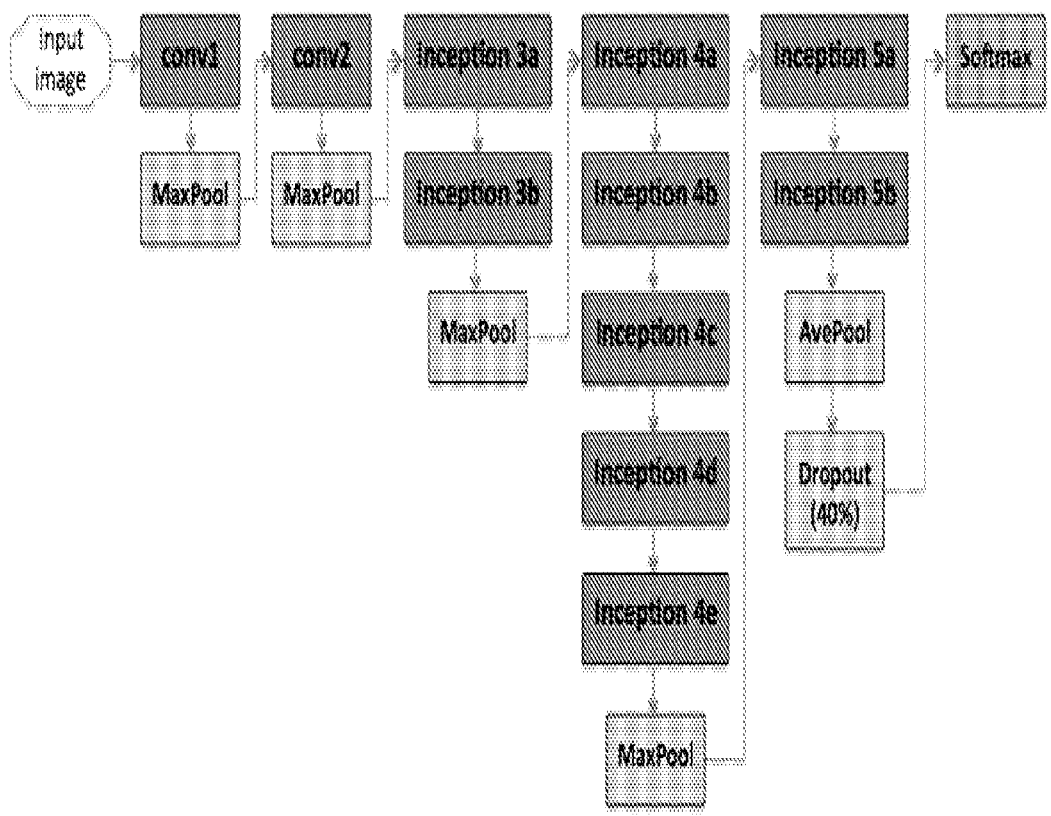
Figure 2E:
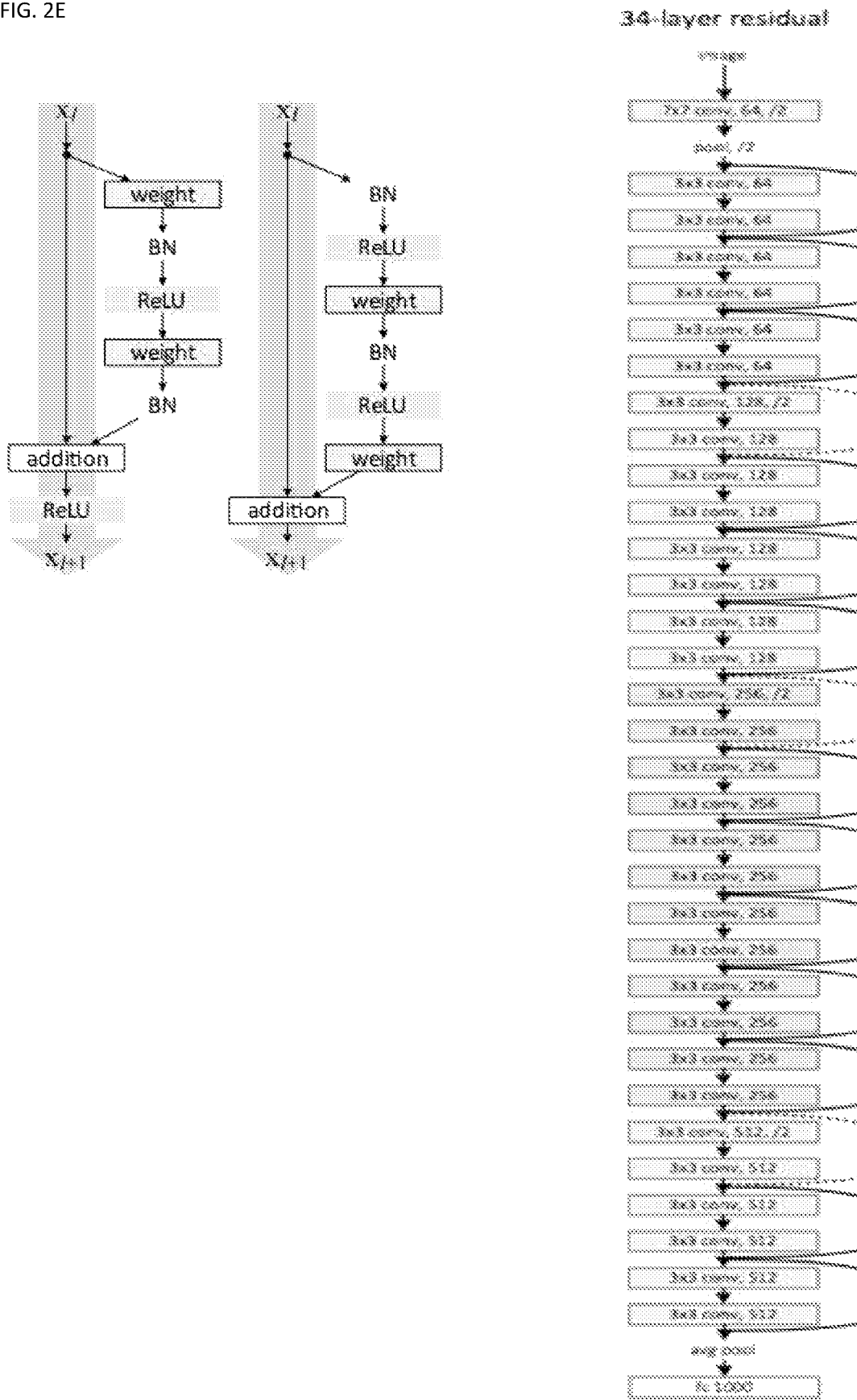
Figure 2F:
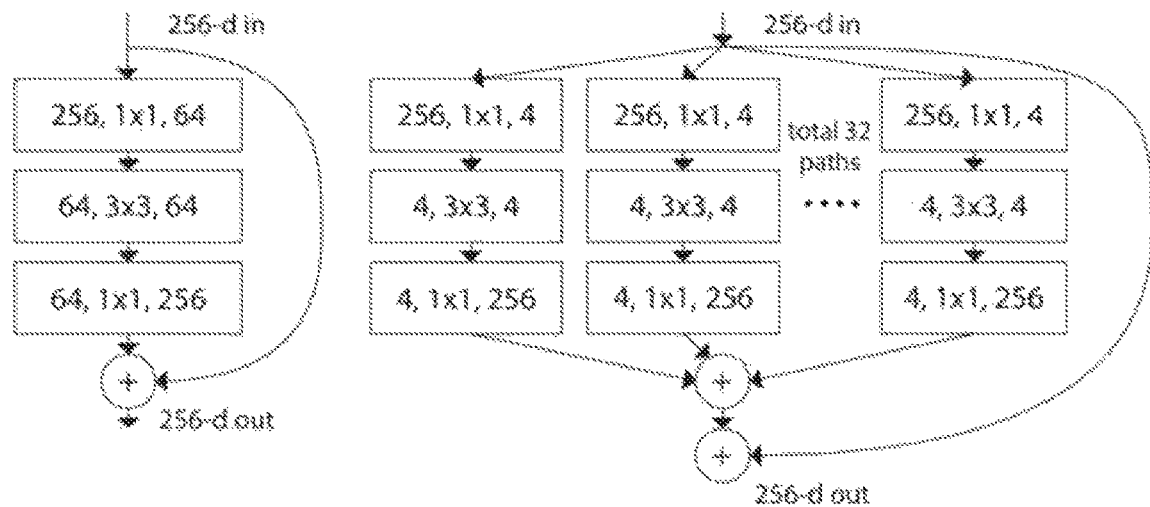
Figure 2G:
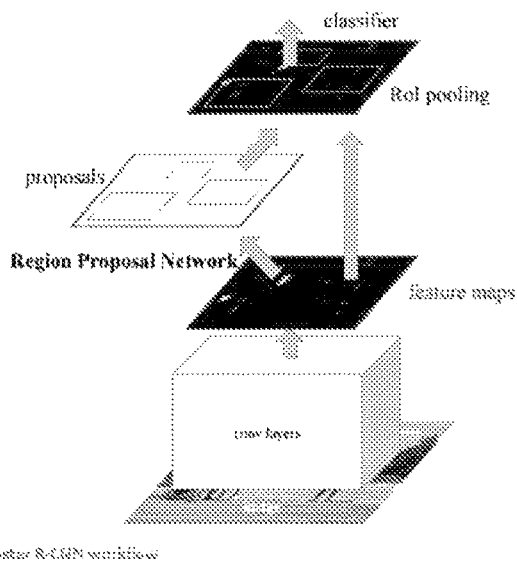
Figure 2G:
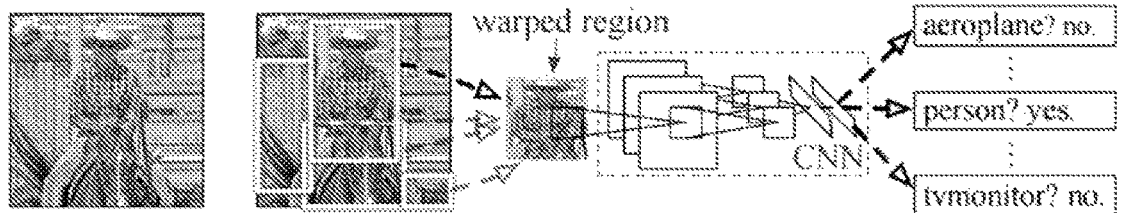
Figure 2H:
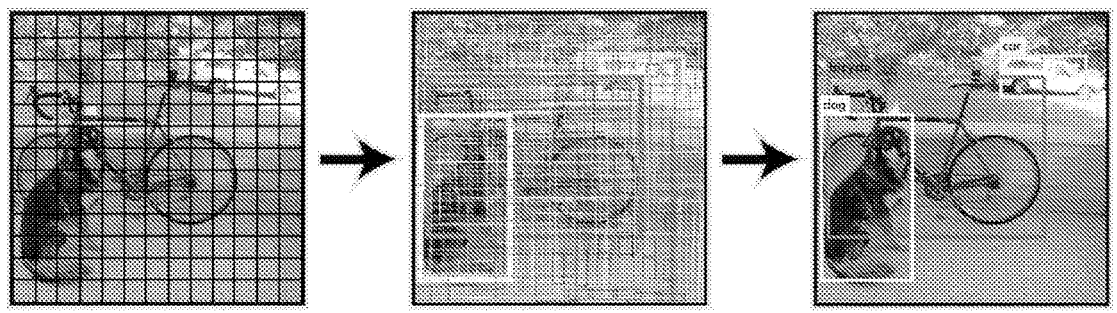
Figure 2H:
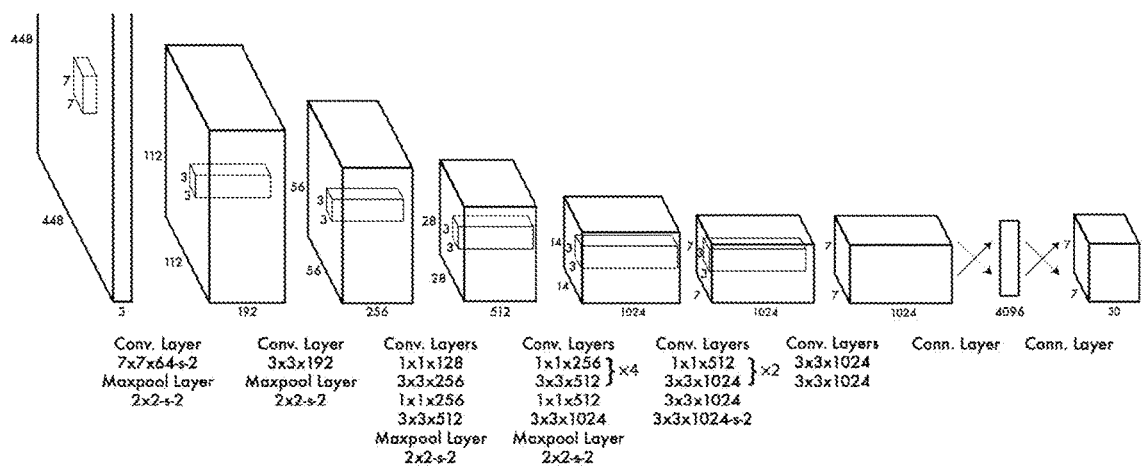
Figure 2J:
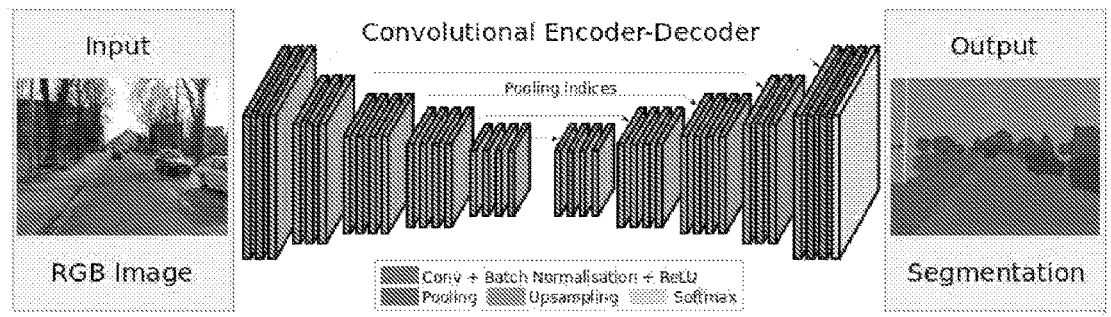
Figure 2I:
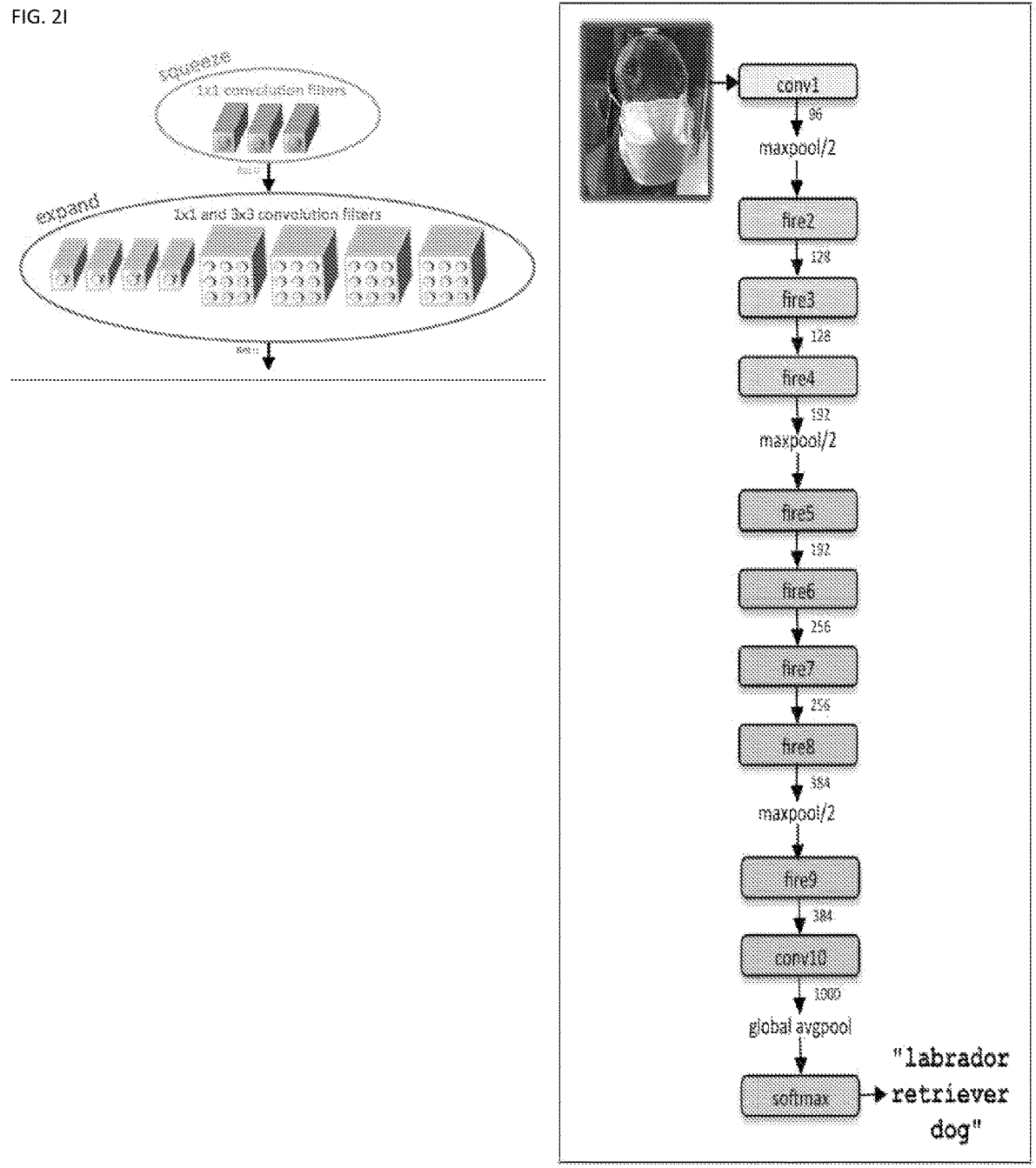

One embodiment uses a conditional-GAN (cGAN) as a deep learning machine. As shown in FIG. 2A, the cGAN consists of two major parts: generator G and discriminator D. The task of generator is to produce an image indistinguishable from a real image and "fool" the discriminator. The task of the discriminator is to distinguish between real image and fake image from the generator, given the reference input image.

The objective of a conditional-GAN is composed of two parts: adversarial loss and L1 loss. The adversarial loss can be: $\mathcal{L}_{cGAN}(G, D)\ E_{x,y}[\log\ D(x,y)]+E_x[\log(1-D(x,G(x))]$ where L1 distance is added to generated image. L1 distance is preferred over L2 distance as it produces images with less blurring. Thus our full objective for the minimax game is:

$$(G^*, D) = \arg \min_G \max_D (\mathcal{L}_{cGAN}(G, D) + \lambda \mathcal{L}_{L1}(G))$$

The ResNet-50 network by He et al. can be used as the generator, while the discriminator can be a convolutional "PatchGAN" classifier with architecture similar to the classifier in pix2pix as our discriminator.

In addition to cGAN, other neural networks can be used. FIGS. 2B-2J show exemplary alternatives, including:

1. AlexNet—AlexNet is the first deep architecture which can be introduced by one of the pioneers in deep learning—Geoffrey Hinton and his colleagues. It is a simple yet powerful network architecture, which helped pave the way for groundbreaking research in Deep Learning as it is now.

2. VGG Net—The VGG Network can be introduced by the researchers at Visual Graphics Group at Oxford (hence the name VGG). This network is specially characterized by its pyramidal shape, where the bottom layers which are closer to the image are wide, whereas the top layers are deep. VGG contains subsequent convolutional layers followed by pooling layers. The pooling layers are responsible for making the layers narrower. In their paper, they proposed multiple such types of networks, with change in deepness of the architecture.

3. GoogleNet—In this architecture, along with going deeper (it contains 22 layers in comparison to VGG which had 19 layers), the Inception module is used. In a single layer, multiple types of "feature extractors" are present. This indirectly helps the network perform better, as the network at training itself has many options to choose from when solving the task. It can either choose to convolve the input, or to pool it directly. The final architecture contains multiple of these inception modules stacked one over the other. Even the training is slightly different in GoogleNet, as most of the topmost layers have their own output layer. This nuance helps the model converge faster, as there is a joint training as well as parallel training for the layers itself.

4. ResNet—ResNet is one of the monster architectures which truly define how deep a deep learning architecture can be. Residual Networks (ResNet in short) consists of multiple subsequent residual modules, which are the basic building block of ResNet architecture. ResNet uses of standard SGD instead of a fancy adaptive learning technique. This is done along with a reasonable initialization function which keeps the training intact; Changes in preprocessing the input, where the input is first divided into patches and then feeded into the network. The main advantage of ResNet is that hundreds, even thousands of these residual layers can be used to create a network and then trained. This is a bit different from usual sequential networks, where you see that there is reduced performance upgrades as you increase the number of layers.

5. ResNeXt—ResNeXt is said to be the current state-of-the-art technique for object recognition. It builds upon the concepts of inception and resnet to bring about a new and improved architecture.

6. RCNN (Region Based CNN)—Region Based CNN architecture is said to be the most influential of all the deep learning architectures that have been applied to object detection problem. To solve detection problem, what RCNN does is to attempt to draw a bounding box over all the objects present in the image, and then recognize what object is in the image.

7. YOLO (You Only Look Once)—YOLO is a real time system built on deep learning for solving image detection problems. As seen in the below given image, it first divides the image into defined bounding boxes, and then runs a recognition algorithm in parallel for all of these boxes to identify which object class do they belong to. After identifying this classes, it goes on to merging these boxes intelligently to form an optimal bounding box around the objects. All of this is done in parallelly, so it can run in real time; processing up to 40 images in a second.

8. SqueezeNet—The squeezeNet architecture is one more powerful architecture which is extremely useful in low bandwidth scenarios like mobile platforms. This architecture has occupies only 4.9 MB of space, on the other hand, inception occupies ~100 MB! This drastic change is brought up by a specialized structure called the fire module which is good for mobile phone.

9. SegNet—SegNet is a deep learning architecture applied to solve image segmentation problem. It consists of sequence of processing layers (encoders) followed by a corresponding set of decoders for a pixelwise classification. Below image summarizes the working of SegNet. One key feature of SegNet is that it retains high frequency details in segmented image as the pooling indices of encoder network is connected to pooling indices of decoder networks. In short, the information transfer is direct instead of convolving them. SegNet is one the best model to use when dealing with image segmentation problems.

Next is a discussion of the mobile device for eye analysis. Preferably, a low cost eye analysis system leverages the components of a smart phone using an adapter 10 which operates stand alone, or holds a viewing instrument 12 in an aligned relationship with an imaging device that captures images of the subject being viewed (ophthalmoscope) and the ophthalmological imaging apparatus allows a medical practitioner to easily view and record images of the retina and the anterior segments of the eye, including the optic nerve. Further, the ophthalmological imaging apparatus provides the medical practitioner with a complete view of the entire optic nerve, not just a partial view. Additionally, the ophthalmological imaging apparatus provides the medical practitioner with a full image of a patient's eye. Accordingly, it will be appreciated that the users of the present device can be a range of medical practitioners, such as optometrists, doctors, and nurses. It will also be appreciated that the preferred embodiment described herein is exemplary in nature, and as discussed below, the present invention can be applied directly above the eye or alternatively through a suitable viewing instrument 12, including any type of a medical scope as well as other types of scopes used by professionals in other industries or in education or any viewing instrument used by amateurs for sports and hobbies.

Figure 3A:
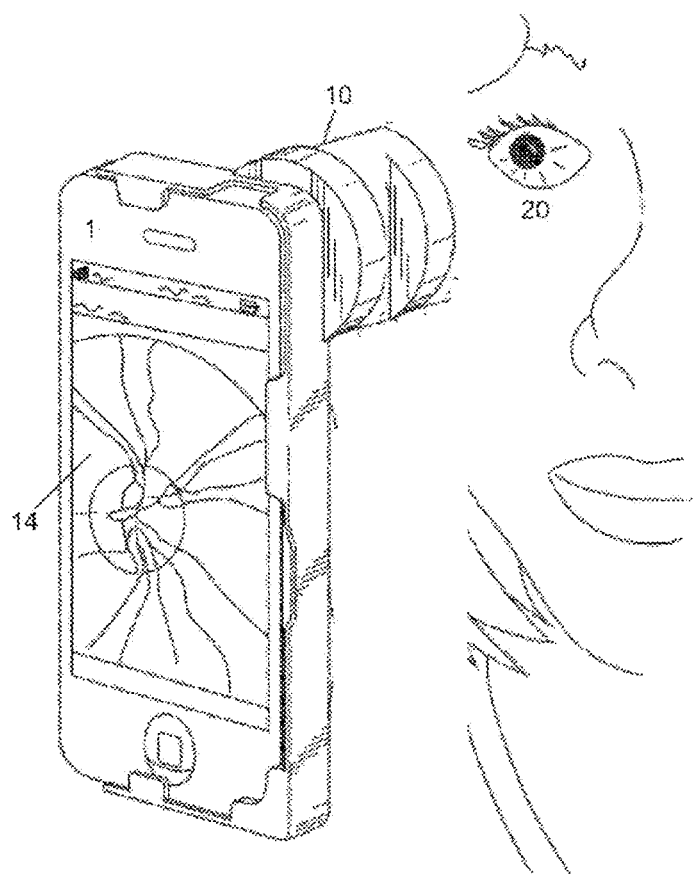
FIGS. 3A-3B show exemplary adapters for use with smart phones to detect eye structures.
Figure 3B:
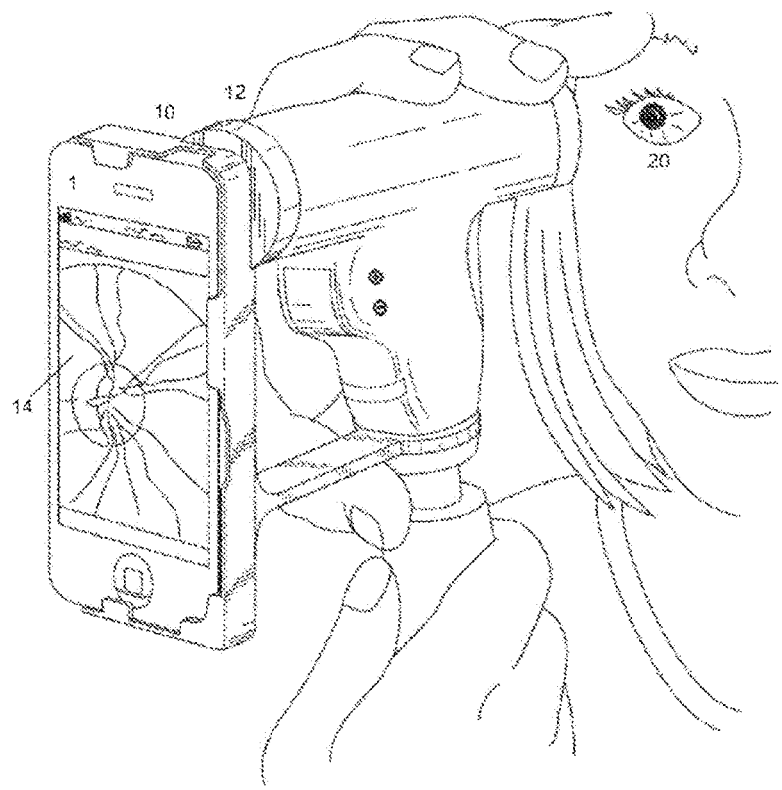

FIG. 3A-3B show the ophthalmic imaging apparatus embodiment of the present invention as it is used in operation with a subject patient. The ophthalmological imaging apparatus allows the mobile imaging device to be in optical communication with an ophthalmoscope. The term "in optical communication" means that two or more devices perceive the same image. For example, a smart-phone in optical communication with the scope head of an ophthalmoscope is capable of capturing the image as viewed by the ophthalmoscope. The ophthalmological imaging apparatus allows a user to view the retina and anterior segment of an eye without the difficulty of aligning both the user's eye and the patient's eye with the ophthalmoscope head. Further, the ophthalmological imaging apparatus provides for a firm and stable mounting of the mobile imaging device to the scope head of an ophthalmoscope at a well functioning angle for examining a patient's eye.

In the embodiment of FIG. 3B, a camera or other image capture device 1 is connected to a viewing instrument 12 through an adapter 10. The adapter 10 has a bracket 14 which holds the imaging device in place within a frame 16. The adapter 10 also has a fitting and a brace which secure spaced-apart sections on the bracket 14 to different corresponding locations on the viewing instrument 12. The image capture device could be any mobile communications device which has a camera system such as a smart phone, such as an Android or Apple iPhone®, tablet computers and PDAs; digital cameras; and digital camcorders. The viewing instrument 12 can be an ophthalmoscope or any other type of scope or viewing instrument. Accordingly, even though the preferred embodiments of the viewing instrument 12 and image capture device 1 are an ophthalmoscope and a smart-phone 110 which may be referred to below as a scope and a camera, respectively, it will be appreciated that the adapter of the present invention can be applied to and used without any intermediate viewing instrument and image capture device.

With the adapter secured to the scope, the frame holds the smart-phone to the bracket so that the camera is positioned in the x, y and z axes with optimal optics. It will be appreciated that the means for attaching the smart-phone to the bracket can be any attachment means known to those skilled in the art, including but not limited to, a pair of arms located on opposite sides of the bracket's body section for slidable engagement with the smart-phone, a pair of arms located at opposite ends of the bracket for slidable engagement of the smart-phone, a case formed with and permanently attached to the bracket so that the case houses the smart-phone, a snap-fitting arrangement wherein a snap-fit is secured to the bracket, and a slidable engagement wherein the mobile imaging device slides into a fitting arrangement with an element located on the first frame member.

The adapter 10 can be modular with brackets being designed to hold particular image capture devices. The fitting for the eyepiece section of the bracket and the brace for the body section of the bracket can be selected for the particular viewing instrument to which the image capture device is to be coupled. For example, an alternative brace could be used to secure the body section of the bracket to a telescope. The frame of the bracket for holding the smart-phone could be the same as described above for the ophthalmoscope. The fitting may have a snap-fit connector which secures the eyepiece section of the bracket to the particular type of view port on the telescope. For example, as discussed above, the snap-fit connector could attach a threaded screw mount to the bracket. Also, the distal end of the brace may have a different type of attachment structure, such as a tube clamp 194 (or a hose clamp). In addition to the ophthalmoscope and the telescope, the adapter can be modified so that other types of viewing instruments 12 can be connected to various types of smart-phones and other cameras. Generally, the adapter can be used for medical imaging devices to facilitate the viewing and capturing of images of a patient's ear, nose, throat or other anatomical feature. Accordingly, the present invention can be used with any medical viewing instrument, such as an endoscope, an otoscope, a dermatoscope, a laryngoscope, a laparoscope and any other medical instrument that is used to view a patient's internal or external anatomy. Additionally, the adapter of the present invention can be further modified and used with other viewing instruments that are used in industry and education or for sports and hobbies, such as the telescope described above or a microscope, a borescope or even a sighting scope, a surveyor scope or binoculars.

With lighting and optics, the smart phone can additionally be used to photograph the posterior of eye when the proper adjustment for focus is made. Solid state lighting units include light emitting diodes (LEDs) and the light conditioning optics in the front. The LEDs could either emit light with narrow spectral bandwidth and in visible or invisible, like UV or IR, spectrum, or can also emit light in broad spectral bandwidth, like white light to human eyes. The LEDs could be turned on at same time, in different combinations or individually. The imaging optics in the front of camera comes with the focusing adjustment capability to allow high quality imaging at different distances. The optics could also employ the optical zooming capability in the smart phone to allow the users to change the magnification of the images for the desired object at a fixed distance. For example, Huawei P30's 5× optical zoom uses a periscope design where components make a 90-degree right turn after the lens cover, and the zoom lens components and CMOS sensor are arranged horizontally to increase optics path for zooming.

The system includes controlling the optical zoom lens to focus on a posterior of the eye; providing a neural network trained to focus on structures on the posterior of the eye; and imaging the posterior of the eye. In one embodiment, the cGAN is used for self-learning on how to focus multi-focus image fusion. In another implementation, a deep learning method fuses multi-focus images with a convolutional neural network (CNN) as a classifier to identify pixels as focused or defocused pixels. In case of unavailability of labeled data to train networks, the method adds Gaussian blur in focused images to produce training data. In another method, which aims to learn feature extraction, fusion and reconstruction components together to produce a complete unsupervised end-to-end trainable deep CNN using a Siamese multi-scale feature extraction module to achieve a promising performance where multiscale convolutions along with skip connections are used to extract more useful common features from a multi-focus image pair. Structure similarity (SSIM) measure is used as a training loss function and the fused images are reconstructed in a multiscale manner to guarantee more accurate restoration of images.

Illumination can be done by a lightpipe which draws light from the phone's LED and redirects it for the desired illumination, including uniform illumination, structured light (to obliquely highlight wrinkles, for example). The attachment device 10 could also contain onboard LEDs or other light sources, with or without onboard power. Although the light sources described herein use LED to describe the light sources in mobile phones and attachments, a variety of light sources may be compatible. Dual source (and higher number) illumination systems on the mobile phone can be used. Another embodiment includes distinct light-directing features over different LEDs (or parts of a multipart LED), which can provide distinct illumination characteristics. For example, the system may be configured to control which of the handset lights is on; one may have a spectral, polarization, intensity, or holographic filter, while another may have a physical lightpipe which provides alternative desired illumination, or any combination of modification features over the light sources. This provides control over the illumination design, without the user having to flip a switch, move a filter, or otherwise be involved in modifying the illumination. For example, the illumination system includes a polarizer at the distal end (nearest to the sample plane), and another polarizer over the camera in a perpendicular configuration. This is very helpful in reducing glare. Calibration may be important in many applications of the system, especially for longitudinal image capture, and embodiments where additional light from the environment may be present. The device 10 can include one or more reference features that alone, or in combination with the illumination system, can provide a tool for color calibration. These features may be in the field of view of the primary camera, or they can use another camera or sensor within or working with the device. For example, the device could have an on-board light meter to measure and compensate for environmental light conditions.

Image registration can be used for comparing longitudinal images. Both software and hardware features may be used to facilitate this image alignment. For example, a hardware reticle or other spatial reference feature may be included, which the user can align with a prominent feature on the surface. The system may provide a semi-transparent overlay of the previous image, to which the user can align the current field of view. Features like these, including magnification, polarization, spectral selection for illumination and recording, integrated calibration, and controlled illumination are all provided by the methods and apparatuses described herein, in conjunction with a mobile phone or other mobile device, or as a stand-alone system. Combined with the display and wireless transmission capabilities of the phone, this is a powerful system for diagnostic imaging. Images can be read locally by software or a person, or transmitted for remote diagnosis. In the case of remote analysis, the response can be sent back to the user along with treatment advice.

The system can capture and analyze serial images to measure physiological response. Longitudinal (serial) images over a period of time can be valuable in tracking the results of a therapeutic intervention (or natural change or healing), even before it is visible to the user or an expert. Changes in color, reduced redness for example, can be hard to detect with the subjective vision of an observer and varying light conditions. The method includes capturing the necessary images or other data, combining with knowledge of the dosage or intensity of the drug or therapy applied, and evaluating changes over time according to key evaluative factors.

During the process of the posterior imaging, the digital focusing mechanism could automatically look for features in the images and try to adjust the optical focus mechanism to achieve the best focus. The overall brightness of the image could be adjusted or set by the users according to their preference. There are two ways to control the brightness of the image, the sensitivity of image sensor or luminance of the lighting. When the quality of the images or the noise level of the image is a critical measure, the sensitivity of the image sensor is often set to a fixed level. Then the luminance of the lighting from the solid state lighting device is adjusted to achieve the desired brightness automatically. Certainly, a maximum level of allowable luminance is set in the apparatus in order to prevent it to exceed the level allowed by regulations due to concern for phototoxicity to the eye. If the level of light exposure is more important, then the level of the luminance from the light source could be fixed or selected by the users, while the sensitivity of the image sensor is adjusted automatically in the second approach.

To determine the color temperature of the incident light, which may prevent proper white balance of the recorded image or video, a small amount of the illumination source is provided directly into the camera system and the processor can measure the temperature of that sample light source, which would always appear in the same region of the recorded image, and adjust white balance accordingly.

In the embodiment of FIGS. 3A-3B, the adapter 10 is part of a smartphone casing where the phone is snappably attached to the smartphone casing. In one modular configuration, the smartphone case (or half-case or other casing interface) contains a battery, image sensor, and light source, and an interface onto which imaging modules can be attached (the "smart case"). These modules could be passive, working with the components of the smart case and the phone to collect data. For example, the smart case (casing interface) could have a battery and an LED, and different modules could be used to tailor the imaging to ear, nose, throat, skin, eye, endoscopic or other imaging (in addition to non-medical imaging). This approach could allow for a more powerful case to work with a variety of simpler, less expensive optical or other sensor attachments, providing a versatile toolkit for mobile image and other data collection.

Figure 3C:
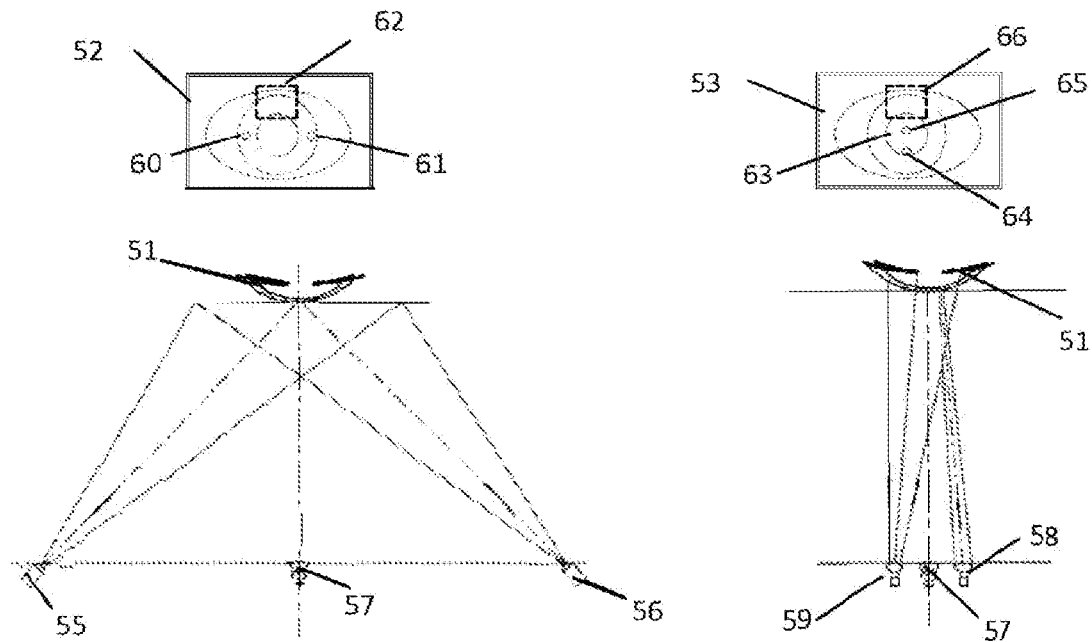
FIGS. 3C-3D show exemplary lighting arrangements for single and dual camera capture systems.

In other embodiments, stereo images can be captured. The light emitting diodes and the light conditioning optics of the lighting units are arranged to project the diverging light with center of their cones converged at the optical axis of the imaging camera 57. In the FIG. 3C, the object 51, which is an eye, is located at the convergent point of lighting and is seen in the center of the picture 52 and 53 taken from the camera 57. The intensity or brightness of the light from the lighting unit 55 and 56 are adjustable, either manually or automatically, and to be seen with same or different brightness in the images of camera 57. Two bright spots 60-61 could be seen in the picture 52 from the spectacular reflection of light off the cornea. The purpose of such optical lighting arrangement is to allow uniform illumination of the object when both lighting unit 55 and 56 are turned on, and to produce high contrast images when only one lighting unit is turned on. The contrast of the images (through the lighting) could be adjusted by the ratio of the light intensity from two lighting units 55 and 56. The default setting could be that of identical brightness for 55 and 56, while the brightness is adjustable collectively. The camera 57 is equipped with a focusing sensor which detects the focus status within a specific area indicated to the users within the live image window. A small color block 62 is shown in the picture 52, which indicates the area of focusing zone. The users could select or change the area of focus by taping the desired area in the window of live images shown the touch screen of the portable computing device. The change in the color of the block could indicate if the object is in focus or not. The camera 57 has two working modes for focusing: manual and autofocus. If the autofocus mode is chosen, the camera, through its focus sensor and optics, would automatically focus on the area of object indicated by the focus area. Because, under the preview of live images, the low resolution displaying device is often used, the status of precise focus have to be determined by the focus sensor and not by the sharpness of the live images. Then the focusing status is indicated in the frame of live pictures with symbol, for example the color of the focus block or audible sound. If the manual focus mode is selected, it is often used to image an object at a predetermined distance. When the optics in the front of camera 57 is factory calibrated to provide a predetermined (fixed) focusing distance for the camera, the users could then move the camera 57 (holding the imaging apparatus) back and forth while using the focus sensor indicator 512 as the guidance. If the focal length of the optics is also fixed, or a lens with fixed focal length is used, then the optical magnification of the imaging system is also fixed in such circumstance. With the help of focus sensor, the optics lens with the fixed focusing distance and the fixed optical focus length would enable the user to take pictures with fixed magnification, which is important if the geometrical measurement is to be taken later from the captured images.

The special optics is used in the front of lighting unit 58 to generate a focused light beam, with its beam waist (narrowest part of the beam or focus of the beam) located at a predetermined distance from the camera 57. For example, when a human eye 51 is located at the predetermined distance, the light beam from the lighting unit 58 is also focused near the area, but at a small distance from the optical axis of the camera 57. The picture 53 presents a separate view seen from the camera 57 when the eye is photographed. The circle 513 in the center of the picture 53 indicates the opening of the iris from an eye. Here, the light beam from the lighting unit 58 is focused and projected into the eye from the edge of the iris opening whose location is indicated by spot 64 in the picture 53. Such arrangement is very useful in providing a special lighting condition, called retroillumination, and allows users to observe cataract in the eye easily.

On other hand, the light from the lighting unit 59 forms a divergent beam and with its axis almost in parallel with the optical axis of the camera 57. The divergence of the light beam ensures that the object within the field of view of the camera 57 is well illuminated. Using the close proximity between the light source 59 and the camera 57, such lighting arrangement allows users to exam objects in narrow space or in the closed cavities. When an eye is photographed in close distance with illumination from the lighting unit 59, it creates a "shadowless" image as shown in the picture 53, where the bright spot 515 represents the spectacular reflection from the cornea. Such lighting condition created by the unit 59 could also be used as the supplementary "background" lighting for photographing cataract in the eye under the retroillumination. Again, the focus indication block 66 is shown in picture 53, which could be used to focus precisely onto the cataract seen in the crystalline lens. In another special application, when a visible or an invisible (IR) light emitter is used in the lighting unit, the facial images of a patient taken at distance from the camera 57 could be used to diagnoses a medical condition called amblyopia. The light from the unit 59 creates a diffused reflection of light from the retina area and then back through the irises of the patients, is often seen as "red eye" in the facial images. If the reflections of light from two eyes are not symmetric as appeared in the irises, it indicates possible eye problem for the patient. Additional potential applications for such imaging system include photographing cavities in the ear, month, and nose of patients.

Mobile devices include sensors such as a gyroscope, accelerometer, ambient light sensor, proximity sensor, noise-cancelling microphone, and others, which could be used to aid in image analysis and comparison. For example, the internal gyroscope and accelerometer readings may be used as image metadata to aid in orientation normalization and image registration. External sensors and hardware features can be added to adapter 10 for image analysis. For example, a dermascope smartphone attachment may use an integrated test pattern, which can be used by the apparatuses to normalize the white balance, color values, and image exposure. Uniformity of exposure (or fidelity of the exposure pattern to an illumination design) can also be captured in an image or added using an additional sensor. For example, an external light meter could be couple with the mobile device using wired or wireless means, or a secondary camera on the device could capture the relevant lighting data. The mobile app could also measure the brightness of the region of interest and manually adjust the LED intensity to compensate (with a fixed exposure time).

While a single camera phone configuration is detailed above, phones with two cameras can be used in order to take the stereoscopic images. The stereoscopic images have the advantage of displaying depth information, and are better in visualizing the transparent medium, like the cornea. The lighting units consist of same lighting elements of lighting unit but the shutters for both cameras of the phone can be opened and closed at same time. Together, cameras generate pictures in the similar fashion as two eyes of human being, when they are focused at same object.

Figure 3D:
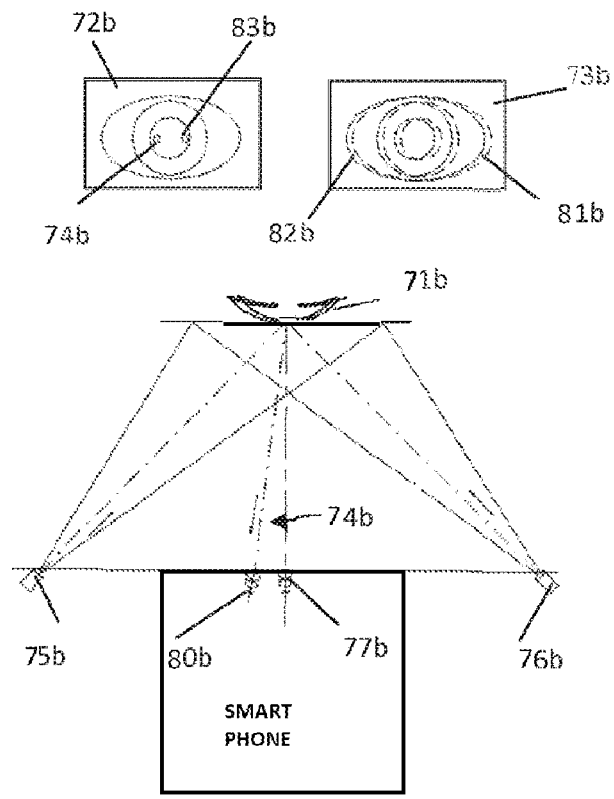

FIG. 3D shows the details of the lighting schematic for the same imaging system. The photographed object 71b, an eye for example, is located near the convergent point of light beams from unit 75b and 76b, as well as at the convergent point of the optical axes of two camera 77b and 80b. The convergent angle 74b, formed by the optical axes of two cameras, could be either fixed or adjustable. In case it is fixed, the distance between the object 71b and the cameras are chosen based on the size of the object in the picture 72b and 73b. Depending on the viewing conditions of the stereoscopic display system, the divergent angle 74b typically could be between 5 to 13 degrees. The image from camera 77, which represented as 81b, and camera 80b, which is represented as 82b, are combined and shown in one display 73b. Because both camera 77b and 80b are focused at the convergent point of their optical axes, if the object, here the eye, is not located exactly at the convergent point, the image 81b and 82b will not overlap to each other, as shown in picture 73b. To get proper stereoscopic images, the users need to move the imaging apparatus back and forth to get the two images coincided, as shown in the picture 72b. In the picture, the two bright spot 83b and 84b represent the spectacular reflections of light from lighting unit 75b and 76b by cornea of patient 71b. When the convergent angle 74b is fixed, the distance at which the two images from camera 77b and 80b are fully overlapped is also predetermined and fixed. Therefore, the use of dual cameras not only could generate the stereoscopic images for review, but also a precise method to set a constant distance, from the object to the cameras. As the result, the images taken at the constant distance also have same optical magnification if the focal length of the imaging optics is fixed. Such feature is important for many medical applications because the geometrical measurement could be taken later from the captured images. Even topographic profiles of the photographed objects could be calculated from the stereoscopic image pairs. It is important to point out that although the focus of the camera 77b and 80b could be pre-fixed at the convergent point of optical axes, the camera could also be set into auto focus mode during such operation.

Figure 4:
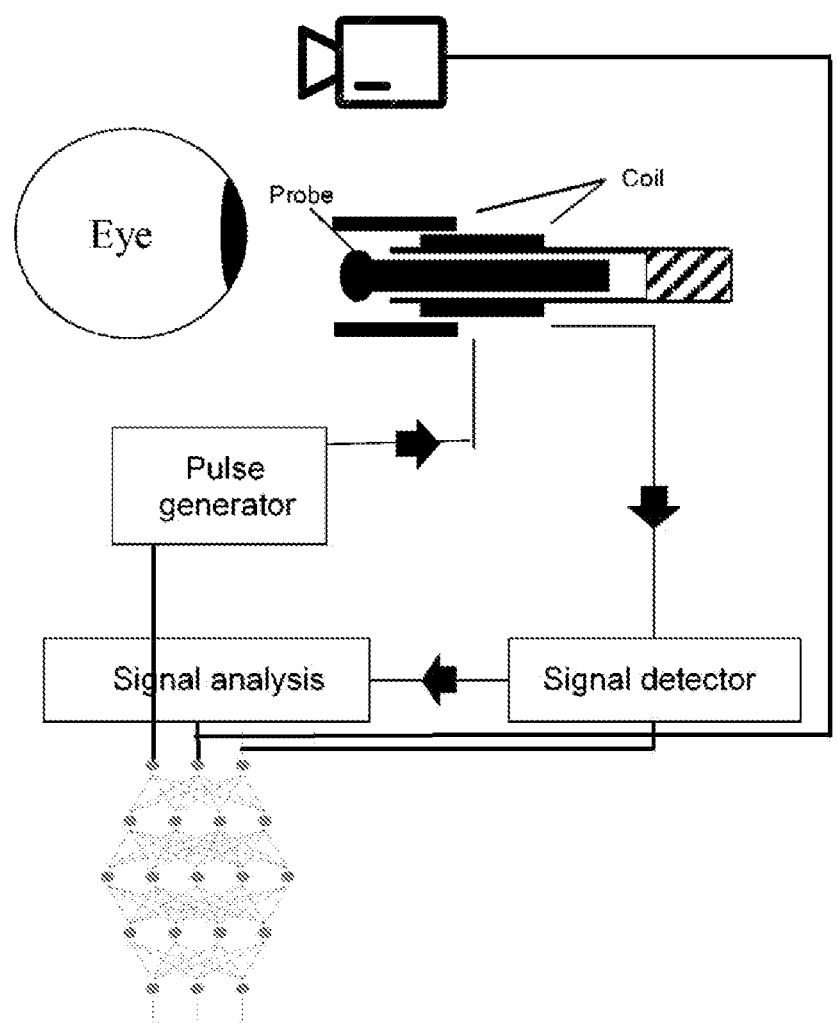
FIG. 4 shows a non-invasive pressure sensing system with deep learning machines.

FIG. 4 shows a non-invasive pressure sensing system. The phone cameras can register corneal curvature changes. The corneal curvature in human eyes correlates well with IOP, in which an IOP change of 1 mmHg causes a change of central corneal radius of curvature of approximately 3 μm. A high correlation exists between the IOP variations and the changes in the corneal curvature measured in the corneoscleral area, where it is believed IOP changes induce maximum corneal deformation. As IOP fluctuates synchronically with heart rate, this 24-hour registration of IOP rhythm can be inspected for ocular pulsation, including systolic and diastolic peaks and ocular pulsation frequency. The deep learning network discussed above is used to predict IOP pressure based on imaged corneal curvature as validated by a tonometer.

The images of the curvature can be correlated using a tonometer of FIG. 4. Briefly, the tonometer consists of a pair of coils coaxial with the probe shaft that are used to propel the lightweight magnetized probe toward the cornea and to sense its movement. Appropriate electronic components allow for the probe movement to be initiated by the solenoid coil and monitored by the sensing coil. An applied pulse of electrical current induces a magnetic field within the solenoid, causing the probe to be propelled onto the cornea from where it rebounds. Motion parameters of the probe can be determined from movement of the magnetic probe, which generates a voltage in the sensing coil that is readily recorded and analyzed. The voltage is proportional to the magnetic field induced, which is proportional to the probe speed. Several motion parameters of the probe can be extracted from the sensing coil oscilloscope record and related to the IOP, such as the time of eye contact, the velocity of return, and the deceleration time. The inverse of deceleration time (deceleration time−1) parameter is most closely correlated to IOP. The probe consists of a magnetized steel wire shaft with a round plastic tip (1 mm diameter) at its front end. This round tip minimizes the possibility of corneal damage from probe impact.

It is preferred that these processing functions be incorporated into the smart-phone's processor. By incorporating these processing functions into a general purpose smart-phone, tablet computer or other mobile communications device with an integral camera system and computing capabilities, the cost of the overall system will be less because of the economies of scale in using modular elements. Additionally, with a general purpose smart-phone, the processing software can be updated as the computing power and storage capacity of these devices continue to increase. Updates to the software may include additional processing functions and additional analyses of the images, such as pattern recognition evaluations and tools, which cannot be efficiently performed on current smart phones. Yet another benefit of the modular nature of the present invention is the increasing resolution and imaging power of smart-phones. The optics of the viewing instruments, such as ophthalmoscopes, may already be optimized, and being able to swap in new smart-phones with better computing and imaging capabilities will continue to improve the overall system without having to replace those elements in the system that are already optimized. This will further reduce the overall operating costs of the system over the lifespan of each component because the user will be able to replace each component individually as it reaches the end of its life rather than replacing the entire system.

According to the ophthalmologic imaging embodiment of the present invention, the interface between the smart-phone and the ophthalmoscope or otoscope (FIG. 3A item 12) includes the data exchange between the two devices. The exchange of data is preferably used to document and add to the patient file as well as to process the internal settings of the phone ophthalmoscope, such as the refractive power used to obtain a clear image. As discussed above, with an ophthalmoscope that has setting controllers for the image control features, the smart-phone can control functions of the ophthalmoscope such as the refractive power setting, light output level color and size, and may even provide a trigger for an increased light level for the purpose of flash photography.

With an analog ophthalmoscope, the focal power of the scope's lens system can be calibrated so that it causes the focusing lens within smart-phone camera (material that changes refraction index as voltage is applied) to use approximately one-half of its focal power to obtain a clear image of an emetropic human eye (i.e., no refractive error in the eye). This configuration would allow the smart-phone camera to automatically add or subtract focal power and enable the clear imaging through a wide range of refractive errors in the lens of the subject's eye (myope and hyperope) with no additional focusing lenses required in the adapter. By calculating the focal power required by the smart-phone's camera system to obtain a clear image, an approximation of refractive power of the subject eye can be determined. It will be appreciated that the scope could also be calibrated with the smart-phone's camera system for several different viewing options, such as a standard field of view through non-dilated pupil and a wider field of view through a dilated pupil. Of course, with the smart-scope, the smart-phone may send signals to the ophthalmoscope to change the refractive power, and in this case the smart-phone would be able to directly calculate the refractive power of the subject eye based on the measured settings from the smart-scope and corresponding optics tables for the smart-scope's lens positions.

It will be appreciated that the present invention for the smart phone ophthalmological imaging system provides non-eye specialists with a method of non-mydriatic or mydriatic fundus photography at an extremely low cost. More generally, for viewing instruments generally, since smart-phones have their own computer processors and displays that can be used to control various functions of the smart-phone, such as the communications module and the camera system, one or more specialized computer applications running on the smart-phones can serve as the control panel for optimizing the use of the smart-phone with a viewing instrument which may be an analog scope or a smart-scope.

As indicated above, the smart-phone can be adjusted for a range of scope settings. For example, with ophthalmoscopes in particular, red filters may be used to decrease the percentage of color spectrum received that is in the red spectrum. This would increase image contrast while imaging the retina, as it is mostly pigmented red. Also, it is often difficult for a clinician to obtain a good view of the retina through an undilated pupil for long periods of time which would typically be required for good photography. This is partially due to low patient tolerance for bright lights and limited ability to hold the ophthalmoscope perfectly steady. The latter half of this problem can be mitigated by the ability of the clinician to look at the live subject images on the smart-phone's display screen rather than having to press their own eyes against the view port of ophthalmoscopes and fundus cameras. With regard to patient tolerance of light, when the smart-phone is used with a smart-scope, the processor could reduce the light intensity while the clinician aligns the device with the portion of fundus that is to be imaged and then increases the intensity when the clinician selects the capture image command. This could allow focusing of the camera lens with better patient tolerance. Of course, with auto-focus capabilities in either a smart-scope ophthalmoscope or in the smart-phone, the time to focus the overall ophthalmologic imaging system could be greatly reduced. The processor can also optimize the use of the particular ophthalmoscope optics with the features of the smart-phone. The mobile device compensates for the eye condition during usage. For example, wearable AR/VR devices can actuate the lens to enable proper focus of the eyes. The lens can be a liquid lens which are mechanically or electrically controlled cells containing optical-grade liquid. When a current or voltage is applied to a liquid lens cell, the shape of the cell changes. This change occurs within milliseconds and causes the optical power, and therefore focal length and WD, to shift. The shape of the lens can be adjusted to provide optical correction for reading, among others. Alternatively, MEMS actuators, VCM, piezo motor, or liquid crystal, for example. A tunable liquid lens can be used, as can a variable focus elastomer liquid lens can be used in the mobile device to provide correctable vision for the user.

The system can provide education and assistance to users to calm the user in case of laser exposure. If the eye spots are still visible after laser exposure, the user may have retinal damage. Fortunately, this often heals within a few days or weeks. The system can provide interface for showing example disease progression via images, for example, a user-facing interface for educating users about the expected progression of a given disease, possibly given an intervention, using example longitudinal imaging data from the database. Vision may return completely to normal, or the patient may have faint spots noticeable only under special conditions such as looking at a uniform white wall or blue sky. The system provides an Amsler Grid test to help in finding small lesions within 8-10 degrees of the fovea. Given a disease name-gleaned for an exam using the automated diagnosis procedure—and possibly an intervention, this interface will show longitudinal imaging from a single patient, with images spaced over time. The user will then have the ability to visually compare their exam to the example progression to estimate their stage in the disease progression. This interface may also be extended to compare a query image to images within an example disease progression in order to automatically line up the query image with the appropriate image in the disease progression. This will visually inform the user of the current stage of their disease. Determination of similarity between the query image and the images in the example progression would be made via the same similarity metrics using an ordinal classifier. This interface would not be confined to any given example progression for a given disease/intervention, but could search for the closest image in all sets of longitudinal progression data associated with the given disease/intervention.

Via methods described herein, it is possible to create a textured 3D model of a patient's eye structures. Alternative methods including using high-resolution CT or MRI images to create the 3D model of the eye may be used; the model could then be textured using textures from any standard ophthalmic exam. Such a 3D model could be used for training or to aid in diagnosis of a real patient. Once a 3D model exists, a user can navigate through the reconstructed eye and view relevant anatomy from different angles. This navigation could be performed on any device (e.g., PC, tablet, mobile phone, heads-up display, such as Google Glass, etc.), and is not limited to the device used to record the original exam. On a PC, navigation could be performed in a manner similar to that of a 3D modeling program, such as SolidWorks, or a 3D exploration program, such as Google Earth. Different combinations of clicking, dragging and mouse wheel scrolling perform functions of view zooming, panning and rotation.

On a mobile device, navigation could be performed in the "Google Earth style," where certain multitouch gestures allow panning, zooming or rotating the view. Alternatively, navigation could make use of the device's built-in accelerometer, so that, as the device moves or rotates, those movements can be captured and translated into corresponding movements of the view within the mobile application, allowing for a "virtual eye exam" using the previously built 3D model. This interface performs similarly to, for example, the Google Sky Map Android app (http://www.google.com/mobile/skymap/). The Google Sky Map app allows the user to point their mobile device at a portion of the sky and shows constellations and other relevant space phenomena in the direction that the device is pointing; the device's orientation is deduced by reading its accelerometer values. In the case of the virtual eye exam, the same principle is used, except that the "virtual space" consists of the textured 3D eye or eye model.

When an individual performs an eye exam for the first time, it may be difficult for them to determine whether they are performing the exam correctly. A properly trained real time guidance system that is integrated with the system helps the user in proper usage through "heads up display"-style cues (e.g., arrows, "locked on" indicator, or other graphics superimposed on the live video of the in-progress exam) or audio cues (e.g., a chime, or a voice instructing the user to move the otoscope left, right, into the ear, out of the ear, etc.) to guide the user during the exam. This would help to ensure that the necessary anatomy is visualized during the exam and that the exam is conducted in as expedient and safe a manner as possible. In addition to or alternatively, a supervised machine learning classifier can be trained to detect proper orientation and guide the user. For example, for ear structures, a region of increasing depth is manually segmented in the videos. The region of increasing depth classifier would then be trained and operated in an analogous manner to that described above for TM segmentation.

For example, described herein are methods and devices for detecting a laser injury on eye fundus. In general, the method may include: receiving the image of the subject's fundus; extracting a set of feature values for subregions of the image; estimating, for each subregion, a probability that the subregion is part of a fundus based on an extracted sets of feature values for the subregion; and identifying a fundus region from the image using the estimated probabilities for the subregions.

In any of the methods described herein, receiving the image may include receiving a video frame (e.g., an image taken from a video). In general, extracting may comprise extracting feature values for each of the subregions in the subset of subregions at a plurality of different scales. Different scales may mean different magnifications, or different filtering levels. For example, a raw image may be processed to provide a different scale by filtering (e.g., blurring, sharpening, etc.) and the resulting processed image may provide an additional scale of the image. For example, extracting may comprise extracting, at the plurality of different scales for each particular subregion within the subset of subregions, the set of feature values comprising a plurality of color space values for: the particular subregion in the subset of subregions, and for a plurality of subregions immediately adjacent to the particular subregion. Any of these methods described herein may also include estimating, for subregions not within the subset of subregions, a probability that subregions not in the subset of subregions is part of a tympanic membrane by interpolating from the probabilities that adjacent subregions within the subset of subregions are part of the fundus.

Any appropriate features may be extracted. For example, features may include color features (color space, such as RGB, HSL/HSV, CMYK, and lab color space, e.g., CIELAB). For example, extracting a plurality of features for each of the subregions in the subset of subregions may comprise extracting color space information for each subregion in the subset of subregions. Color space information may refer to color information for the image from a particular color space, such as CIELAB. Thus, only a portion of the color space information (one or more intensity, hue, saturation, lightness, etc.) may be used. Features may include statistical mappings or transformations of the raw color information, such as averages, distributions, standard deviations, etc. For example, extracting a plurality of features for each of the subregions in the subset of subregions may comprise extracting a color lightness value, a first hue value and a second hue value for each subregion in the subset of subregions. Extracting a plurality of features for each of the subregions in the subset of subregions may comprise extracting a color hue value, a color saturation value and a color brightness value for each subregion in the subset of subregions.

In general, identifying the fundus region may include any appropriate identification, including visual (e.g., identifying a tympanic membrane region from the image on a representation of the image by circling/outlining, highlighting, coloring, etc.), audible, indicating that the image includes such a region, or setting one or more registers associated with an image to indicate that the image includes a fundus, or portion of an eye fundus (e.g., above a threshold minimum amount of eye fundus region). A separate image including just the extracted eye fundus may be generated.

For example, an apparatus may also include an eye adapter (lens portion) to connected to a mobile device or smart phone and a non-transitory computer-readable storage medium storing a set of instructions capable of being executed by a processor, that when executed by the processor causes the processor to: receive an image of the subject's eye; select a subset of subregions from the image; extract, at a plurality of different scales, a set of feature values for each of the subregions in the subset of subregions; estimate, for each individual subregion within the subset of subregions, a probability that the individual subregion is part of an eye fundus based on the extracted sets of feature values for the individual subregion; and identify, on a representation of the image, an eye fundus region from the image using the estimated probabilities for the subregions within the subset of subregions.

Thus, described herein are non-transitory computer-readable storage medium storing a set of instructions capable of being executed by a processor, that when executed by the processor causes the processor to: receive an image of the subject's eye; select a subset of subregions from the image; extract, at a plurality of different scales, a set of feature values for each of the subregions in the subset of subregions; estimate, for each individual subregion within the subset of subregions, a probability that the individual subregion is part of an eye fundus based on the extracted sets of feature values for the individual subregion; and identify, on a representation of the image, an eye fundus region from the image using the estimated probabilities for the subregions within the subset of subregions.

Any of the methods and devices for identifying an eye fundus region (or portion of an eye fundus region) described herein may be configured or adapted for use as part of a method or device for displaying, matching, identifying, diagnosing, guiding a subject to acquire and image or, or otherwise examining a image or video including the determination of an eye fundus region.

Also described herein are methods and devices for guiding a subject to assist in taking an image a patient's eye fundus. In general, it may be difficult for a novice (or an untrained individual, such as a patient, parent or non-specialist) to image the eye fundus, and in particular to capture a sufficiently detailed image of an eye fundus for use in diagnosing or analysis using the eye fundus. Described herein are methods and device for aiding in imaging the eye fundus that may be used, in particular, for use with a home or clinical device that includes a camera (e.g., speculum, lens/lenses, and video/image capture capability). Images may be acquired until the method/apparatus indicates, e.g., visually or audibly, that an adequate image has been taken. The image(s) may then be stored, transmitted, and/or analyzed. For example, stored images may be transmitted to a medical provider for further analysis, or to a third-party analysis center.

For example, a method of guiding a subject using an ophthalmic diagnostic device coupled to a display device to image an eye fundus may include: displaying, on the display device, an image from the camera; detecting at least a portion of an eye fundus from an image of a subject's eye; indicating to the subject when an image of at least a portion of the eye fundus has been taken.

In general, a method of guidance or an apparatus for guiding a subject to take an image may examine images (digital images) of a patient's eye being taken by the user, e.g., operating a camera to determine when a minimum amount of eye fundus is showing (e.g., more than 20%, more than 25%, more than 30%, more than 35%, more than 40%, more than 45%, more than 50%, more than 55%, more than 60%, more than 65%, more than 70%, more than 75%, more than 80%, more than 85%, more than 90%, more than 95%, etc.) in the image. This may be done, as mentioned above. The method or apparatus may then indicate that an adequate image has been taken, and/or may automatically start sending, transmitting, and/or analyzing the image(s).

As mentioned above, detecting at least a portion of the eye fundus from the image may comprise: extracting a set of feature values for each of a plurality of subregions from the image; estimating, for each individual subregion within the plurality of subregions, a probability that the individual subregion is part of an eye fundus based on the extracted sets of feature values for the individual subregion.

Any of the methods and apparatuses described herein may be performed on/by a mobile device or smart phone, such as a smartphone (iPhone, Android, etc.), pad/tablet (iPad, etc.), laptop, and mobile computing device (e.g., Google Glass, iWatch, retina implant, etc.). For example, displaying one or more images on the display device may comprise displaying on a mobile device or smart phone. Thus, any of the steps of the methods described herein may be performed by the mobile device or smart phone (e.g., smartphone), including on the display and/or processor of the mobile device or smart phone. Some of the steps (or in some variations, all of the steps) may be performed remotely, e.g., by a processor to which the mobile device or smart phone is communicating. In general, as described herein a mobile device or smart phone includes any device that is portable, includes a processor and is configured to communicate with a network such as the internet and/or a telephony network, including, but not limited to smartphones (iPhone, Android, etc.), pads/tablets (iPad, etc.), laptops, and wearable computing devices (e.g., Google Glass, iWatch, retina implant, etc.)

In some variation a method or system may alternatively or additional guide a subject by providing one or more directions, including directions on a display screen showing the images, audible cues, textual cues or the like, so that the subject may move the camera device to adjust the view being taken. In addition, the method or system may indicate when the image is obstructed (e.g., by wax, foreign body, etc.) and/or when the image quality is low (poor lighting, focus/lensing issues, etc.).

A method of guiding a subject using a camera coupled to a display device to image an eye fundus may include: displaying, on the display device, an image from the camera; detecting one or more deeper regions in the image from the camera; indicating to the subject, a direction to orient the camera based on the detected one or more deeper regions; and indicating to the subject when an image of at least a portion of the eye fundus has been taken.

A method of guiding a subject using a camera coupled to a display device to image an eye fundus may include: taking an image of an eye using the camera; displaying, on the display device, the image; detecting one or more deeper regions in the image from the camera; indicating if the eye is occluded; indicating on the display device, a direction to orient the camera based on the detected one or more deeper regions; and indicating when an image of the eye fundus has been taken.

A method of guiding a subject using a camera coupled to a display device to image a patient's eye fundus, the method comprising: displaying, on the display device, an image of the subject's eye from the camera; detecting one or more deeper regions in the image: correcting for uneven illumination in the image, identifying one or more regions of brightness below a threshold in the image, extracting features for each identified region, and determining if an identified region is deeper in the eye based on the extracted features; indicating a direction to orient the camera based on the detected one or more deeper regions; determining if the image includes an eye fundus by: extracting a set of feature values from a plurality of subregions from the image, estimating, for each subregion, a probability that the subregion is part of an eye fundus based on the extracted sets of feature values; and indicating when an image of the eye fundus has been taken.

As mentioned, any of these methods may include detecting at least a portion of an eye fundus from an image of a subject's eye and indicating to the subject when an image of at least a portion of the eye fundus has been taken. The indicator may be visual, audible, or both. For example, an indicator may be a beep, tone, song, etc., indicating that an adequate image has been taken. In some variations the indicator includes a flash, highlight, signal, text message, or the like, which may be displayed on the screen (e.g., of the display device, e.g., smartphone screen).

Any of these methods and apparatuses may also indicate an occlusion of an eye from the image, including automatically detecting when the eye is occluded. Additionally, any of these methods and apparatuses may also include instructing the subject to straighten the eye. Instructions may be visual (images, text, etc.) or audible, or both. In general, any of these apparatuses and methods may be configured to automatically detect when it is helpful or necessary for the subject to reposition and/or view adjustment to straighten the eye. The method of device may include providing an indicator when the eye has been straightened sufficiently. Thus, instructing the subject to straighten the eye includes automatically instructing the subject to straighten the eye.

In some variations, detecting one or more deeper regions comprises: determining a field of view for the image, correcting for uneven illumination in the field of view, identifying from the field of view one or more regions of brightness below a threshold in the image, extracting features for each identified region, and determining if an identified region is deeper in the eye based on the extracted features. Alternatively or additionally, detecting one or more deeper regions may comprise: determining a field of view for the image, converting the field of view of the image to greyscale, filtering the field of view of the image to remove small objects, and dividing the image by an average illumination value.

Detecting one or more deeper regions may comprises: determining a relative distribution of pixel values from the image from the camera and identifying regions having the relative distribution of pixel values below a threshold value. Detecting one or more deeper regions comprises may include using a trained model to determine if the one or more regions are deeper regions in an eye. In some variations, detecting one or more deeper regions comprises extracting features from one or more regions of the image that are not as bright as other regions and using a trained model to determine if the one or more regions are deeper regions in an eye, wherein the extracted features include one or more of: region area, region eccentricity, region solidity, mean intensity of the region, and mean intensity of the region in an illumination-corrected image.

As mentioned, any of these methods may include determining if the image includes an eye fundus. For example, by extracting a set of feature values from a plurality of subregions from the image, estimating, for each subregion, a probability that the subregion is part of an eye fundus based on the extracted sets of feature values.

Also described herein are apparatuses configured to guide a subject to capture fundus images. For example, a system may include a non-transitory computer-readable storage medium storing a set of instructions capable of being executed by a processor, that when executed by the processor, causes the processor to: display an image from a phone camera; detect one or more deeper regions in the image from the camera; indicate to a subject a direction to orient the camera based on the detected one or more deeper regions; and indicate to the subject when an image of the eye fundus has been taken. Any of these systems may also include the camera (e.g., lens, speculum, etc.) and display device (e.g., smartphone or other mobile device or smart phone). The system may be configured to couple to the display device, including coupling to a built-in camera on the display device and supplement any lenses on the built-in camera to convert it to a lens to capture medical data from the user.

In general, also described herein are methods and devices for displaying an eye fundus. These methods may generally be performed on images collected and analyzed as described above, though they may be used/performed independently of these.

For example, a method of displaying an image of an eye fundus may include: displaying a first image of a subject's eye fundus; identifying a plurality of similar eye fundus images from a database of eye fundus images including images of the same eye fundus taken at different times, based on color and texture values of the first image; concurrently displaying the first image and the plurality of similar eye fundus images. The method of displaying an image of an eye fundus may further include: extracting a plurality of image features from a first image of a subject's eye fundus, wherein the image features include color and texture data; combining the extracted features into a feature vector for the first image; identifying a plurality of similar eye fundus images from a database of eye fundus images by comparing the feature vector for the first image to feature vectors for images in the database of eye fundus images; displaying (e.g., concurrently) the first image and the plurality of similar eye fundus images and indicating the similarity of each of the similar eye fundus images to the first image.

Another method of displaying an image of an eye fundus may include: selecting a region of interest from a first image including an eye fundus; extracting a plurality of image features from the region of interest of the first image, wherein the image features include color and texture data; combining the extracted features into a feature vector for the first image; identifying a plurality of similar eye fundus images from a database of eye fundus images by determining the distance between the feature vector for the first image and feature vectors for images in the database of eye fundus images, and selecting images from the database of eye fundus that are closest based on the determined distance; displaying the first image and the plurality of similar eye fundus images and indicating the similarity of each of the similar eye fundus images to the first image.

Extracting a plurality of image features from the first image may include extracting image features comprising color and texture data from the first image and wherein identifying the plurality of similar eye fundus images comprises using the extracted image features to identify the plurality of similar eye fundus images.

Any of these methods may also include allowing a user to select one of the plurality of similar eye fundus images and displaying time course images of the selected eye fundus image. In addition or alternatively, any of these methods or apparatuses may be configured to display a diagnosis associated with one or more of the plurality of similar eye fundus images. In general, the methods and apparatuses described herein may communicate with a dataset of images (e.g., eye fundus images) that includes associated information, which may include diagnosis information, associated symptom information (e.g., fever, headache, ear pain, etc.). For example, the subject/user may be allowed to select one of the plurality of similar eye fundus images and displaying time course images of the selected eye fundus image.

As mentioned, any of these devices and apparatuses may be configured to use a smartphone or the like. For example, displaying the first image and the plurality of similar eye fundus images may comprise displaying on a mobile device or smart phone.

Any of the methods for displaying the image of the eye fundus may include reducing the dimensionality of the feature vector to form a reduced feature vector and identifying the plurality of similar eye fundus images using the reduced feature vector.

In general, identifying the plurality of similar eye fundus images from the database of eye fundus images may comprise determining the distance between the feature vector for the first image and feature vectors for images in the database of eye fundus images, and selecting images from the database of eye fundus images that are near.

Any of these methods may also include transforming a color space of a first image of a subject's eye fundus into a uniform color space (e.g., CIELAB, etc.). For example, any of these methods may include transforming the first image into a perceptually uniform color space.

An apparatus for displaying an image of an eye fundus may include non-transitory computer-readable storage medium storing a set of instructions capable of being executed by a processor such as a smartphone, that when executed by the processor (e.g., smartphone), causes it to: display a first image of a subject's eye fundus from a camera; identify a plurality of similar eye fundus images from a database of eye fundus images including images of the same eye fundus taken at different times, based on color and texture values of the first image; concurrently display the first image and the plurality of similar eye fundus images.

Also described herein are methods and apparatuses to assist in diagnosis. For example, described herein are methods of guiding diagnosis of an eye ailment using an image, the method comprising: extracting a plurality of image features from a first image of a subject's eye fundus, wherein the image features include color and texture data; combining the extracted features into a feature vector for the first image; applying the feature vector to a trained classification model to identify a probability of each of a plurality of different diseases; indicating the probability of each of a plurality different diseases.

A method of guiding diagnosis of an eye ailment using an image of a subject's eye fundus may include: selecting a region of interest comprising at least a portion of the subject's eye fundus from a first image including at least a portion of an eye fundus; extracting a plurality of image features from the region of interest of the first image, wherein the image features include data derived from the color and texture data; combining the extracted features into a feature vector for the first image; applying the feature vector to a trained classification model to identify a probability of each of a plurality of different diseases; indicating the probability of each of a plurality different diseases and displaying an image of an exemplary eye fundus for each of the plurality of different diseases.

Any of these methods may include reducing the dimensionality of the feature vector to form a reduced feature vector and applying the feature vector to the trained classification model comprises using the reduced feature vector.

As mentioned above, any of these methods and apparatuses may be configured to work on/with a mobile device or smart phone such as a smartphone. Thus, any of the steps may be performed on the mobile device or smart phone. For example, extracting may comprise extracting on a mobile device or smart phone.

Any of these methods may include selecting a region of interest including at least a portion of the eye fundus.

In some variations, the methods may include transforming the first image into a perceptually uniform color space (e.g., CIELAB) before extracting the image features. In general, extracting image features may include extracting color data comprising a mean of an image color channel within a region of interest.

There are many kinds of image features that may be extracted, however, color and texture image features (including "derived" color and texture features as described herein) have been found herein to be particularly useful. For example, extracting image features may include extracting color data comprising a median of an image color channel within a region of interest. Extracting image features may comprise extracting texture data comprising one or more of: energy, correlation and homogeneity of the eye fundus in one or more color channels. Extracting image features may comprise extracting texture data comprising one or more of: energy, correlation and homogeneity of the eye fundus in one or more of an L, A and B channel of the first image transformed to a CIELAB image. Extracting image features may comprise extracting a mean of all the standard deviations within one or more sub-regions of the first image from channel A and B of a CIELAB transformation of the first image. Extracting image features may comprise extracting a variance of all the standard deviations within one or more sub-regions of the eye fundus in channel A and B of a CIELAB transformation of the first image. Extracting image features may comprise extracting a normalized histogram of one or more values of channels L, A and B of a CIELAB transformation of the first image. Extracting image features may comprise extracting a ratio of a square of the mean value of at least a portion of the subject's eye fundus from the first image by a square root of a contrast texture value of at least the portion of the subject's eye fundus in the first image of channels A and B of a CIELAB transformation of the first image. Extracting image features may comprise extracting a ratio of square of the variance of a plurality of standard deviations within one or more sub-regions of at least a portion of the subject's eye fundus from the first image by a square root of an energy texture value in at least the portion of the subject's eye fundus in the first image of channels A and B of a CIELAB transformation of the first image. Extracting image features may comprise extracting a product of a mean value of at least a portion of the subject's eye fundus from the first image and a correlation texture value of at least the subject's eye fundus from the first image of channels A and B of a CIELAB transformation of the first image.

Color and textural features that may be extracted from an eye fundus may include extraction of color features such as the average color hue value or a range of percentiles of color hue value of an eye fundus. Examples of specific color features that may be extracted include the average color value (hue) of eye fundus, and zero or more percentiles of color of eye fundus. Extracted texture features may be those features which characterize the degree of uniformity, coarseness or smoothness within an eye fundus image at a pixel level comparative scale. An example of such an extracted texture feature is average contrast value of an eye fundus, where contrast value is a measure of the intensity contrast between a pixel and its neighbor over the whole image. Another example is an average energy value of an eye fundus, wherein energy value is a measure of the degree of "uniformity" in an image. Another example is an average correlation value of an eye fundus, where correlation value is a measure of how correlated a pixel is to its neighbor over the whole image. Yet another example is average homogeneity value of an eye fundus, where homogeneity value is a measure of how evenly (or not evenly) intensity values are distributed over the entire image. Each of these examples may be mathematically defined as known in the art.

Texture features may also be extracted as one or more levels that are greater than the pixel level comparative scale (in which the smallest units of comparison are aggregated pixels, or sub-regions, typically adjacent to each other). For example, extracted texture features may include features which characterizes the degree of uniformity, coarseness or smoothness within an eye fundus image at a sub-region level comparative scale. An example of such a feature includes: average of standard deviations of sub-regions of an eye fundus, which indicates a measure of the degree of "coarseness" or "fineness" of an image. Each sub-region may have a different degree of "coarseness" or "fineness" and these localized textural differences can be captured and averaged using this feature. Another example includes a variance of standard deviations of sub-regions of an eye fundus, which indicates a measure of a variation of "coarseness" or "fineness" of an image. Each sub-region may have a different variation of "coarseness" or "fineness" and these localized textural differences can be captured in each sub-region and its variation across the image can be quantified using this feature.

Color and textural features that may be extracted include combined color and textural features. Extracted color and textural features (combined color and texture features) may characterizes the effect of image smoothness or coarseness for a certain color hue of the eye fundus at a pixel level comparative scale. An example of this type of feature includes a ratio of color value by contrast value of an eye fundus, which may provide increased separability of high hue-high contrast from low-hue low contrast eye fundus images. Another example is the ratio of color value and correlation value of an eye fundus, which may provide increased separability of high hue-low correlation from low-hue high correlation eye fundus images.

Combined color and texture features that may be extracted including extracted combined color and texture features that characterize the effect of image smoothness or coarseness for a certain color hue of the eye fundus at a sub-region level comparative scale. For example, a combined color and texture feature includes a ratio of variance of all the standard deviations by the energy value of sub-regions of an eye fundus, which may provide an increased separability of high hue-high coarse from low-hue low coarse eye fundus images.

In general, also described herein are methods and apparatuses that are configured to detect when a lens adapter is connected to the device, and particularly to a mobile device or smart phone such as a smartphone. For example, a method of detecting if a lens device is attached to a mobile device or smart phone having a digital camera may include: taking an image using the digital camera of the mobile device or smart phone; comparing an average value for each of a plurality of clusters of pixels at a plurality of regions from the image to a first threshold value; indicating that the lens device is attached when the average values of each of the clusters of pixels in the plurality of clusters of pixels are lower than the first threshold value.

A method of detecting if a lens device is attached to a digital camera device may include: taking an image using the digital camera device; comparing an average value of a first plurality of pixels at a first corner region of the image to a first threshold value; comparing an average value of a second plurality of pixels at a second corner region of the image to the first threshold value; comparing an average value of a third plurality of pixels at a central region of the image to a second threshold value when the average values of the first and second plurality of pixels are both lower than the first threshold value; and indicating that the lens device is attached when the average values of the first and second plurality of pixels are both lower than the first threshold value and the average value of the third plurality of pixels is higher than the second threshold value.

A method of detecting if a selected lens device is attached to a mobile device having a digital camera may include: taking an image using the digital camera of the mobile device; comparing an average value for each of a plurality of clusters of pixels at a plurality of corner regions of the image to a first threshold value; comparing the average value of a central cluster of pixels at a central region of the image to a second threshold value; indicating that the lens device is attached when the average values of each of the clusters of pixels in the plurality of clusters of pixels are lower than the first threshold value and wherein the average value of the central cluster of pixels is higher than the second threshold value; and beginning a medical recording session when the lens device is indicated as attached.

The lens device may be a camera configured to be inserted into a subject's ear. The camera device may be a mobile device or smart phone (e.g., smartphone) having a built-in camera, as mentioned above.

Comparing the average value may comprise comparing an average color RGB color values to the first threshold value. The first threshold value may be a value indicating a dark region. Once the lens is detected and indicated to be attached, the device may proceed to operate, for example, turning on a light source if the lens device is indicated as attached.

Any of these methods may also include comparing an average value of a fourth plurality of pixels at a third corner region of the image to the first threshold value, and indicating that the lens device is attached when the average values of the first, second and fourth plurality of pixels are all lower than the first threshold value and the average value of the third plurality of pixels is higher than the second threshold value. Any of these methods may also include detecting one or more markings in the image identifying the lens device.

For the purpose of understanding the present invention, references are made in the text to exemplary embodiments of an ophthalmoscope and a telescope. It should be understood that no limitations on the scope of the invention are intended by describing these exemplary embodiments. The adapter of the present invention can connect any image capture device to a viewing instrument using any attachment means that has a single bracket with a frame that holds the image capture device securely in place, and the same bracket has an eyepiece section and a body section which respectively connect the lens of the image capture device proximate to the view port section of the viewing instrument and the a distal portion of the image capture device to another section of the viewing instrument, such as a handle or support. The adapter aligns the image capture device's camera lens, preferably a high-resolution camera system, with the optical axis of the viewing instrument. With the image capture device mated to the viewing instrument with the adapter, a processor that is preferably in the image capture device can be used to display control panels and preview screens, receive information from the user or a smart-scope and perform a number of processing tasks that improve the overall imaging system. For the ophthalmological imaging embodiment, the adapter securely aligns the optical axis of the ophthalmoscope and the smart-phone in the x-axis, the y-axis and the z-axis.

Any of the apparatuses and methods described herein may be systems and methods for diagnostic imaging. These systems and methods for image or video capture and analysis may be adapted for use with a mobile device. The examples described herein may be mainly used with a mobile phone (e.g., smartphone), with an attachable imaging lens (attachment) as described above, but they could also take the form of an integrated, stand-alone device. A system may include multiple attachments (components) forming a modular system, or the like. In general, the apparatuses and methods described herein may address the challenges of imaging with a mobile device, including illumination, calibration, and normalization of the data collected, as well as practical issues such as ease of manufacturing. In addition to the examples of otoscopes and derma scopes described herein, other imaging applications may be included, such as an endoscope, laryngoscope, ophthalmoscope, general microscope, as well as multi-function or modular devices which can serve several imaging and/or other data collection purposes.

While eye checking is detailed above through capturing an eye image using a mobile device camera; extracting features of the eye; applying a deep learning neural network to detect potential eye damage; the system can handle nose, throat and ear issues.

In one aspect, a method to inspect a nose includes capturing a nose image using a mobile device camera; extracting features of the nose; applying a deep learning neural network to detect potential nose damage; and reporting the potential damage for treatment. The sytem checks the nasal septum is pink, in the midline, and intact. Red and swollen mucosa, which suggests acute allergic rhinitis; Pale and boggy mucosa, which suggests chronic allergy; and Red and dry mucosa, which suggests decongestant use or anticholinergic effect. The phone camera transilluminates the nasal septum to look for perforations. Shine the light on one side of the septum and look at the other side. Light shining through suggests a septal perforation. Common causes of septal perforations include nose picking, infection, syphilis, tuberculosis, collagen vascular disease, Wegener's granulomatosis, systemic lupus erythematosus, rheumatoid arthritis, exposure to toxins, previous cocaine use, and chromium poisoning. The system looks for nasal septal deformities. Deformities of the vomer ("plowshare"), the unpaired flat bone that forms the inferior and posterior part of the nasal septum, are common after vaginal deliveries. The inferior and middle turbinates and the middle meatus between them should be pink, intact, smooth, and moist. The area should be free of foreign body(s). Note any masses and any deviations from normal, such as a red, pale, or bluish-gray color, bogginess, dryness, fissures, crusts, exudate, edema, polyps, ulcers, watery discharge (rhinorrhea), mucopurulent discharge, or bloody discharge. Drainage and polyps are abnormal. Polyps are usually nontender and a sign of allergy. Consider aspirin sensitivity if the patient also has asthma. Purulent mucus suggests upper respiratory infection or sinusitis. Bloody discharge suggests local trauma or a platelet abnormality. Pulsation of the nasal arteries in the mucus membrane is increased in thoracic aortic aneurysm (Bozzolo's sign). Clear nasal discharge most commonly suggests allergic rhinitis or viral infection. Purulent discharge suggests bacterial infection.

In a further aspect, a method to inspect an ear includes capturing an ear image (including membranes such as tympanic membranes) using a mobile device camera; extracting features of the ear; applying a deep learning neural network to detect potential ear damage; and reporting the potential ear damage for treatment. More on the ear inspection is detailed in U.S. Pat. No. 9,445,713.

In another aspect, a method to inspect a throat includes capturing a throat image using a mobile device camera; extracting features of the throat; applying a deep learning neural network to detect potential throat problems; and reporting the potential throat damage for treatment. The network inspects the lips, oral mucosa and gums: Evaluate the lips, determine color and moisture level. Scaliness or cracking may be indicative of pathology; Evaluate the oral mucosa for ulcers, color changes or nodules. Capture the color of the normally pink gums, recognizing that in people of color, brown patches may be normal. Evaluate the dentition and note the presence of gum erythema or edema suggestive of gingivitis. The system inspects the color and shape of the hard and soft palates. Normal mucosa is pink with a ridged hard palate. Torus palatinus may be present, and is a variation of normal. The tongue is inspected for symmetry. The normal architecture of the tongue includes papillae that get bigger toward the rear of the tongue. Inspect the top, sides and undersurface of the tongue, noting any color variation, ulcerations or nodular lesions. With the patient's mouth open, ask the patient to say, "ahh." In a patient with an intact 10th cranial nerve, this action should raise the soft palate enabling full visualization of the pharynx. If this does not allow visualization, use a tongue blade to depress the tongue. Inspect the tonsilar pillars, tonsils if present, uvula and pharynx. Evaluate for color, symmetry, exudate and enlargement.

One aspect of the body sensor optically measures physiological parameters related to blood constituents by transmitting multiple wavelengths of light and receiving the light after attenuation by pulsatile blood flow within the eye. Advanced physiological monitoring systems may incorporate pulse oximetry in addition to advanced features for the calculation and display of other blood parameters, such as carboxyhemoglobin (HbCO), methemoglobin (HbMet) and total hemoglobin (Hbt), as a few examples. In other embodiments, the device has physiological monitors and corresponding multiple wavelength optical sensors capable of measuring parameters in addition to SpO2, such as HbCO, HbMet and Hbt are described in at least U.S. patent application Ser. No. 12/056,179, filed Mar. 26, 2008, titled Multiple Wavelength Optical Sensor and U.S. patent application Ser. No. 11/366,208, filed Mar. 1, 2006, titled Noninvasive Multi-Parameter Patient Monitor, both incorporated by reference herein. Further, noninvasive blood parameter monitors and corresponding multiple wavelength optical sensors to sense SpO2, pulse rate, perfusion index (PI), signal quality (SiQ), pulse variability index (PVI), HbCO and HbMet among other parameters. Heart pulse can be detected by measuring the dilation and constriction of tiny blood vessels in the ear canal. In one embodiment, the dilation measurement is done optically and in another embodiment, a micromechanical MEMS sensor is used. ECG sensor can be used where the electrode can detect a full and clinically valid electrocardiogram, which records the electrical activity of the heart. The device can detect heart rate (HR) as a biomarker in heart failure (1F) both of diagnostic and prognostic values. HR is a determinant of myocardial oxygen demand, coronary blood flow, and myocardial performance and is central to the adaptation of cardiac output to metabolic needs. Increased HR can predict adverse outcome in the general population and in patients with chronic HF. Part of the ability of HR to predict risk is related to the forces driving it, namely, neurohormonal activation. HR relates to emotional arousal and reflects both sympathetic and parasympathetic nervous system activity. When measured at rest, HR relates to autonomic activity during a relaxing condition. HR reactivity is expressed as a change from resting or baseline that results after exposure to stimuli. These stress-regulating mechanisms prepare the body for fight or flight responses, and as such can explain individual differences to psychopathology. Thus, the device monitors HR as a biomarker of both diagnostic and prognostic values. The HR output can be used to analyze heart-rate variability (HRV) (the time differences between one beat and the next) and HRV can be used to indicate the potential health benefits of food items. Reduced HRV is associated with the development of numerous conditions for example, diabetes, cardiovascular disease, inflammation, obesity and psychiatric disorders. Aspects of diet that are viewed as undesirable, for example high intakes of saturated or trans-fat and high glycaemic carbohydrates, have been found to reduce HRV. The consistent relationship between HRV, health and morbidity allows the system to use HRV as a biomarker when considering the influence of diet on mental and physical health. Further HRV can be used as a biomarker for aging. HRV can also act as biomarkers for:

Overtraining: "Cumulative or too intensive sporting activity (e.g. competition series, overtraining syndrome), however, brings about a decrease in HRV"

Physical Fitness: "People who have an active lifestyle and maintain a good or high level of physical fitness or above-average sporting activity can achieve an increase in their basic parasympathetic activity and thus an increase in their HRV."

Overweight: "an elevated body weight or elevated free-fat mass57 correlates with a decrease in HRV. Both active and passive smoking lead to an increase in HRV"

Alcohol Abuse: "Regular chronic alcohol abuse above the alcohol quantity of a standard drink for women or two standard drinks for men reduces HRV, while moderate alcohol consumption up to these quantities does not change the HRV and is not associated with an increase"

Smoking: "Both active and passive smoking lead to an increase in HRV"

Sleep: Another important factor that affects your HRV score is the amount and quality of sleep.

In one embodiment, the system determines a dynamical marker of sino-atrial instability, termed heart rate fragmentation (HRF) and is used a dynamical biomarker of adverse cardiovascular events (CVEs). In healthy adults at rest and during sleep, the highest frequency at which the sino-atrial node (SAN) rate fluctuates varies between ~0.15 and 0.40 Hz. These oscillations, referred to as respiratory sinus arrhythmia, are due to vagally-mediated coupling between the SAN and breathing. However, not all fluctuations in heart rate (HR) at or above the respiratory frequency are attributable to vagal tone modulation. Under pathologic conditions, an increased density of reversals in HR acceleration sign, not consistent with short-term parasympathetic control, can be observed.

The system captures ECG data as biomarkers for cardiac diseases such as myocardial infarction, cardiomyopathy, atrioventricular bundle branch block, and rhythm disorders. The ECG data is cleaned up, and the system extracts features by taking quantiles of the distributions of measures on ECGs, while commonly used characterizing feature is the mean. The system applies commonly used measurement variables on ECGs without preselection and use dimension reduction methods to identify biomarkers, which is useful when the number of input variables is large and no prior information is available on which ones are more important. Three frequently used classifiers are used on all features and to dimension-reduced features by PCA. The three methods are from classical to modern: stepwise discriminant analysis (SDA), SVM, and LASSO logistic regression.

In one embodiment, four types of features are considered as input variables for classification: T wave type, time span measurements, amplitude measurements, and the slopes of waveforms for features such as (1) T Wave Type. The ECGPUWAVE function labels 6 types of T waves for each beat: Normal, Inverted, Positive Monophasic, Negative Monophasic, Biphasic Negative-Positive, and Biphasic Positive-Negative based on the T wave morphology. This is the only categorical variable considered.

(2) Time Span Measurements. Six commonly used time span measurements are considered: the length of the RR interval, PR interval, QT interval, P wave, QRS wave, and T wave.

(3) Amplitude Measurements. The amplitudes of P wave, R-peak, and T wave are used as input variables. To measure the P wave amplitude, we first estimate the baseline by taking the mean of the values in the PR segment, ST segment, and TP segment (from the end of the T wave to the start of the P wave of the next heartbeat), then subtract the maximum and minimum values of the P wave by the estimated baseline, and take the one with a bigger absolute value as the amplitude of P wave. Other amplitude measurements are obtained similarly.

(4) The Slopes of Waveforms. The slopes of waveforms are also considered to measure the dynamic features of a heartbeat. Each heartbeat is split into nine segments and the slope of the waveform in each segment is estimated by simple linear regression.

The device can include EEG sensors that communicate with the smart phone through Bluetooth. The EEG sensors measure a variety of EEG responses—alpha rhythm, ASSR, SSVEP and VEP—as well as multiple mechanical signals associated with cardiac activity, speech and breathing. EEG sensors can be used where electrodes provide low contact impedance with the skin over a prolonged period of time. A low impedance stretchable fabric is used as electrodes. The system captures various EEG paradigms: ASSR, steady-state visual evoked potential (SSVEP), transient response to visual stimulus (VEP), and alpha rhythm. The EEG sensors can predict and assess the fatigue based on the neural activity in the alpha band which is usually associated with the state of wakeful relaxation and manifests itself in the EEG oscillations in the 8-12 Hz frequency range, centered around 10 Hz. The loss of alpha rhythm is also one of the key features used by clinicians to define the onset of sleep. A mechanical transducer (electret condenser microphone) within its multimodal electro-mechanical sensor, which can be used as a reference for single-channel digital denoising of physiological signals such as jaw clenching and for removing real-world motion artifacts from ear-EEG. In one embodiment, a microphone at the tip of the earpiece facing towards the eardrum can directly capture acoustic energy traveling from the vocal chords via auditory tube to the ear canal. The output of such a microphone would be expected to provide better speech quality than the sealed microphone within the multimodal sensor.

The system can detect auditory steady-state response (ASSR) as a biomarker a type of ERP which can test the integrity of auditory pathways and the capacity of these pathways to generate synchronous activity at specific frequencies. ASSRs are elicited by temporally modulated auditory stimulation, such as a train of clicks with a fixed inter-click interval, or an amplitude modulated (AM) tone. After the onset of the stimulus, the EEG or MEG rapidly entrains to the frequency and phase of the stimulus. The ASSR is generated by activity within the auditory pathway. The ASSR for modulation frequencies up to 50 Hz is generated from the auditory cortex based on EEG. Higher frequencies of modulation (>80 Hz) are thought to originate from brainstem areas. The type of stimulus may also affect the region of activation within the auditory cortex. Amplitude modulated (AM) tones and click train stimuli are commonly used stimuli to evoke the ASSR.

The EEG sensor can be used as a brain-computer interface (BCI) and provides a direct communication pathway between the brain and the external world by translating signals from brain activities into machine codes or commands to control different types of external devices, such as a computer cursor, cellphone, home equipment or a wheelchair. SSVEP can be used in BCI due to high information transfer rate (ITR), little training and high reliability. The use of in-ear EEG acquisition makes BCI convenient, and highly efficient artifact removal techniques can be used to derive clean EEG signals.

The system can measure visually evoked potential (VEP), visually evoked response (VER) or visually evoked cortical potential (VECP). They refer to electrical potentials, initiated by brief visual stimuli, which are recorded from the scalp overlying visual cortex, VEP waveforms are extracted from the electro-encephalogram (EEG) by signal averaging. VEPs are used primarily to measure the functional integrity of the visual pathways from retina via the optic nerves to the visual cortex of the brain. VEPs better quantify functional integrity of the optic pathways than scanning techniques such as magnetic resonance imaging (MRI). Any abnormality that affects the visual pathways or visual cortex in the brain can affect the VEP. Examples are cortical blindness due to meningitis or anoxia, optic neuritis as a consequence of demyelination, optic atrophy, stroke, and compression of the optic pathways by tumors, amblyopia, and neurofibromatosis. In general, myelin plaques common in multiple sclerosis slow the speed of VEP wave peaks. Compression of the optic pathways such as from hydrocephalus or a tumor also reduces amplitude of wave peaks.

A bioimpedance (BI) sensor can be used to determine a biomarker of total body fluid content. The BIA is a noninvasive method for evaluation of body composition, easy to perform, and fast, reproducible, and economical and indicates nutritional status of patients by estimating the amount of lean body mass, fat mass, body water, and cell mass. The method also allows the assessment of patient's prognosis through the PA, which has been applied in patients with various diseases, including chronic liver disease. The phase angle varies according to the population and can be used for prognosis.

In another embodiment, the BI sensor can estimate glucose level. This is done by measuring the bioimpedance at various frequencies, where high frequency Bi is related to fluid volume of the body and low frequency BI is used to estimate the volume of extracellular fluid in the tissues.

The step of determining the amount of glucose can include comparing the measured impedance with a predetermined relationship between impedance and blood glucose level. In a particular embodiment, the step of determining the blood glucose level of a subject includes ascertaining the sum of a fraction of the magnitude of the measured impedance and a fraction of the phase of the measured impedance. The amount of blood glucose, in one embodiment, is determined according to the equation: Predicted glucose=(0.31) Magnitude+(0.24)Phase where the impedance is measured at 20 kHz. In certain embodiments, impedance is measured at a plurality of frequencies, and the method includes determining the ratio of one or more pairs of measurements and determining the amount of glucose in the body fluid includes comparing the determined ratio(s) with corresponding predetermined ratio(s), i.e., that have been previously correlated with directly measured glucose levels. In embodiments, the process includes measuring impedance at two frequencies and determining the amount of glucose further includes determining a predetermined index, the index including a ratio of first and second numbers obtained from first and second of the impedance measurements. The first and second numbers can include a component of said first and second impedance measurements, respectively. The first number can be the real part of the complex electrical impedance at the first frequency and the second number can be the magnitude of the complex electrical impedance at the second frequency. The first number can be the imaginary part of the complex electrical impedance at the first frequency and the second number can be the magnitude of the complex electrical impedance at the second frequency. The first number can be the magnitude of the complex electrical impedance at the first frequency and the second number can be the magnitude of the complex electrical impedance at the second frequency. In another embodiment, determining the amount of glucose further includes determining a predetermined index in which the index includes a difference between first and second numbers obtained from first and second of said impedance measurements. The first number can be the phase angle of the complex electrical impedance at the first frequency and said second number can be the phase angle of the complex electrical impedance at the second frequency.

The electrodes can be in operative connection with the processor programmed to determine the amount of glucose in the body fluid based upon the measured impedance. In certain embodiments, the processor wireless communicates with an insulin pump programmed to adjust the amount of insulin flow via the pump to the subject in response to the determined amount of glucose. The BIA electrodes can be spaced between about 0.2 mm and about 2 cm from each other.

In another aspect, the BI sensor provides non-invasive monitoring of glucose in a body fluid of a subject. The apparatus includes means for measuring impedance of skin tissue in response to a voltage applied thereto and a microprocessor operatively connected to the means for measuring impedance, for determining the amount of glucose in the body fluid based upon the impedance measurement(s). The means for measuring impedance of skin tissue can include a pair of spaced apart electrodes for electrically conductive contact with a skin surface. The microprocessor can be programmed to compare the measured impedance with a predetermined correlation between impedance and blood glucose level. The apparatus can include means for measuring impedance at a plurality of frequencies of the applied voltage and the program can include means for determining the ratio of one or more pairs of the impedance measurements and means for comparing the determined ratio(s) with corresponding predetermined ratio(s) to determine the amount of glucose in the body fluid.

In a particular embodiment, the apparatus includes means for calibrating the apparatus against a directly measured glucose level of a said subject. The apparatus can thus include means for inputting the value of the directly measured glucose level in conjunction with impedance measured about the same time, for use by the program to determine the blood glucose level of that subject at a later time based solely on subsequent impedance measurements.

One embodiment measures BI at 31 different frequencies logarithmically distributed in the range of 1 kHz to 1 Mhz (10 frequencies per decade). Another embodiment measures BI a t two of the frequencies: 20 and 500 kHz; and in the second set of experiments, 20 kHz only. It may be found in the future that there is a more optimal frequency or frequencies. It is quite possible, in a commercially acceptable instrument that impedance will be determined at at least two frequencies, rather than only one. For practical reasons of instrumentation, the upper frequency at which impedance is measured is likely to be about 500 kHz, but higher frequencies, even has high as 5 MHz or higher are possible and are considered to be within the scope of this invention. Relationships may be established using data obtained at one, two or more frequencies.

One embodiment, specifically for determining glucose levels of a subject, includes a 2-pole BI measurement configuration that measures impedance at multiple frequencies, preferably two well spaced apart frequencies. The instrument includes a computer which also calculates the index or indices that correlate with blood glucose levels and determines the glucose levels based on the correlation(s). an artificial neural network to perform a non-linear regression.

In another embodiment, a BI sensor can estimate sugar content in human blood based on variation of dielectric permeability of a finger placed in the electrical field of transducer. The amount of sugar in human blood can also be estimate by changing the reactance of oscillating circuits included in the secondary circuits of high-frequency generator via direct action of human upon oscillating circuits elements. With this method, the amount of sugar in blood is determined based on variation of current in the secondary circuits of high-frequency generator. In another embodiment, a spectral analysis of high-frequency radiation reflected by human body or passing through the human body is conducted. The phase shift between direct and reflected (or transmitted) waves, which characterizes the reactive component of electrical impedance, represents a parameter to be measured by this method. The concentration of substances contained in the blood (in particular, glucose concentration) is determined based on measured parameters of phase spectrum. In another embodiment, glucose concentration is determined by this device based on measurement of human body region impedance at two frequencies, determining capacitive component of impedance and converting the obtained value of capacitive component into glucose concentration in patient's blood. Another embodiment measures impedance between two electrodes at a number of frequencies and deriving the value of glucose concentration on the basis of measured values. In another embodiment, the concentration of glucose in blood is determined based mathematical model.

The microphone can also detect respiration. Breathing creates turbulence within the airways, so that the turbulent airflow can be measured using a microphone placed externally on the upper chest at the suprasternal notch. The respiratory signals recorded inside the ear canal are weak, and are affected by motion artifacts arising from a significant movement of the earpiece inside the ear canal. A control loop involving knowledge of the degree of artifacts and total output power from the microphones can be used for denoising purposes from jaw movements. Denoising can be done for EEG, ECG, PPG waveforms.

An infrared sensor unit can detect temperature detection in conjunction with an optical identification of objects allows for more reliable identification of the objects, e.g. of the eardrum. Providing the device additionally with an infrared sensor unit, especially arranged centrically at the distal tip, allows for minimizing any risk of misdiagnosis.

In one implementation information relating to characteristics of the patient's tympanic cavity can be evaluated or processed. In this case the electronics includes a camera that detects serous or mucous fluid within the tympanic cavity can be an indicator of the eardrum itself, and can be an indicator of a pathologic condition in the middle ear. Within the ear canal, only behind the eardrum, such body fluid can be identified. Thus, evidence of any body fluid can provide evidence of the eardrum itself, as well as evidence of a pathologic condition, e.g. OME.

In a method according to the preferred embodiment, preferably, an intensity of illumination provided by the at least one light source is adjusted such that light emitted by the at least one light source is arranged for at least partially transilluminating the eardrum in such a way that it can be reflected at least partially by any object or body fluid within the subject's tympanic cavity arranged behind the eardrum. The preferred embodiment is based on the finding that translucent characteristics of the eardrum can be evaluated in order to distinguish between different objects within the ear canal, especially in order to identify the eardrum more reliably. Thereby, illumination can be adjusted such that tissue or hard bone confining the ear canal is overexposed, providing reflections (reflected radiation or light), especially reflections within a known spectrum, which can be ignored, i.e. automatically subtracted out. Such a method enables identification of the eardrum more reliably.

In particular, the degree of reddishness or reflectivity of light in the red spectral range can be determined at different illumination intensities. It can therefore be distinguished more reliably between light reflected by the eardrum itself, or by objects or fluids behind the eardrum, or by the mucosal covering the tympanic cavity wall. The reflectivity of light may be evaluated with respect to reflectivity within e.g. the green or blue spectral range. Typical spectral wavelength maxima are 450 nm (blue light), 550 nm (green light), and 600 nm (red light) for a respective (color) channel. The electronic imaging unit, e.g. comprising a color video camera, or any color sensitive sensor, may record images with respect to the red, green or blue spectral range, respectively. A logic unit may calculate, compare and normalize brightness values for each read, green and blue image, especially with respect to each separate pixel of the respective image. Such an evaluation may also facilitate medical characterization of the eardrum. In particular, the healthy eardrum is a thin, semitransparent membrane containing only few relatively small blood vessels. In contrast, an inflamed eardrum may exhibit thickening and/or increased vascularization. Also, any skin or tissue confining the ear canal as well as any mucosa in the middle ear may be heavily vascularized. In other words: The reflectivity in the different spectral ranges varies considerably between the different structures or objects as well as between healthy and inflamed tissue. Thus, referring to the spectral range enables more reliable differentiation between light reflected by the eardrum itself, or by objects or any fluid behind the eardrum, or by the tympanic cavity wall covered by mucosa.

Thereby, the risk of confounding any red (inflamed) section of the ear canal and the eardrum can be minimized. Also, the eardrum can be identified indirectly by identifying the tympanic cavity. In particular, any opaque fluid, especially amber fluid containing leukocytes and proteins, within the tympanic cavity may influence the spectrum of reflected light, depending on the intensity of illumination. At a relatively high intensity of illumination, the spectrum of reflected light will be typical for scattering in serous or mucous fluid containing particles like leukocytes, as light transmits the eardrum and is at least partially reflected by the opaque fluid. At a relatively low intensity of illumination, the spectrum of reflected light will be dominated by the eardrum itself, as a considerable fraction of the light does not transmit the eardrum, but is directly reflected by the eardrum. Thus, information relating to the tympanic cavity, especially more detailed color information, can facilitate identification of the eardrum as well as of pathologic conditions in the middle ear.

Transilluminating the eardrum can provide supplemental information with respect to the characteristics of the eardrum (e.g. the shape, especially a convexity of the eardrum), and/or with respect to the presence of any fluid within the tympanic cavity. Spectral patterns of reflected light which are typical for eardrum reflection and tympanic cavity reflection can be use to determine the area of interest as well as a physiologic or pathologic condition of the eardrum and the tympanic cavity, especially in conjunction with feedback controlled illumination.

Any fluid within the tympanic cavity evokes a higher degree of reflection than the physiologically present air. The fluid increases reflectance. In contrast, in case the tympanic cavity is filled with air, any light transilluminating the eardrum is only reflected with inferior intensity, as most of the light is absorbed within the tympanic cavity. In other words: transilluminating the eardrum and evaluating reflected light in dependence on the intensity of illumination can facilitate determining specific characteristics of the eardrum, e.g. an absolute degree of reflectivity in dependence on different wavelengths and intensities, providing more information or more certain information with respect to the type of tissue and its condition. Evaluating reflected light can comprise spectral analysis of translucent reflection, especially at different illumination intensities.

The degree of reflection in the red spectrum from the area of the eardrum may depend on the illumination level, i.e. the intensity of illumination. In particular, the red channel reflection can increase with increasing intensity of illumination. The higher the intensity of illumination, the higher the red channel reflection intensity. Also, it has been found that at relatively high intensities of illumination, not only the eardrum, but also any other tissue will reflect more light in the red spectrum. Therefore, on the one hand, providing a control or logic unit which is arranged for adjusting the intensity of illumination can facilitate identification of the eardrum. On the other hand, it can facilitate determining specific characteristics of the eardrum, e.g. an absolute degree of red channel reflection, such that the red channel reflection provides more information or more certain information with respect to the type of tissue and state of the tissue.

The degree of red channel reflection does not increase in the same manner with increasing intensity of illumination, depending on the presence of body fluid behind the eardrum. It has been found that in case there is body fluid within the tympanic cavity, with increasing intensity of illumination, the degree of red channel reflection does not increase as strongly as if the tympanic cavity was empty. Thus, based on the (absolute) degree of red channel reflection, the presence of fluid behind the eardrum can be evaluated. This may facilitate determination of pathologic conditions, e.g. OME.

The camera and process can identify pattern recognition of geometrical patterns, especially circular or ellipsoid shapes, or geometrical patterns characterizing the malleus bone, or further anatomical characteristics of the outer ear or the middle ear. Pattern recognition allows for more reliable identification of the eardrum. Pattern recognition can comprise recognition based on features and shapes such as the shape of e.g. the malleus, the malleus handle, the eardrum or specific portions of the eardrum such as the pasr flaccida or the fibrocartilagenous ring. In particular, pattern recognition may comprise edge detection and/or spectral analysis, especially shape detection of a circular or ellipsoid shape with an angular interruption at the malleus bone or pars flaccida.

In a method according to the preferred embodiment, preferably, the method further comprises calibrating a spectral sensitivity of the electronic imaging unit and/or calibrating color and/or brightness of the at least one light source. Calibration allows for more reliable identification of objects. It has been found that in case the light intensity is very high allowing for passing light through a healthy eardrum, which is semitransparent, a considerable amount of light within the red spectrum can be reflected by the tympanic cavity (especially due to illumination of red mucosa confining the middle ear). Thus, calibrating brightness or the intensity of emitted light enables more accurate evaluation of the (absolute) degree of red channel reflection and its source. In other words, spectral calibration of the imaging sensor in combination with spectral calibration of the illumination means allows for the evaluation of the tissue types and conditions.

Calibration can be carried out e.g. based on feedback illumination control with respect to different objects or different kinds of tissue, once the respective object or tissue has been identified. Thereby, spectral norm curves with respect to different light intensities provide further data based on which calibration can be carried out.

In one embodiment, the camera can extend into the ear canal and can help detect ear issues such as: Chronic disease. Some cases of hearing loss are not caused by a problem with the ear, but by an interruption of blood flow to the ear or brain. Strokes, heart disease, high blood pressure, diabetes, and rheumatoid arthritis can all cause mild to moderate hearing loss.

Meniere's disease. If the user is experiencing extreme dizziness, loss of balance, and nausea, a hearing screening could lead to a diagnosis of Meniere's disease. This condition is caused by an imbalance of fluids in the inner ear, causing a ringing in the ears (tinnitus), a blocked feeling or hearing loss in one or both ears, and severe vertigo.

Paget's disease. This bone disorder may have no early symptoms, and cause lifelong injuries and medical conditions in the patient. As time goes on, patients with Paget's disease may suffer hearing loss and chronic headaches, as well as nerve, bone, and joint pain. In severe cases, patients may have abnormally large head sizes, improper spine curvature, or severe bowing of the arms and legs.

Pendred syndrome. Pendred syndrome is a genetic condition that causes hearing loss, thyroid dysfunction, and balance problems in children. A child who is born with Pendred syndrome is likely to lose hearing function early in life, in some cases before the child reaches three years old. Hearing loss caused by Pendred syndrome will usually worsen over time, and can lead to total deafness.

Otosclerosis. This disease causes the bones in the middle ear to harden, preventing them from conducting sound into the inner ear. Otosclerosis can often be treated or even reversed with surgery.

In one particular variation for treating tinnitus, device may utilize an audio signal, such as music and in particular music having a dynamic signal with intensities varying over time with multiple peaks and troughs throughout the signal. Other audio signals such as various sounds of nature, e.g., rainfall, wind, waves, etc., or other signals such as voice or speech may alternatively be used so long as the audio signal is dynamic. This audio signal may be modified according to a masking algorithm and applied through the device 14 and to the patient to partially mask the patient's tinnitus. An example of how an audio signal may be modified is described in detail in U.S. Pat. No. 6,682,472 (Davis), which is incorporated herein by reference in its entirety and describes a tinnitus treatment which utilizes software to spectrally modify the audio signal in accordance with a predetermined masking algorithm which modifies the intensity of the audio signal at selected frequencies. The described predetermined masking algorithm provides intermittent masking of the tinnitus where the tinnitus is completely masked during peaks in the audio signal and where the perceived tinnitus is detectable to the patient during troughs in the audio signal. Such an algorithm provides for training and habituation by the patient of their tinnitus. Accordingly, the intensity of the audio signal may be modified across the spectrum of the signal and may also be modified to account for any hearing loss that the patient may have incurred. The audio signal having a dynamic spectrum with varying intensities. The audio signal may completely mask the patient's tinnitus during peaks in the signal while during troughs in the audio signal, the tinnitus may be perceived by the patient. Moreover, the masking algorithm may be modified to account for any hearing loss of the patient.

The deep learning network can also be used to identify user health. In embodiments that measure user health with heart rate, BI, ECG, EEG, temperature, or other health parameters, if an outlier situation exists, the system can flag to the user to follow up as an unusual sustained variation from normal health parameters. While this approach may not identify exact causes of the variation, the user can seek help early. For example, a patient may be mostly healthy, but when he or she is sick, the information pops out as outliers from the usual data. Such outliers can be used to scrutinize and predict patient health. The data can be population based, namely that if a population spatially or temporally has the same symptoms, and upon checking with the medical hospitals or doctors to confirm the prediction, public health warnings can be generated. There are two main kinds of machine learning techniques: Supervised learning: in this approach, a training data sample with known relationships between variables is submitted iteratively to the learning algorithm until quantitative evidence ("error convergence") indicates that it was able to find a solution which minimizes classification error. Several types of artificial neural networks work according to this principle; and Unsupervised learning: in this approach, the data sample is analyzed according to some statistical technique, such as multivariate regression analysis, principal components analysis, cluster analysis, etc., and automatic classification of the data objects into subclasses might be achieved, without the need for a training data set.

Medical prognosis can be used to predict the future evolution of disease on the basis of data extracted from known cases such as the prediction of mortality of patients admitted to the Intensive Care Unit, using physiological and pathological variables collected at admission. Medical diagnosis can be done, where ML is used to learn the relationship between several input variables (such as signs, symptoms, patient history, lab tests, images, etc.) and several output variables (the diagnosis categories). An example from my research: using symptoms related by patients with psychosis, an automatic classification system was devised to propose diagnoses of a particular disease. Medical therapeutic decisions can be done where ML is used to propose different therapies or patient management strategies, drugs, etc., for a given health condition or diagnosis. Example from my research: patients with different types of brain hematomas (internal bleeding) were used to train a neural network so that a precise indication for surgery was given after having learned the relationships between several input variables and the outcome. Signal or image analysis can be done, where ML is used to learn how features extracted from physiological signals (such as an EKG) or images (such as an x-ray, tomography, etc.) are associated to some diagnoses. ML can even be used to extract features from signals or images, for example, in the so-called "signal segmentation". Example from my research: non-supervised algorithms were used to extract different image textures from brain MRIs (magnetic resonance imaging), such as bone, meninges, white matter, gray matter, vases, ventricles, etc., and then classifying automatically unknown images, painting each identified region with a different color. In another example large data sets containing multiple variables obtained from individuals in a given population (e.g., those living in a community, or who have a given health care plan, hospital, etc.), are used to train ML algorithms, so as to discover risk associations and predictions (for instance, what patients have a higher risk of emergency risk readmissions or complications from diabetes. Public health can apply ML to predict, for instance, when and where epidemics are going to happen in the future, such as food poisoning, infectious diseases, bouts of environmental diseases, and so on.

The system can collect lifestyle and genetic data from various populations for subsequent prediction and recommendation to similarly situated users. The system collects attributes associated with individuals that co-occur (i.e., co-associate, co-aggregate) with attributes of interest, such as specific disorders, behaviors and traits. The system can identify combinations of attributes that predispose individuals toward having or developing specific disorders, behaviors and traits of interest, determining the level of predisposition of an individual towards such attributes, and revealing which attribute associations can be added or eliminated to effectively modify his or her lifestyle to avoid medical complications. Details captured can be used for improving individualized diagnoses, choosing the most effective therapeutic regimens, making beneficial lifestyle changes that prevent disease and promote health, and reducing associated health care expenditures. It is also desirable to determine those combinations of attributes that promote certain behaviors and traits such as success in sports, music, school, leadership, career and relationships. For example, the system captures information on epigenetic modifications that may be altered due to environmental conditions, life experiences and aging. Along with a collection of diverse nongenetic attributes including physical, behavioral, situational and historical attributes, the system can predict a predisposition of a user toward developing a specific attribute of interest. In addition to genetic and epigenetic attributes, which can be referred to collectively as pangenetic attributes, numerous other attributes likely influence the development of traits and disorders. These other attributes, which can be referred to collectively as non-pangenetic attributes, can be categorized individually as physical, behavioral, or situational attributes. The attribute categories and their interrelationships can correlate physical and behavioral attributes can be collectively equivalent to the broadest classical definition of phenotype, while situational attributes can be equivalent to those typically classified as environmental. In one embodiment, historical attributes can be viewed as a separate category containing a mixture of genetic, epigenetic, physical, behavioral and situational attributes that occurred in the past. Alternatively, historical attributes can be integrated within the genetic, epigenetic, physical, behavioral and situational categories provided they are made readily distinguishable from those attributes that describe the individual's current state. In one embodiment, the historical nature of an attribute is accounted for via a time stamp or other time-based marker associated with the attribute. As such, there are no explicit historical attributes, but through use of time stamping, the time associated with the attribute can be used to make a determination as to whether the attribute is occurring in what would be considered the present, or if it has occurred in the past. Traditional demographic factors are typically a small subset of attributes derived from the phenotype and environmental categories and can be therefore represented within the physical, behavioral and situational categories.

Since the system captures information from various diverse populations, the data can be mined to discover combinations of attributes regardless of number or type, in a population of any size, that cause predisposition to an attribute of interest. The ability to accurately detect predisposing attribute combinations naturally benefits from being supplied with datasets representing large numbers of individuals and having a large number and variety of attributes for each. Nevertheless, the one embodiment will function properly with a minimal number of individuals and attributes. One embodiment of the one embodiment can be used to detect not only attributes that have a direct (causal) effect on an attribute of interest, but also those attributes that do not have a direct effect such as instrumental variables (i.e., correlative attributes), which are attributes that correlate with and can be used to predict predisposition for the attribute of interest but are not causal. For simplicity of terminology, both types of attributes are referred to herein as predisposing attributes, or simply attributes, that contribute toward predisposition toward the attribute of interest, regardless of whether the contribution or correlation is direct or indirect.

Adverse events related to sex and race are also analyzed. For example, for physiological reasons, certain events predominantly occur in males (for example, penile swelling and azoospermia). Drugs that are disproportionately reported as causing adverse events in males were more likely to be synthetically associated with these events. Similarly, adverse events that predominantly occur in either relatively young or relatively old patients are analyzed.

"Off-label" adverse event data is also analyzed, and off-label uses refer to any drug effect not already listed on the drug's package insert. For example, the SIDER database, extracted from drug package inserts, lists 48,577 drug-event associations for 620 drugs and 1092 adverse events that are also covered by the data mining. Offsides recovers 38.8% (18,842 drug-event associations) of SIDER associations from the adverse event reports. Thus, Offsides finds different associations from those reported during clinical trials before drug approval.

Polypharmacy side effects for pairs of drugs (Twosides) are also analyzed. These associations are limited to only those that cannot be clearly attributed to either drug alone (that is, those associations covered in Offsides). The database contains a significant association for which the drug pair has a higher side-effect association score, determined using the proportional reporting ratio (PRR), than those of the individual drugs alone. The system determines pairwise similarity metrics between all drugs in the Offsides and SIDER databases. The system can predict shared protein targets using drug-effect similarities. The side-effect similarity score between two drugs is linearly related to the number of targets that those drugs share.

The system can determine relationships between the proportion of shared indications between a pair of drugs and the similarity of their side-effect profiles in Offsides. The system can use side-effect profiles to suggest new uses for old drugs. While the preferred system predicts existing therapeutic indications of known drugs, the system can recommend drug repurposing using drug-effect similarities in Offsides.

Corroboration of class-wide interaction effects with EMRs. The system can identify DDIs shared by an entire drug class. The class-class interaction analysis generates putative drug class interactions. The system analyzes laboratory reports commonly recorded in EMRs that may be used as markers of these class-specific DDIs.

In one embodiment, the knowledge-based repository may aggregate relevant clinical and/or behavioral knowledge from one or more sources. In an embodiment, one or more clinical and/or behavioral experts may manually specify the required knowledge. In another embodiment, an ontology-based approach may be used. For example, the knowledge-based repository may leverage the semantic web using techniques, such as statistical relational learning (SRL). SRL may expand probabilistic reasoning to complex relational domains, such as the semantic web. The SRL may achieve this using a combination of representational formalisms (e.g., logic and/or frame based systems with probabilistic models). For example, the SRL may employ Bayesian logic or Markov logic. For example, if there are two objects—'asian male' and 'smartness', they may be connected using the relationship 'Asian males are smart'. This relationship may be given a weight (e.g., 0.3). This relationship may vary from time to time (populations trend over years/decades). By leveraging the knowledge in the semantic web (e.g., all references and discussions on the web where 'blonde' and 'smartness' are used and associated) the degree of relationship may be interpreted from the sentiment of such references (e.g., positive sentiment: TRUE; negative sentiment: FALSE). Such sentiments and the volume of discussions may then be transformed into weights. Accordingly, although the system originally assigned a weight of 0.3, based on information from semantic web about Asian males and smartness, may be revised to 0.9.

In an embodiment, Markov logic may be applied to the semantic web using two objects: first-order formulae and their weights. The formulae may be acquired based on the semantics of the semantic web languages. In one embodiment, the SRL may acquire the weights based on probability values specified in ontologies. In another embodiment, where the ontologies contain individuals, the individuals can be used to learn weights by generative learning. In some embodiments, the SRL may learn the weights by matching and analyzing a predefined corpus of relevant objects and/or textual resources. These techniques may be used to not only to obtain first-order waited formulae for clinical parameters, but also general information. This information may then be used when making inferences.

For example, if the first order logic is 'obesity causes hypertension, there are two objects involved: obesity and hypertension. If data on patients with obesity and as to whether they were diagnosed with diabetes or not is available, then the weights for this relationship may be learnt from the data. This may be extended to non-clinical examples such as person's mood, beliefs etc.

The pattern recognizer may use the temporal dimension of data to learn representations. The pattern recognizer may include a pattern storage system that exploits hierarchy and analytical abilities using a hierarchical network of nodes. The nodes may operate on the input patterns one at a time. For every input pattern, the node may provide one of three operations: 1. Storing patterns, 2. Learning transition probabilities, and 3. Context specific grouping.

A node may have a memory that stores patterns within the field of view. This memory may permanently store patterns and give each pattern a distinct label (e.g. a pattern number). Patterns that occur in the input field of view of the node may be compared with patterns that are already stored in the memory. If an identical pattern is not in the memory, then the input pattern may be added to the memory and given a distinct pattern number. The pattern number may be arbitrarily assigned and may not reflect any properties of the pattern. In one embodiment, the pattern number may be encoded with one or more properties of the pattern.

In one embodiment, patterns may be stored in a node as rows of a matrix. In such an embodiment, C may represent a pattern memory matrix. In the pattern memory matrix, each row of C may be a different pattern. These different patterns may be referred to as C-1, C-2, etc., depending on the row in which the pattern is stored.

The nodes may construct and maintain a Markov graph. The Markov graph may include vertices that correspond to the store patterns. Each vertex may include a label of the pattern that it represents. As new patterns are added to the memory contents, the system may add new vertices to the Markov graph. The system may also create a link between to vertices to represent the number of transition events between the patterns corresponding to the vertices. For example, when an input pattern is followed by another input pattern j for the first time, a link may be introduced between the vertices i and j and the number of transition events on that link may be set to 1. System may then increment the number of transition counts on the link from i and j whenever a pattern from i to pattern j is observed. The system may normalize the Markov graph such that the links estimate the probability of a transaction. Normalization may be achieved by dividing the number of transition events on the outgoing links of each vertex by the total number of transition events from the vertex. This may be done for all vertices to obtain a normalized Markov graph. When normalization is completed, the sum of the transition probabilities for each node should add to 1. The system may update the Markov graph continuously to reflect new probability estimates.

The system may also perform context-specific grouping. To achieve this, the system may partition a set of vertices of the Markov graph into a set of temporal groups. Each temporal group may be a subset of that set of vertices of the Markov graph. The partitioning may be performed such that the vertices of the same temporal group are highly likely to follow one another.

The node may use Hierarchical Clustering (HC) to for the temporal groups. The HC algorithm may take a set of pattern labels and their pair-wise similarity measurements as inputs to produce clusters of pattern labels. The system may cluster the pattern labels such that patterns in the same cluster are similar to each other.

As data is fed into the pattern recognizer, the transition probabilities for each pattern and pattern-of-patterns may be updated based on the Markov graph. This may be achieved by updating the constructed transition probability matrix. This may be done for each pattern in every category of patterns. Those with higher probabilities may be chosen and placed in a separate column in the database called a prediction list.

Logical relationships among the patterns may be manually defined based on the clinical relevance. This relationship is specified as first-order logic predicates along with probabilities. These probabilities may be called beliefs. In one embodiment, a Bayesian Belief Network (BBN) may be used to make predictions using these beliefs. The BBN may be used to obtain the probability of each occurrence. These logical relationships may also be based on predicates stored the knowledge base.

The pattern recognizer may also perform optimization for the predictions. In one embodiment, this may be accomplished by comparing the predicted probability for a relationship with its actual occurrence. Then, the difference between the two may be calculated. This may be done for p occurrences of the logic and fed into a K-means clustering algorithm to plot the Euclidean distance between the points. A centroid may be obtained by the algorithm, forming the optimal increment to the difference. This increment may then be added to the (p+1)th occurrence. Then, the process may be repeated. This may be done until the pattern recognizer predicts logical relationships up to a specified accuracy threshold. Then, the results may be considered optimal.

When a node is at the first level of the hierarchy, its input may come directly from the data source, or after some preprocessing. The input to a node at a higher-level may be the concatenation of the outputs of the nodes that are directly connected to it from a lower level. Patterns in higher-level nodes may represent particular coincidences of their groups of children. This input may be obtained as a probability distribution function (PDF). From this PDF, the probability that a particular group is active may be calculated as the probability of the pattern that has the maximum likelihood among all the patterns belonging to that group.

The system can use an expert system that can assess hypertension in according with the guidelines. In addition, the expert system can use diagnostic information and apply the following rules to assess hypertension:

Hemoglobin/hematocrit: Assesses relationship of cells to fluid volume (viscosity) and may indicate risk factors such as hypercoagulability, anemia.

Blood urea nitrogen (BUN)/creatinine: Provides information about renal perfusion/function.

Glucose: Hyperglycemia (diabetes mellitus is a precipitator of hypertension) may result from elevated catecholamine levels (increases hypertension).

Serum potassium: Hypokalemia may indicate the presence of primary aldosteronism (cause) or be a side effect of diuretic-therapy.

Serum calcium: Imbalance may contribute to hypertension.

Lipid panel (total lipids, high-density lipoprotein [HDL], low-density lipoprotein [LDL], cholesterol, triglycerides, phospholipids): Elevated level may indicate predisposition for/presence of atheromatous plaques.

Thyroid studies: Hyperthyroidism may lead or contribute to vasoconstriction and hypertension.

Serum/urine aldosterone level: May be done to assess for primary aldosteronism (cause).

Urinalysis: May show blood, protein, or white blood cells; or glucose suggests renal dysfunction and/or presence of diabetes.

Creatinine clearance: May be reduced, reflecting renal damage.

Urine vanillylmandelic acid (VMA) (catecholamine metabolite): Elevation may indicate presence of pheochromocytoma (cause); 24-hour urine VMA may be done for assessment of pheochromocytoma if hypertension is intermittent.

Uric acid: Hyperuricemia has been implicated as a risk factor for the development of hypertension.

Renin: Elevated in renovascular and malignant hypertension, salt-wasting disorders.

Urine steroids: Elevation may indicate hyperadrenalism, pheochromocytoma, pituitary dysfunction, Cushing's syndrome.

Intravenous pyelogram (IVP): May identify cause of secondary hypertension, e.g., renal parenchymal disease, renal/ureteral-calculi.

Kidney and renography nuclear scan: Evaluates renal status (TOD).

Excretory urography: May reveal renal atrophy, indicating chronic renal disease.

Chest x-ray: May demonstrate obstructing calcification in valve areas; deposits in and/or notching of aorta; cardiac enlargement.

Computed tomography (CT) scan: Assesses for cerebral tumor, CVA, or encephalopathy or to rule out pheochromocytoma.

Electrocardiogram (ECG): May demonstrate enlarged heart, strain patterns, conduction disturbances. Note: Broad, notched P wave is one of the earliest signs of hypertensive heart disease.

The system may also be adaptive. In one embodiment, every level has a capability to obtain feedback information from higher levels. This feedback may inform about certain characteristics of information transmitted bottom-up through the network. Such a closed loop may be used to optimize each level's accuracy of inference as well as transmit more relevant information from the next instance.

The system may learn and correct its operational efficiency over time. This process is known as the maturity process of the system. The maturity process may include one or more of the following flow of steps:

a. Tracking patterns of input data and identifying pre-defined patterns (e.g. if the same pattern was observed several times earlier, the pattern would have already taken certain paths in the hierarchical node structure).

b. Scanning the possible data, other patterns (collectively called Input Sets (IS)) required for those paths. It also may check for any feedback that has come from higher levels of hierarchy. This feedback may be either positive or negative (e.g., the relevance of the information transmitted to the inferences at higher levels). Accordingly, the system may decide whether to send this pattern higher up the levels or not, and if so whether it should it send through a different path.

c. Checking for frequently required ISs and pick the top 'F' percentile of them.

d. Ensuring it keeps this data ready.

In one embodiment, information used at every node may act as agents reporting on the status of a hierarchical network. These agents are referred to as Information Entities (In En). In En may provide insight about the respective inference operation, the input, and the result which collectively is called knowledge.

This knowledge may be different from the KB. For example, the above described knowledge may include the dynamic creation of insights by the system based on its inference, whereas the KB may act as a reference for inference and/or analysis operations. The latter being an input to inference while the former is a product of inference. When this knowledge is subscribed to by a consumer (e.g. administering system or another node in a different layer) it is called "Knowledge-as-a-Service (KaaS)"

One embodiment processes behavior models are classified into four categories as follows:

a. Outcome-based;
b. Behavior-based;
c. Determinant-based; and
d. Intervention-based.

One or more of the following rules of thumb may be applied during behavioral modeling:

One or more interventions affect determinants;
One or more determinants affect behavior; and
One or more behaviors affect outcome.

A behavior is defined to be a characteristic of an individual or a group towards certain aspects of their life such as health, social interactions, etc. These characteristics are displayed as their attitude towards such aspects. In analytical terms, a behavior can be considered similar to a habit. Hence, a behavior may be observed POP™ for a given data from a user. An example of a behavior is dietary habits.

Determinants may include causal factors for behaviors. They either cause someone to exhibit the same behavior or cause behavior change. Certain determinants are quantitative but most are qualitative. Examples include one's perception about a food, their beliefs, their confidence levels, etc.

Interventions are actions that affect determinants. Indirectly they influence behaviors and hence outcomes. System may get both primary and secondary sources of data. Primary sources may be directly reported by the end-user and AU. Secondary data may be collected from sensors such as their mobile phones, cameras, microphone, as well as those collected from general sources such as the semantic web.

These data sources may inform the system about the respective interventions. For example, to influence a determinant called forgetfulness which relates to a behavior called medication, the system sends a reminder at an appropriate time, as the intervention. Then, feedback is obtained whether the user took the medication or not. This helps the system in confirming if the intervention was effective.

The system may track a user's interactions and request feedback about their experience through assessments. The system may use this information as part of behavioral modeling to determine if the user interface and the content delivery mechanism have a significant effect on behavior change with the user. The system may use this information to optimize its user interface to make it more personalized over time to best suit the users, as well as to best suit the desired outcome.

The system also may accommodate data obtained directly from the end-user, such as assessments, surveys, etc. This enables users to share their views on interventions, their effectiveness, possible causes, etc. The system's understanding of the same aspects is obtained by way of analysis and service by the pattern recognizer.

Both system-perceived and end user-perceived measures of behavioral factors may be used in a process called Perception Scoring (PS). In this process, hybrid scores may be designed to accommodate both above mentioned aspects of behavioral factors. Belief is the measure of confidence the system has, when communicating or inferring on information. Initially higher beliefs may be set for user-perceived measures.

Over time, as the system finds increasing patterns as well as obtains feedback in pattern recognizer, the system may evaluate the effectiveness of intervention(s). If the system triggers an intervention based on user-perceived measures and it doesn't have significant effect on the behavior change, the system may then start reducing its belief for user-perceived measures and instead will increase its belief for system-perceived ones. In other words, the system starts believing less in the user and starts believing more in itself. Eventually this reaches a stage where system can understand end-users and their behavioral health better than end-users themselves. When perception scoring is done for each intervention, it may result in a score called Intervention Effectiveness Score (IES).

Perception scoring may be done for both end-users as well as AU. Such scores may be included as part of behavior models during cause-effect analysis.

Causes may be mapped with interventions, determinants, and behavior respectively in order of the relevance. Mapping causes with interventions helps in back-tracking the respective AU for that cause. In simple terms, it may help in identifying whose actions have had a pronounced effect on the end-user's outcome, by how much and using which intervention. This is very useful in identifying AUs who are very effective with specific interventions as well as during certain event context. Accordingly, they may be provided a score called Associated User Influence Score. This encompasses information for a given end-user, considering all interventions and possible contexts relevant to the user's case.

The system may construct one or plans including one or more interventions based on analysis performed, and may be implemented. For example, the system may analyze eligibility of an intervention for a given scenario, evaluating eligibility of two or more interventions based on combinatorial effect, prioritizing interventions to be applied, based on occurrence of patterns (from pattern recognizer), and/or submitting an intervention plan to the user or doctor in a format readily usable for execution.

This system may rely on the cause-effect analysis for its planning operations. A plan consists of interventions and a respective implementation schedule. Every plan may have several versions based on the users involved in it. For example, the system may have a separate version for the physician as compared to a patient. They will in turn do the task and report back to the system. This can be done either directly or the system may indirectly find it based on whether a desired outcome with the end user was observed or not.

The methodology may be predefined by an analyst. For every cause, which can be an intervention(s), determinant(s), behavior(s) or combinations of the same, the analyst may specify one or more remedial actions. This may be specified from the causal perspective and not the contextual perspective.

Accordingly, the system may send a variety of data and information to pattern recognizer and other services, as feedback, for these services to understand about the users. This understanding may affect their next set of plans which in turn becomes an infinite cyclic system where system affects the users while getting affected by them at the same time. Such a system is called a reflexive-feedback enabled system. The system may user both positive and negative reflexive-feedback, though the negative feedback aspect may predominantly be used for identifying gaps that the system needs to address.

The system may provide information, such as one or more newly identified patterns, to an analyst (e.g., clinical analyst or doctor). In the use case, the doctor may be presented with one or more notifications to address the relationship between carbohydrates and the medication that the patient is taking.

One embodiment of the system operation includes receiving feedback relating to the plan, and revising the plan based on the feedback; the feedback being one or more patient behaviors that occur after the plan; the revised plan including one or more additional interventions selected based on the feedback; the one or more patient behaviors that occur after the plan include a behavior transition; determining one or more persons to associate with the identified intervention; automatically revising probabilities from the collected information; storing the revised probabilities, wherein the revised probabilities are used to determine the plan; and/or automatically make one or more inferences based on machine learning using one or more of the clinical information, behavior information, or personal information.

Hypertension metrics may be one type of metrics utilized within the principles of the present disclosure. A hypertension score can be based on any type of alpha-numeric or visual analog scale. Hypertension scales may or may not be clinically validated and may use any scale (e.g. 1-100, 1-10, 1-4), picture, symbol, color, character, number, sound, letter, or written description of hypertension to facilitate the communication of a patient's hypertension level. The type of hypertension scale used may be determined according to a patient's and/or healthcare provider's preferences, and may also be determined based on the needs of a patient including, for example, the patient's age and/or communication capability. In further embodiments, the selected hypertension scale(s) may be determined by a service provider, such as, e.g., an organization implementing the principles of the present disclosure via a suitable software program or application.

Another metric may include a functionality score. A functionality score can be based on any type of alphanumeric or visual analog scale. Non-limiting examples include the American Chronic Pain Association Quality of Life (ACPA QoL) Scale, Global Assessment of Functioning (GAF) Scale, and Short Form SF-36 Health Survey. Functionality scales may or may not be clinically validated and may use any picture, symbol, color, character, number, sound, letter, written description of quality of life, or physical functioning to facilitate communication of a patient's functionality level. The functionality score may be, e.g., based on an assessment of a patient's ability to exercise as well as perform daily tasks and/or perform routine tasks such as, e.g., getting dressed, grocery shopping, cooking, cleaning, climbing stairs, etc. In some embodiments, the selected functionality scale(s) may be determined by a service provider, such as, e.g., an organization implementing the principles of the present disclosure via a suitable software program or application.

A further metric may include a patient's medication usage. Medication use encompasses pharmacologic and therapeutic agents used to treat, control, and/or alleviate hypertension, including prescription drugs as well as over-the-counter medications, therapeutic agents, and other non-prescription agents. Medication use may include different classes of pharmacologic agents. Medication use can be reported in any appropriate units, such as number of doses taken, percentage of treatment plan completed, frequency of doses, and/or dose strength; and may also specify additional information such as the type of formulation taken and the route of administration (oral, enteral, topical, transdermal, parenteral, sublingual etc.). Molecular alternatives (e.g., acid, salt, solvate, complex, and pro-drug forms, etc.) and formulations (e.g., solid, liquid, powder, gel, and suspensions, etc.) are further contemplated. Reported medication use may, for example, include the number of doses and types of medication taken since a previous reported medication use, and may also indicate the number of closes and types of medication taken within a period of time, such as within, the previous 2 hours, 4 hours, 6 hours, 12 hours, 18 hours, 24 hours, 36 hours, or 48 hours. In some embodiments, for example, medication use may be reported in terms of dosage units recommended by a manufacturer or healthcare provider for a given medication (e.g., minimum, maximum, or range of appropriate unit dosage per unit time).

Reported medication use may allow for tracking compliance with a treatment regime. For example, a record of reported medication use may assist a healthcare provider in evaluating medication efficacy, adjusting dosage, and/or adding other medications as necessary.

In some embodiments of the present disclosure, a patient or healthcare provider may create a patient profile comprising, e.g., identifying, characterizing, and/or medical information, including information about a patient's medical history, profession, and/or lifestyle. Further examples of information that may be stored in a patient profile includes diagnostic information such as family medical history, medical symptoms, duration of hypertension, localized vs. general hypertension, etc. Further contemplated as part of a patient profile are non-pharmacologic treatment(s) (e.g., chiropractic, radiation, holistic, psychological, acupuncture, etc.), lifestyle characteristics (e.g., diet, alcohol intake, smoking habits), cognitive condition, behavioral health, and social well-being.

A patient profile may, for example, be stored in a database and accessible for analysis of the patient's reported hypertension metrics. In some embodiments, a patient profile may be created before collecting and/or transmitting a set of hypertension metrics to be received by a server and/or database in other embodiments, a patient profile may be created concurrently with, or even after transmitting/receiving one or more hypertension metrics. In some embodiments a patient profile may be used to establish one or more hypertension metric e and/or reference values. A patient profile may, for example, allow for setting threshold values or ranges, wherein reported hypertension metrics that fall outside of those limits trigger an alert to be sent to the patient or a healthcare provider. Threshold values, limits, or ranges may also be set without reference to a patient profile. In some embodiments, one or more target value(s) (e.g., hypertension metric value(s)) may be set to determine how the reported hypertension metrics compare with the target value(s).

The methods and systems disclosed herein may rely on one or more algorithm(s) to analyze one or more of the described metrics. The algorithm(s) may comprise analysis of data reported in real-time, and may also analyze data reported in real-time in conjunction with auxiliary data stored in a hypertension management database. Such auxiliary data may comprise, for example, historical patient data such as previously-reported hypertension metrics (e.g., hypertension scores, functionality scores, medication use), personal medical history, and/or family medical history. In some embodiments, for example, the auxiliary data includes at least one set of hypertension metrics previously reported and stored for a patient. In some embodiments, the auxiliary data includes a patient profile such as, e.g., the patient profile described above. Auxiliary data may also include statistical data, such as hypertension metrics pooled for a plurality of patients within a similar group or subgroup. Further, auxiliary data may include clinical guidelines such as guidelines relating to hypertension management, including evidence-based clinical practice guidelines on the management of acute and/or chronic hypertension or other chronic conditions.

Analysis of a set of hypertension metrics according to the present disclosure may allow for calibration of the level, degree, and/or quality of hypertension experienced by providing greater context to patient-reported data. For example, associating a hypertension score of 7 out of 10 with high functionality for a first patient, and the same score with low functionality for a second patient may indicate a relatively greater debilitating effect of hypertension on the second patient than the first patient. Further, a high hypertension score reported by a patient taking a particular medication such as opioid analgesics may indicate a need to adjust the patient's treatment plan. Further, the methods and systems disclosed herein may provide a means of assessing relative changes in a patient's distress due to hypertension over time. For example, a hypertension score of 5 out of 10 for a patient who previously reported consistently lower hypertension scores, e.g., 1 out of 10, may indicate a serious issue requiring immediate medical attention.

Any combination(s) of hypertension metrics may be used for analysis in the systems and methods disclosed. In some embodiments, for example, the set of hypertension metrics comprises at least one hypertension score and at least one functionality score. In other embodiments, the set of hypertension metrics may comprise at least one hypertension score, at least one functionality score, and medication use. More than one set of hypertension metrics may be reported and analyzed at a given time. For example, a first set of hypertension metrics recording a patient's current status and a second set of hypertension metrics recording the patient's status at an earlier time may both be analyzed and may also be used to generate one or more recommended actions.

Each hypertension metric may be given equal weight in the analysis, or may also be given greater or less weight than other hypertension metrics included in the analysis. For example, a functionality score may be given greater or less weight with respect to a hypertension score and/or medication use. Whether and/or how to weigh a given hypertension metric may be determined according to the characteristics or needs of a particular patient. As an example, Patient A reports a hypertension score of 8 (on a scale of 1 to 10 where 10 is the most severe hypertension) and a functionality score of 9 (on a scale of 1 to 10 where 10 is highest functioning), while Patient B reports a hypertension score of 8 but a functionality score of 4. The present disclosure provides for the collection, analysis, and reporting of this information, taking into account the differential impact of one hypertension score on a patient's functionality versus that same hypertension score's impact on the functionality of a different patient.

Hypertension metrics may undergo a pre-analysis before inclusion in a set of hypertension metrics and subsequent application of one or more algorithms. For example, a raw score may be converted or scaled according to one or more algorithm(s) developed for a particular patient. In some embodiments, for example, a non-numerical raw score may be converted to a numerical score or otherwise quantified prior to the application of one or more algorithms. Patients and healthcare providers may retain access to raw data (e.g., hypertension metric data prior to any analysis) Algorithm(s) according, to the present disclosure may analyze the set of hypertension metrics according to any suitable methods known in the art. Analysis may comprise, for example, calculation of statistical averages, pattern recognition, application of mathematical models, factor analysis, correlation, and/or regression analysis. Examples of analyses that may be used herein include, but are not limited to, those disclosed in U.S. Patent Application Publication No. 2012/0246102 A1 the entirety of which is incorporated herein by reference.

The present disclosure further provides for the determination of an aggregated hypertension assessment score. In some embodiments, for example, a set of pairs metrics may be analyzed to generate a comprehensive and/or individualized assessment of hypertension by generating a composite or aggregated score. In such embodiments, the aggregated score may include a combination of at least one hypertension score, at least one functionality score, and medication use. Additional metrics may also be included in the aggregated score. Such metrics may include, but are not limited to, exercise habits, mental well-being, depression, cognitive functioning, medication side effects, etc. Any of the aforementioned types of analyses may be used in determining an aggregated score.

The algorithm(s) may include a software program that may be available for download to an input device in various versions. In some embodiments, for example, the algorithm(s) may be directly downloaded through the Internet or other suitable communications means to provide the capability to troubleshoot a health issue in real-time. The algorithm(s) may also be periodically updated, e.g., provided content changes, and may also be made available for download to an input device.

The methods presently disclosed may provide a healthcare provider with a more complete record of a patient's day-to-day status. By having access to a consistent data stream of hypertension metrics for a patient, a healthcare provider may be able to provide the patient with timely advice and real-time coaching on hypertension management options and solutions. A patient may, for example, seek and/or receive feedback on hypertension management without waiting for an upcoming appointment with a healthcare provider or scheduling a new appointment. Such real-time communication capability may be especially beneficial to provide patients with guidance and treatment options during intervals between appointments with a healthcare provider. Healthcare providers may also be able to monitor a patient's status between appointments to timely initiate, modify, or terminate a treatment plan as necessary. For example, a patient's reported medication use may convey whether the patient is taking too little or too much medication. In some embodiments, an alert may be triggered to notify the patient and/or a healthcare provider of the amount of medication taken, e.g., in comparison to a prescribed treatment plan. The healthcare provider could, for example, contact the patient to discuss the treatment plan. The methods disclosed herein may also provide a healthcare provider with a longitudinal review of how a patient responds to hypertension over time. For example, a healthcare provider may be able to determine whether a given treatment plan adequately addresses a patient's needs based on review of the patient's reported hypertension metrics and analysis thereof according to the present disclosure.

Analysis of patient data according to the methods presently disclosed may generate one or more recommended actions that may be transmitted and displayed on an output device. In some embodiments, the analysis recommends that a patient make no changes to his/her treatment plan or routine. In other embodiments, the analysis generates a recommendation that the patient seek further consultation with a healthcare provider and/or establish compliance with a prescribed treatment plan. In other embodiments, the analysis may encourage a patient to seek immediate medical attention. For example, the analysis may generate an alert to be transmitted to one or more output devices, e.g., a first output device belonging to the patient and a second output device belonging to a healthcare provider, indicating that the patient is in need of immediate medical treatment. In some embodiments, the analysis may not generate a recommended action. Other recommended actions consistent with the present disclosure may be contemplated and suitable according to the treatment plans, needs, and/or preferences for a given patient.

The present disclosure further provides a means for monitoring a patient's medication use to determine when his/her prescription will run out and require a refill. For example, a patient profile may be created that indicates a prescribed dosage and frequency of administration, as well as total number of dosages provided in a single prescription. As the patient reports medication use, those hypertension metrics may be transmitted to a server and stored in a database in connection with the patient profile. The patient profile stored on the database may thus continually update with each added metric and generate a notification to indicate when the prescription will run out based on the reported medication use. The notification may be transmitted and displayed on one or more output devices, e.g., to a patient and/or one or more healthcare providers. In some embodiments, the one or more healthcare providers may include a pharmacist. For example, a pharmacist may receive notification of the anticipated date a prescription will run out in order to ensure that the prescription may be timely refilled.

Patient data can be input for analysis according to the systems disclosed herein through any data-enabled device including, but not limited to, portable/mobile and stationary communication devices, and portable/mobile and stationary computing devices. Non-limiting examples of input devices suitable for the systems disclosed herein include smart phones, cell phones, laptop computers, netbooks, personal computers (PCs), tablet PCs, fax machines, personal digital assistants, and/or personal medical devices. The user interface of the input device may be web-based, such as a web page, or may also be a stand-alone application. Input devices may provide access to software applications via mobile and wireless platforms, and may also include web-based applications.

The input device may receive data by having a user, including, but not limited to, a patient, family member, friend, guardian, representative, healthcare provider, and/or caregiver, enter particular information via a user interface, such as by typing and/or speaking. In some embodiments, a server may send a request for particular information to be entered by the user via an input device. For example, an input device may prompt a user to enter sequentially a set of hypertension metrics, e.g., a hypertension score, a functionality score, and information regarding use of one or more medications (e.g., type of medication, dosage taken, time of day, route of administration, etc.). In other embodiments, the user may enter data into the input device without first receiving a prompt. For example, the user may initiate an application or web-based software program and select an option to enter one or more hypertension metrics. In some embodiments, one or more hypertension scales and/or functionality scales may be preselected by the application or software program. For example, a user may have the option of selecting the type of hypertension scale and/or functionality scale for reporting hypertension metrics within the application or software program. In other embodiments, an application or software program may not include preselected hypertension scales or functionality scales such that a user can employ any hypertension scale and/or functionality scale of choice.

The user interface of an input device may allow a user to associate hypertension metrics with a particular date and/or time of day. For example, a user may report one or more hypertension metrics to reflect a patient's present status. A user may also report one or more hypertension metrics to reflect a patient's status at an earlier time.

Patient data may be electronically transmitted from an input device over a wired or wireless medium to a server, e.g., a remote server. The server may provide access to a database for performing an analysis of the data transmitted, e.g., set of hypertension metrics. The database may comprise auxiliary data for use in the analysis as described above. In some embodiments, the analysis may be automated, and may also be capable of providing real-time feedback to patients and/or healthcare providers.

The analysis may generate one or more recommended actions, and may transmit the recommended action(s) over at wired or wireless medium for display on at least one output device. The at least one output device may include, e.g., portable/mobile and stationary communication devices, and portable/mobile and stationary computing devices. Non-limiting examples of output devices suitable for the systems disclosed herein include smart phones, cell phones, laptop computers, netbooks, personal computers (PCs), tablet PCs, fax machines, personal digital assistants, and/or personal medical devices. In some embodiments, the input device is the at least one output device. In other embodiments, the input device is one of multiple output devices. In some embodiments of the present disclosure, the one or more recommended actions are transmitted and displayed on each of two output devices. In such an example, one output device may belong to a patient and the other device may belong to a healthcare provider.

The present disclosure also contemplates methods and systems in a language suitable for communicating with the patient and/or healthcare provider, including languages other than English.

A patient's medical data may be subject to confidentiality regulations and protection. Transmitting, analyzing, and/or storing information according to the methods and systems disclosed herein may be accomplished through secure means, including HIPPA-compliant procedures and use of password-protected devices, servers, and databases.

The systems and methods presently disclosed may be especially beneficial in outpatient, home, and/or on-the-go settings. The systems and methods disclosed herein may also be used as an inpatient tool and/or in controlled medication administration such as developing a personalized treatment plan.

In addition to monitoring health parameters, the system can include interventional devices such as a defibrillator. The defibrillator function is enabled by providing electrical energy of a selected energy/power level/voltage/current level or intensity delivered for a selected duration upon sensing certain patterns of undesirable heart activity wherein said undesirable heart activity necessitates an external delivery of a controlled electrical energy pulse for stimulating a selected heart activity. The defibrillator function is enabled by an intelligent defibrillator appliance that operates in a manner similar to the functions of an intelligent ECG appliance with the additional capability of providing external electrical stimuli via for example a wireless contact system pasted on various locations of the torso. The electrical stimuli are delivered in conjunction with the intelligent defibrillator device or the mobile device performing the additional functions of an intelligent defibrillator appliance. The control actions for providing real time stimuli to the heart of electrical pulses, is enabled by the intelligent defibrillator appliance by itself or in conjunction with an external server/intelligent appliance where the protocols appropriate for the specific individual are resident. The defibrillation actions are controlled in conjunction with the real time ECG data for providing a comprehensive real-time solution to the individual suffering from abnormal or life-threatening heart activity/myocardial infraction. Additionally, by continuously wearing the paste on wireless contacts that can provide the electrical impulse needed, the individual is instantaneously able to get real time attention/action using a specifically designed wearable intelligent defibrillator appliance or a combination of an intelligent ECG plus defibrillator appliance. Further the mobile device such as a cellular telephone or other wearable mobile devices can be configured with the appropriate power sources and the software for performing the additional functions of an intelligent defibrillator appliance specifically tailored to the individual.

The cellular telephone/mobile device can receive signals from the ECG machine/appliance or as an intermediary device that transmits/receives the ECG data and results from a stationary or portable ECG appliance. The ability of the individual to obtain an ECG profile of the heart at a selected time and in a selected location is critical to getting timely attention and for survival. Getting attention within 10 to 20 minutes of a heart attack is crucial beyond that the chances for survival diminish significantly. The smart phone helps the patient to quickly communicate his/her location and or discover the location of the nearest health care facility that has the requisite cardiac care facilities and other facilities. The mobile device that the individual is carrying on the person is enabled to provide the exact location of the individual in conjunction with the global positioning system. In addition, the system is enabled to provide the directions and estimated travel time to/from the health care facility to the specific mobile device/individual.

Yet other intervention can include music, image, or video. The music can be synchronized with respect to a blood pulse rate in one embodiment, and in other embodiments to biorhythmic signal-either to match the biorhythmic signal, or, if the signal is too fast or too slow, to go slightly slower or faster than the signal, respectively. In order to entrain the user's breathing, a basic melody is preferably played which can be easily identified by almost all users as corresponding to a particular phase of respiration. On top of the basic melody, additional layers are typically added to make the music more interesting, to the extent required by the current breathing rate, as described hereinabove. Typically, the basic melody corresponding to this breathing includes musical cords, played continuously by the appropriate instrument during each phase. For some applications, it is desirable to elongate slightly the length of one of the respiratory phases, typically, the expiration phase. For example, to achieve respiration which is 70% expiration and 30% inspiration, a musical composition written for an E:I ratio of 2:1 may be played, but the expiration phase is extended by a substantially-unnoticed 16%, so as to produce the desired respiration timing. The expiration phase is typically extended either by slowing down the tempo of the notes therein, or by extending the durations of some or all of the notes.

Although music for entraining breathing is described hereinabove as including two phases, it will be appreciated by persons skilled in the art that the music may similarly include other numbers of phases, as appropriate. For example, user may be guided towards breathing according to a 1:2:1:3 pattern, corresponding to inspiration, breath holding (widely used in Yoga), expiration, and post-expiratory pause (rest state).

In one embodiment, the volume of one or more of the layers is modulated responsive to a respiration characteristic (e.g., inhalation depth, or force), so as to direct the user to change the characteristic, or simply to enhance the user's connection to the music by reflecting therein the respiration characteristic. Alternatively, or additionally, parameters of the sound by each of the musical instruments may be varied to increase the user's enjoyment. For example, during slow breathing, people tend to prefer to hear sound patterns that have smoother structures than during fast breathing and/or aerobic exercise.

Further alternatively or additionally, random musical patterns and/or digitized natural sounds (e.g., sounds of the ocean, rain, or wind) are added as a decoration layer, especially for applications which direct the user into very slow breathing patterns. The inventor has found that during very slow breathing, it is desirable to remove the user's focus from temporal structures, particularly during expiration.

Still further alternatively or additionally, the server maintains a musical library, to enable the user to download appropriate music and/or music-generating patterns from the Internet into device. Often, as a user's health improves, the music protocols which were initially stored in the device are no longer optimal, so the user downloads the new protocols, by means of which music is generated that is more suitable for his new breathing training. The following can be done:
  obtaining clinical data from one or more laboratory test equipment and checking the data on a blockchain;
  obtaining genetic clinical data from one or more genomic equipment and storing genetic markers in the EMR/HER including germ line data and somatic data over time;
  obtaining clinical data from a primary care or a specialist physician database;
  obtaining clinical data from an in-patient care database or from an emergency room database;
  saving the clinical data into a clinical data repository;
  obtaining health data from fitness devices or from mobile phones;
  obtaining behavioral data from social network communications and mobile device usage patterns;
  saving the health data and behavioral data into a health data repository separate from the clinical data repository; and
  providing a decision support system (DSS) to apply genetic clinical data to the subject, and in case of an adverse event for a drug or treatment, generating a drug safety signal to alert a doctor or a manufacturer, wherein the DSS includes rule-based alerts on pharmacogenetics, oncology drug regimens, wherein the DSS performs ongoing monitoring of actionable genetic variants.

FIG. 7E illustrates one embodiment of a system for collaboratively treating a patient with eye injury. In this embodiment, a treating physician/doctor logs into a consultation system 1 and initiates the process by clicking on "Create New Case" (500). Next, the system presents the doctor with a "New Case Wizard" which provides a simple, guided set of steps to allow the doctor to fill out an "Initial Assessment" form (501). The doctor may enter Patient or Subject Information (502), enter Initial Assessment of patient/case (504), upload Test Results, Subject Photographs and X-Rays (506), accept Payment and Service Terms and Conditions (508), review Summary of Case (510), or submit Forms to a AI machine based "consultant" such as a Hearing Service AI Provider (512). Other clinical information for the cancer subject includes the imaging or medical procedure directed towards the specific disease that one of ordinary skill in the art can readily identify. The list of appropriate sources of clinical information for cancer includes but it is not limited to: CT scan, MRI scan, ultrasound scan, bone scan, PET Scan, bone marrow test, barium X-ray, endoscopy, lymphangiogram, IVU (Intravenous urogram) or IVP (IV pyelogram), lumbar puncture, cystoscopy, immunological tests (anti-malignant antibody screen), and cancer marker tests.

After the case has been submitted, the AI Machine Consultant can log into the system 1 and consult/process the case (520). Using the Treating Doctors Initial Assessment and Photos/X-Rays, the Consultant will click on "Case Consultation" to initiate the "Case Consultation Wizard" (522). The consultant can fill out the "Consultant Record Analysis" form (524). The consultant can also complete the "Prescription Form" (526) and submit completed forms to the original Treating Doctor (528). Once the case forms have been completed by the Consulting Doctor, the Treating Doctor can access the completed forms using the system. The Treating Doctor can either accept the consultation results (i.e. a pre-filled Prescription form) or use an integrated messaging system to communicate with the Consultant (530). The Treating Doctor can log into the system (532), click on Patient Name to review (534), review the Consultation Results (Summary Letter and pre-filled Prescription Form) (536). If satisfied, the Treating Doctor can click "Approve Treatment" (538), and this will mark the case as having being approved (540). The Treating Doctor will be able to print a copy of the Prescription Form and the Summary Letter for submission to hearing aid manufacturer or provider (542). Alternatively, if not satisfied, the Treating Doctor can initiate a computer dialog with the Consultant by clicking "Send a Message" (544). The Treating Doctor will be presented with the "Send a Message" screen where a message about the case under consultation can be written (546). After writing a message, the Treating Doctor would click "Submit" to send the message to the appropriate Consultant (548). The Consultant will then be able to reply to the Treating Doctor's Message and send a message/reply back to the Treating Doctor (550).

A permissioned blockchain can be used to share sensitive medical data with different authorized institutions. The institutions are trusted parties and vouched for by the trusted pont. A Patient-Provider Relationship (PPR) Smart Contract is issued when one node from a trusted institution stores and manages medical records for the patient. The PPR defines an assortment of data pointers and associated access permissions that identify the records held by the care provider. Each pointer consists of a query string that, when executed on the provider's database, returns a subset of patient data. The query string is affixed with the hash of this data subset, to guarantee that data have not been altered at the source. Additional information indicates where the provider's database can be accessed in the network, i.e. hostname and port in a standard network topology. The data queries and their associated information are crafted by the care provider and modified when new records are added. To enable patients to share records with others, a dictionary implementation (hash table) maps viewers' addresses to a list of additional query strings. Each string can specify a portion of the patient's data to which the third party viewer is allowed access. For SQL data queries, a provider references the patient's data with a SELECT query on the patient's address. For patients uses an interface that allows them to check off fields they wish to share through a graphical interface. The system formulates the appropriate SQL queries and uploads them to the PPR on the blockchain.

In one embodiment, the transaction 303 includes the recipient's address 324 (e.g., a hash value based on the receiver's public key), the Blockchain token 309 (i.e., a patient ID 328 and personally identifiable information such as Social Security 326), past medical institution relationship information 331 (if any), and optional other information 310. The transaction 323 is digitally signed by the patient who is the sender's private key to create a digital signature 332 for verifying the sender's identity to the network nodes. The network nodes decrypt the digital signature 332, via the sender's previously exchanged public key, and compare the unencrypted information to the transaction 323. If they match, the sender's authenticity is verified and, after a proper chain of ownership is verified via the ledgers (as explained above), the receiver is recorded in the ledgers as the new Blockchain token 329 authorized owner of the medical information. Block 328 of FIG. 13G can point to off-chain storage warehouses containing the patient's medical history so that the current owner (or all prior owners) can access the patient medical information for treatment. Further, the information can be segmented according to need. This way, if a medication such as cannabis that requires the patient to be an adult, the system can be queried only to the information needed (such as is this patient an adult) and the system can respond only as to the query and there is no need to send other question (in the adult age example, the system replies only adult or not and does not send the birthday to the inquiring system).

In another embodiment, the system includes two look up tables, a global registration look up table (GRLT) where all participants (medical institutions and patients) are recorded with name or identity string, blockchain address for the smart contract, and Patient-Provider lookup table (PPLT). This is maintained by a trusted host authority such as a government health authority or a government payor authority. One embodiment maps participant identification strings to their blockchain address or Ethereum address identity (equivalent to a public key). Terms in the smart contract can regulate registering new identities or changing the mapping of existing ones. Identity registration can thus be restricted only to certified institutions. The PPLT maps identity strings to an address on the blockchain.

Patients can poll their PPLT and be notified whenever a new relationship is suggested or an update is available. Patients can accept, reject or delete relationships, deciding which records in their history they acknowledge. The accepting or rejecting relationships is done only by the patients. To avoid notification spamming from malicious participants, only trusted providers can update the status variable. Other contract terms or rules can specify additional verifications to confirm proper actor behavior.

When Provider 1 adds a record for a new patient, using the GRLT on the blockchain, the patient's identifying information is first resolved to their matching Ethereum address and the corresponding PPLT is located. Provider 1 uses a cached GRLT table to look up any existing records of the patient in the PPLT. For all matching PPLTs, Provider 1 broadcasts a smart contract requesting patient information to all matching PPLT entries. If the cache did not produce a result for the patient identity string or blockchain address, Provider 1 can send a broadcast requesting institutions who handles the patient identity string or the blockchain address to all providers. Eventually, Provider 2 responds with its addresses. Provider 2 may insert an entry for Provider 1 into its address resolution table for future use. Provider 1 caches the response information in its table and can now pull information from Provider 2 and/or supplement the information known to Provider 2 with hashed addresses to storage areas controlled by Provider 1.

Next, the provider uploads a new PPR to the blockchain, indicating their stewardship of the data owned by the patient's Ethereum address. The provider node then crafts a query to reference this data and updates the PPR accordingly. Finally, the node sends a transaction which links the new PPR to the patient's PPLT, allowing the patient node to later locate it on the blockchain.

A Database Gatekeeper provides an off-chain, access interface to the trusted provider node's local database, governed by permissions stored on the blockchain. The Gatekeeper runs a server listening to query requests from clients on the network. A request contains a query string, as well as a reference to the blockchain PPR that warrants permissions to run it. The request is cryptographically signed by the issuer, allowing the gatekeeper to confirm identities. Once the issuer's signature is certified, the gatekeeper checks the blockchain contracts to verify if the address issuing the request is allowed access to the query. If the address checks out, it runs the query on the node's local database and returns the result over to the client.

A patient selects data to share and updates the corresponding PPR with the third-party address and query string. If necessary, the patient's node can resolve the third party address using the GRLT on the blockchain. Then, the patient node links their existing PPR with the care provider to the third-party's Summary Contract. The third party is automatically notified of new permissions, and can follow the link to discover all information needed for retrieval. The provider's Database Gatekeeper will permit access to such a request, corroborating that it was issued by the patient on the PPR they share.

In one embodiment that handles persons without previous blockchain history, admitting procedures are performed where the person's personal data is recorded and entered into the blockchain system. This data may include: name, address, home and work telephone number, date of birth, place of employment, occupation, emergency contact information, insurance coverage, reason for hospitalization, allergies to medications or foods, and religious preference, including whether or not one wishes a clergy member to visit, among others. Additional information may include past hospitalizations and surgeries, advance directives such as a living will and a durable power to attorney. During the time spent in admitting, a plastic bracelet will be placed on the person's wrist with their name, age, date of birth, room number, and blockchain medical record reference on it.

The above system can be used to connect the blockchain with different EHR systems at each point of care setting. Any time a patient is registered into a point of care setting, the EHR system sends a message to the GRLT to identify the patient if possible. In our example, Patient A is in registration at a particular hospital. The PPLT is used to identify Patient A as belonging to a particular plan. The smart contracts in the blockchain automatically updates Patient A's care plan. The blockchain adds a recommendation to put Patient A by looking at the complete history of treatments by all providers and optimizes treat. For example, the system can recommend the patient be enrolled in a weight loss program after noticing that the patient was treated for sedentary lifestyle, had history of hypertension, and the family history indicates a potential heart problem. The blockchain data can be used for predictive analytics, allowing patients to learn from their family histories, past care and conditions to better prepare for healthcare needs in the future. Machine learning and data analysis layers can be added to repositories of healthcare data to enable a true "learning health system" can support an additional analytics layer for disease surveillance and epidemiological monitoring, physician alerts if patients repeatedly fill and abuse prescription access.

In one embodiment, an IOT medical device captures patient data in the hospital and automatically communicates data to a hospital database that can be shared with other institutions or doctors. First, the patient ID and blockchain address is retrieved from the patient's wallet and the medical device attaches the blockchain address in a field, along with other fields receiving patient data. Patient data is then stored in a hospital database marked with the blockchain address and annotated by a medical professional with interpretative notes. The notes are affiliated with the medical professional's blockchain address and the PPR block chain address. A professional can also set up the contract terms defining a workflow. For example, if the device is a blood pressure device, the smart contract can have terms that specify dietary restrictions if the patient is diabetic and the blood pressure is borderline and food dispensing machines only show items with low salt and low calorie, for example.

The transaction data may consist of a Colored Coin implementation (described in more detail at https://en.bitcoin.it/wiki/Colored_Coins which is incorporated herein by reference), based on Open Assets (described in more detail at https://github.com/OpenAssets/open-assets-protocol/blob/master/specification.mediawiki which is incorporated herein by reference), using on the OP_RETURN operator. Metadata is linked from the Blockchain and stored on the web, dereferenced by resource identifiers and distributed on public torrent files. The colored coin specification provides a method for decentralized management of digital assets and smart contracts (described in more detail at https://github.com/ethereum/wiki/wiki/White-Paper which is incorporated herein by reference.) For our purposes the smart contract is defined as an event-driven computer program, with state, that runs on a blockchain and can manipulate assets on the blockchain. So a smart contract is implemented in the blockchain scripting language in order to enforce (validate inputs) the terms (script code) of the contract.

Patient Behavior and Risk Pool Rated Health Plans

With the advent of personal health trackers, new health plans are rewarding consumers for taking an active part in their wellness. The system facilitates open distribution of the consumers wellness data and protect it as PHR must be, and therefore prevent lock-in of consumers, providers and payers to a particular device technology or health plan. In particular, since PHR data is managed on the blockchain a consumer and/or company can grant access to a payer to this data such that the payer can perform group analysis of an individual or an entire company's employee base including individual wellness data and generate a risk score of the individual and/or organization. Having this information, payers can then bid on insurance plans tailored for the specific organization. Enrollment then, also being managed on the blockchain, can become a real-time arbitrage process. The pseudo code for the smart contract to implement a patient behavior based health plan is as follows.

store mobile fitness data
store consumer data in keys with phr_info, claim_info, enrollment_info
for each consumer:
add up all calculated risk for the consumer
determine risk score based on mobile fitness data
update health plan cost based on patient behavior Patient and Provider Data Sharing A patient's Health BlockChain wallet stores all assets, which in turn store reference ids to the actual data, whether clinical documents in HL7 or FHIR format, wellness metrics of activity and sleep patterns, or claims and enrollment information. These assets and control of grants of access to them is afforded to the patient alone. A participating provider can be given full or partial access to the data instantaneously and automatically via enforceable restrictions on smart contracts.

Utilizing the Health BlockChain the access to a patient's PHR can be granted as part of scheduling an appointment, during a referral transaction or upon arrival for the visit. And, access can just as easily be removed, all under control of the patient.

Upon arrival at the doctor's office, an application automatically logs into a trusted provider's wireless network. The app is configured to automatically notify the provider's office of arrival and grant access to the patient's PHR. At this point the attending physician will have access to the patient's entire health history. The pseudo code for the smart contract to implement a patient and provider data sharing is as follows.

Patient download apps and provide login credential and logs into the provider wireless network Patient verifies that the provider wireless network belongs to a patient trusted provider list Upon entering provider premise, system automatically logs in and grants access to provider Patient check in data is automatically communicated with provider system to provide PHR Provider system synchronizes files and obtain new updates to the patient PHR and flags changes to provider.

Patient Data Sharing

Patient's PHR data is valuable information for their personal health profile in order to provide Providers (Physicians) the necessary information for optimal health care delivery. In addition this clinical data is also valuable in an aggregate scenario of clinical studies where this information is analyzed for diagnosis, treatment and outcome. Currently this information is difficult to obtain due to the siloed storage of the information and the difficulty on obtaining patient permissions.

Given a patient Health BlockChain wallet that stores all assets as reference ids to the actual data. These assets can be included in an automated smart contract for clinical study participation or any other data sharing agreement allowed by the patient. The assets can be shared as an instance share by adding to the document a randomized identifier or nonce, similar to a one-time use watermark or serial number, a unique asset (derived from the original source) is then generated for a particular access request and included in a smart contract as an input for a particular request for the patient's health record information. A patient can specify their acceptable terms to the smart contract regarding payment for access to PHR, timeframes for acceptable access, type of PHR data to share, length of history willing to be shared, de-identification thresholds or preferences, specific attributes of the consumer of the data regarding trusted attributes such as reputation, affiliation, purpose, or any other constraints required by the patient. Attributes of the patient's data are also advertised and summarized as properties of the smart contract regarding the type of diagnosis and treatments available. Once the patient has advertised their willingness to share data under certain conditions specified by the smart contract it can automatically be satisfied by any consumer satisfying the terms of the patient and their relevance to the type of PHR needed resulting in a automated, efficient and distributed means for clinical studies to consume relevant PHR for analysis. This process provides an automated execution over the Health BlockChain for any desired time period that will terminate at an acceptable statistical outcome of the required attained significance level or financial limit. The pseudo code for the smart contract to implement automated patient data sharing is as follows.

Patient download apps and provide login credential and logs into the clinical trial provider wireless network Patient verifies that the provider wireless network belongs to a patient trusted provider list Upon entering provider premise, system automatically logs in and grants access to provider Patient check in data is automatically communicated with provider system to provide clinical trial data In one embodiment, a blockchain entry is added for each touchpoint of the medication as it goes through the supply chain from manufacturing where the prescription package serialized numerical identification (SNI) is sent to wholesalers who scan and record the SNI and location and then to distributors, repackagers, and pharmacies, where the SNI/location data is recorded at each touchpoint and put on the blockchain. The medication can be scanned individually, or alternatively can be scanned in bulk. Further, for bulk shipments with temperature and shock sensors for the bulk package, temperature/shock data is captured with the shipment or storage of the medication.

A smart contract assesses against product supply chain rule and can cause automated acceptance or rejection as the medication goes through each supply chain touchpoint. The process includes identifying a prescription drugs by query of a database system authorized to track and trace prescription drugs or similar means for the purpose of monitoring the movements and sale of pharmaceutical products through a supply chain; a.k.a. e-pedigree trail; serialized numerical identification (SNI), stock keeping units (SKU), point of sale system (POS), systems etc. in order to compare the information; e.g. drug name, manufacturer, etc. to the drug identified by the track and trace system and to ensure that it is the same drug and manufacturer of origin. The process can verify authenticity and check pedigree which can be conducted at any point along the prescription drug supply chain; e.g. wholesaler, distributor, doctor's office, pharmacy. The most optimal point for execution of this process would be where regulatory authorities view the greatest vulnerability to the supply chain's integrity. For example, this examination process could occur in pharmacy operations prior to containerization and distribution to the pharmacy for dispensing to patients.

An authenticated prescription drug with verified drug pedigree trail can be used to render an informational object, which for the purpose of illustration will be represented but not be limited to a unique mark; e.g. QR Code, Barcode, Watermark, Stealth Dots, Seal or 2 Dimensional graphical symbol, hereinafter called a certificate, seal, or mark. An exemplary embodiment for use of said certificate, mark, or seal can be used by authorized entities as a warrant of the prescription drug's authenticity and pedigree. For example, when this seal is appended to a prescription vial presented to a patient by a licensed pharmacy, it would represent the prescription drug has gone through an authentication and logistics validation process authorized by a regulatory agency (s); e.g. HHS, FDA, NABP, VIPP, etc. An exemplary embodiment for use of said certificate, mark or seal would be analogous to that of the functioning features, marks, seals, and distinguishing characteristics that currently authenticate paper money and further make it difficult to counterfeit. Furthermore, authorized agents utilizing the certificate process would be analogous to banks participating in the FDIC program.

A user; e.g. patient equipped with the appropriate application on a portable or handheld device can scan the certificate, mark or seal and receive an audible and visible confirmation of the prescription drug's name, and manufacturer. This will constitute a confirmation of the authenticity of the dispensed prescription drug. Extensible use of the certificate, mark, or seal will include but not be limited to; gaining access to website (s) where additional information or interactive functions can be performed; e.g. audible narration of the drug's characteristics and physical property descriptions, dosing, information, and publications, etc. A user; e.g. patient equipped with the appropriate application on a portable or handheld device can scan the certificate, mark, or seal and be provided with notifications regarding; e.g. immediate recall of the medication, adverse events, new formulations, critical warnings of an immediate and emergency nature made by prescription drug regulatory authorities and, or their agents. A user; e.g. patient equipped with a portable or handheld device with the appropriate application software can use the portable and, or handheld device to store prescription drug information in a secure, non-editable format on their device for personal use; e.g. MD's Office Visits, Records Management, Future Authentications, Emergency use by first responders etc. A user; e.g. patient equipped with the appropriate application on a portable or handheld device can scan the drug via an optical scan, picture capture, spectroscopy or other means of identifying its physical properties and characteristics; e.g. spectral signature, size, shape, color, texture, opacity, etc and use this data to identify the prescription drug's name, and manufacturer. A user; e.g. patient equipped with the appropriate application on a portable or handheld device and having the certification system can receive updated information (as a subscriber in a client/server relationship) on a continuing or as needed ad hoc basis (as permitted) about notifications made by prescription drug regulatory authorities regarding; e.g. immediate recall of medications, adverse events, new formulations and critical warnings of an immediate and emergency nature. A user; e.g. patient, subscriber to the certificate system equipped with the appropriate application on a portable or handheld device will be notified by audible and visible warnings of potential adverse affects between drug combinations stored in their device's memory of previously "Certified Drugs." A user; e.g. patient subscriber to the certification system equipped with the appropriate application on a portable or handheld device will receive notification of potential adverse affects from drug combinations, as reported and published by medical professionals in documents and databases reported to; e.g. Drug Enforcement Administration (DEA), Health and Human Services, (HHS) Food and Drug Administration, (FDA) National Library of Medicines, (NLM) and their agents; e.g., Daily Med, Pillbox, RX Scan, PDR, etc.

1. A method for prescription drug authentication by receiving a certificate representing manufacturing origin and distribution touchpoints of a prescription drug on a blockchain.

2. A method of claim 1, comprising retrieving active pharmaceutical ingredients (API) and inactive pharmaceutical ingredients (IPI) from the blockchain.

3. A method of claim 2, comprising authenticating the drug after comparing the API and IPI with data from Drug Enforcement Administration (DEA) Health and Human Services, (HHS) Food and Drug Administration, (FDA) National Library of Medicines, (NLM) etc. for the purpose of identifying the prescription drug'(s) and manufacture name indicated by those ingredients.

4. A method of claim 1, comprising tracing the drug through a supply chain from manufacturer to retailer, dispenser with Pedigree Trail, Serialized Numerical Identification (SNI), Stock Keeping Units (SKU), Point of Sale System (POS) E-Pedigree Systems.

5. A method of claim 1, comprising generating a certificate, seal, mark and computer scannable symbol such as 2 or 3 dimensional symbol; e.g. QR Code, Bar Code, Watermark, Stealth Dots, etc.

It will be readily appreciated that a device such as any of the devices described above may be adapted to perform the method with suitable programming or other configuration of the processor and/or other processing circuitry. Also disclosed herein is a computer program product comprising computer executable code embodied in a non-transitory computer readable medium that, when executing on one or more computing devices, performs the processing steps associated with the method.

It will be appreciated that any of the above systems, devices, methods, processes, and the like may be realized in hardware, software, or any combination of these suitable for the control, data acquisition, and data processing described herein. This includes realization in one or more microprocessors, microcontrollers, embedded microcontrollers, programmable digital signal processors or other programmable devices, along with internal and/or external memory. This may also, or instead, include one or more application specific integrated circuits, programmable gate arrays, programmable array logic components, or any other device or devices that may be configured to process electronic signals. It will further be appreciated that a realization of the processes or devices described above may include computer-executable code created using a structured programming language such as C, an object oriented programming language such as C++, or any other high-level or low-level programming language (including assembly languages, hardware description languages, and database programming languages and technologies) that may be stored, compiled or interpreted to run on one of the above devices, as well as heterogeneous combinations of processors, processor architectures, or combinations of different hardware and software. At the same time, processing may be distributed across devices such as a camera and/or computer and/or server or other remote processing resource in a number of ways, or all of the functionality may be integrated into a dedicated, standalone device. All such permutations and combinations are intended to fall within the scope of the present disclosure.

One of ordinary skill in the art will readily appreciate that alternate but functionally equivalent components, materials, designs, and equipment may be used, particularly including other viewing instruments and smart-viewing devices. Specific elements disclosed herein are not to be interpreted as limiting, but rather as a basis for the claims and as a representative basis for teaching one of ordinary skill in the art to employ the present invention. Accordingly, the above description is intended to cover such alternatives, modifications, and equivalents as may be included within the spirit and scope of the invention as defined by the appended claims. Additionally, the terms "substantially" or "approximately" as used herein may be applied to modify any quantitative representation that could permissibly vary without resulting in a change to the basic function to which it is related.

The invention claimed is:

1. A method to analyze an eye with a mobile device, comprising:
    capturing an eye fundus image using a mobile device camera coupled to a processor;
    capturing gyroscope or accelerometer readings as image metadata to aid in orientation normalization and image registration by the processor;
    extracting features of the eye fundus using the image corrected with image metadata;
    applying the extracted features to analyze the eye fundus images to detect a predetermined eye condition with a deep learning neural network and retrieving treatment or diagnosis information from the detected eye condition; and
    determining intraocular pressure (IOP) with the deep learning neural network based on imaged corneal curvature.

2. The method of claim 1, comprising providing an adapter to couple the mobile device to the eye.

3. The method of claim 1, comprising positioning one or more light emitters or light pipes to carry light from the mobile device in an adapter.

4. The method of claim 1, comprising capturing stereo images of the eye fundus, wherein the adapter enables two or more cameras in the mobile device to image the eye.

5. The method of claim 1, comprising generating historical feature vectors from one or more eye examinations of a patient, training the deep learning neural network with the historical feature vectors along with eye images, and applying the trained deep learning neural network to diagnose the eye.

6. The method of claim 1, comprising providing a similarity search for the eye image.

7. The method of claim 1, comprising displaying from a database eye images similar to the eye image captured by the mobile device camera.

8. The method of claim 1, wherein the mobile device camera comprises an optical zoom lens.

9. The method of claim 8, comprising controlling the optical zoom lens to focus on a posterior of the eye; providing a neural network trained to focus on structures on the posterior of the eye; and imaging the posterior of the eye.

10. The method of claim 1, comprising providing background lighting for imaging cataract in the eye with retro illumination.

11. The method of claim 1, comprising calibrating the IOP with a tonometer in an adapter.

12. The method of claim 1, comprising imaging a posterior of the eye with solid state lighting units and light conditioning optics, further comprising emitting light with narrow spectral bandwidth, broad spectral bandwidth, visible spectrum, or invisible spectrum.

13. The method of claim 1, comprising placing light sources and sensors in an adapter positioned between the mobile device camera and the eye.

14. The method of claim 1, wherein the eye condition comprises myopia, hyperopia, astigmatism, or presbyopia.

15. The method of claim 1, wherein the mobile device compensates for the eye condition during usage.

16. A method to inspect an eye with a mobile device, comprising:
    capturing an eye fundus image using a mobile device camera coupled to a processor;
    capturing gyroscope or accelerometer readings as image metadata for image registration by the processor;
    extracting features of the eye fundus using the image corrected with image metadata;
    applying the extracted features to analyze the eye fundus images to detect a predetermined eye condition with a deep learning neural network and retrieving treatment or diagnosis information from the detected eye condition; and
    determining intraocular pressure (IOP) with the deep learning neural network based on imaged corneal curvature.

17. A method to inspect an eye with a mobile device, comprising:
    capturing gyroscope or accelerometer readings as image metadata to aid in orientation normalization and image registration by the processor;
    extracting features of the eye fundus using the image corrected with image metadata;
    applying the extracted features to analyze the eye fundus images with a deep learning neural network and retrieving diagnosis information from the detected eye condition; and
    determining intraocular pressure (IOP) with the deep learning neural network based on imaged corneal curvature.

18. The method of claim 17, comprising imaging a posterior of the eye with solid state lighting units and light conditioning optics, further comprising emitting light with narrow spectral bandwidth, broad spectral bandwidth, visible spectrum, or invisible spectrum.

19. The method of claim 17, comprising placing light sources and sensors in an adapter positioned between the mobile device camera and the eye.

20. The method of claim 17, wherein the eye condition comprises myopia, hyperopia, astigmatism, or presbyopia.

* * * * *